United States Patent
Singh et al.

(10) Patent No.: US 9,822,184 B2
(45) Date of Patent: Nov. 21, 2017

(54) DCLK1 SHORT FORM SPECIFIC BINDING AGENTS

(71) Applicants: Pomila Singh, Galveston, TX (US); Shubhashish Sarkar, Galveston, TX (US); Malaney O'Connell, Galveston, TX (US)

(72) Inventors: Pomila Singh, Galveston, TX (US); Shubhashish Sarkar, Galveston, TX (US); Malaney O'Connell, Galveston, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 15/136,007

(22) Filed: Apr. 22, 2016

(65) Prior Publication Data
US 2016/0311928 A1    Oct. 27, 2016

Related U.S. Application Data

(60) Provisional application No. 62/151,317, filed on Apr. 22, 2015.

(51) Int. Cl.
| A61K 39/00 | (2006.01) |
| A61K 38/00 | (2006.01) |
| C07K 16/40 | (2006.01) |
| G01N 33/574 | (2006.01) |

(52) U.S. Cl.
CPC ....... *C07K 16/40* (2013.01); *G01N 33/57419* (2013.01); *A61K 39/00* (2013.01); *C07K 2317/34* (2013.01); *G01N 2333/91215* (2013.01)

(58) Field of Classification Search
CPC . C07K 16/40; A61K 39/395; G01N 33/57419
See application file for complete search history.

(56) References Cited

U.S. PATENT DOCUMENTS

2014/0315754 A1    10/2014    Singh et al. .............. 506/10

FOREIGN PATENT DOCUMENTS

NL        EP 0978562 A1 *  2/2000  ........... C12N 9/1205

OTHER PUBLICATIONS

Omori et al., (J Hum Genet. 1998:43:169-177).*
Nakanishi et al., (Nature Genetics. 2013; 45:98-103, ePub Dec. 2, 2012).*
Andresen, "Novel target genes and a valid biomarker panel identified for cholangiocarcinoma," Epigenetics. 7:11, 1249-1257, 2012.
Bailey et al., "DCLK1 marks a morphologically distinct subpopulation of cells with stem cell properties in preinvasive pancreatic cancer," *Gastroenterology*. 2014, 146(1):245-56.
Barker, et al., "Identification of stem cells in small intestine and colon by marker gene Lgr5," Nature. vol. 449, 2007, pp. 1003-1007.

(Continued)

*Primary Examiner* — Cherie M Stanfield
(74) *Attorney, Agent, or Firm* — Norton Rose Fulbright US LLP

(57) ABSTRACT

Certain embodiments are directed to composition and methods related to DCLK1-S specific binding agents.

20 Claims, 31 Drawing Sheets

(56) References Cited

OTHER PUBLICATIONS

Berke et al., "A complex program of striatal gene expression induced by dopaminergic stimulation," *J Neurosci.* 1998, 18(14):5301-10.

Burgess et al., "Alternative splice variants of doublecortin-like kinase are differentially expressed and have different kinase activities," *J Biol Chem.* 2002, 277(20):17696-705.

Dijkmans, et al., "The Doublecortin Gene Family and Disorders of Neuronal Structure," Central Nervous System Agents in Medicinal Chemistry. 10:32-46, 2010.

Do, et al., "A New Biomarker That Predicts Colonic Neoplasia Outcome in Patients with Hyperplastic Colonic Polyps," Cancer Prev. Res. 5:675-684, 2012.

Engels et al., "Functional differences between two DCLK splice variants," *Brain Res Mol Brain Res.* 2004, 120(2):103-14.

Gerbe et al., "DCAMKL-1 expression identifies Tuft cells rather than stem cells in the adult mouse intestinal epithelium," *Gastroenterology.* 2009, 137(6):2179-80.

Giannakis et al., "Molecular properties of adult mouse gastric and intestinal epithelial progenitors in their niches," *J Biol Chem.* 2006, 281(16):11292-300.

Jin et al., "Inactivating cholecystokinin-2 receptor inhibits progastrin-dependent colonic crypt fission, proliferation, and colorectal cancer in mice," *J Clin Invest.* 2009, 119(9):2691-701.

Kantara et al., "Curcumin promotes autophagic survival of a subset of colon cancer stem cells, which are ablated by DCLK1-siRNA," *Cancer Res.* 2014, 74(9):2487-98.

Kemper et al., "Monoclonal antibodies against Lgr5 identify human colorectal cancer stem cells," *Stem Cells,* 2012, 30(11):2378-86.

Le Hellard et al., "Variants in Doublecortin- and Calmodulin Kinase Like 1, a Gene Up-Regulated by BDNF, Are Associated with Memory and General Cognitive Abilities," *PLoS One.* 2009, 4(10):e7534.

Leong, et al., "Epitope retrieval with microwaves: A comparison of citrate buffer and EDTA with three commercial retrieval solutions," App Immunohistochem. 4(3):201-7, 1996.

Lin et al., "DCAMKL1 encodes a protein kinase with homology to doublecortin that regulates microtubule polymerization," *J Neurosci.* 2000, 20(24):9152-61.

May et al., "Identification of a novel putative gastrointestinal stem cell and adenoma stem cell marker, doublecortin and CaM kinase-like-1, following radiation injury and in adenomatous polyposis coli/multiple intestinal neoplasia mice," *Stem Cells,* 2008, 26(3):630-7.

May et al., "Doublecortin and CaM kinase-like-1 and leucine-rich-repeat-containing G-protein-coupled receptor mark quiescent and cycling intestinal stem cells, respectively," *Stem Cells.* 2009, 27(10):2571-9.

May et al., "Brief report: Dclk1 deletion in tuft cells results in impaired epithelial repair after radiation injury," *Stem Cells.* 2014, 32(3):822-7.

Nakanishi et al., "Dclk1 distinguishes between tumor and normal stem cells in the intestine," *Nat Genet.* 2013, 45(1):98-103.

Nomura et al., "CD133 initiates tumors, induces epithelial-mesenchymal transition and increases metastasis in pancreatic cancer," *Oncotarget,* 2015, vol. 6, pp. 8313-8322.

O'Sullivan et al., "Methods for the preparation of enzyme-antibody conjugates for use in enzyme immunoassay," Methods in Enzymology. 73: 147-67, 1981.

Omori et al., "Expression and chromosomal localization of KIAA0369, a putative kinase structurally related to Doublecortin," *J Hum Genet.* 1998, 43(3):169-77.

Pal et al., "Alternative transcription exceeds alternative splicing in generating the transcriptome diversity of cerebellar development," *Genome Res.* 2011, 21(8):1260-72.

Park et al., "shRNA against CD44 inhibits cell proliferation, invasion and migration, and promotes apoptosis of colon carcinoma cells," *Oncol Rep.* 2012, 27(2):339-46.

Sarkar et al., "Annexin A2 mediates up-regulation of NF-κB, β-catenin, and stem cell in response to progastrin in mice and HEK-293 cells," *Gastroenterology.* 2011, 140(2):583-95.e4.

Sarkar et al., "Progastrin overexpression imparts tumorigenic/metastatic potential to embryonic epithelial cells: phenotypic differences between transformed and nontransformed stem cells," *Int J Cancer.* 2012, 131(7):E1088-99.

Schepers et al., "Lineage tracing reveals Lgr5+ stem cell activity in mouse intestinal adenomas," *Science,* 2012, 337(6095):730-5.

Shang et al., "Catalytic and regulatory domains of doublecortin kinase-1," *Biochemistry.* 2003, 42(7):2185-94.

Shin et al., "Doublecortin-like kinase enhances dendritic remodelling and negatively regulates synapse maturation," *Nat Commun.* 2013, 4:1440.

Shu et al., "Doublecortin-like kinase controls neurogenesis by regulating mitotic spindles and M phase progression," *Neuron.* 2006, 49(1):25-39.

Siddheshwar, et al., "Plasma levels of progastrin but not amidated gastrin or glycine extended gastrin are elevated in patients with colorectal carcinoma," Gut. 48:47-52, 2001.

Silverman et al., "CPG16, a novel protein serine/threonine kinase downstream of cAMP-dependent protein kinase," *J Biol Chem.* 1999, 274(5):2631-6.

Singh, et al., "Gastrin gene expression is required for the proliferation and tumorigenicity of human colon cancer cells," Cancer Res. 56:4111-5, 1996.

Singh, et al., "Progastrin Peptides Increase the Risk of Developing Colonic Tumors: Impact on Colonic Stem Cell," Curr Colorectal Cancer Rep. 8:277-89, 2012.

Singh, et al., "Annexin II binds progastrin and gastrin-like peptides, and mediates growth factor effects of autocrine and exogenous gastrins on colon cancer and intestinal epithelial cells," Oncogene. 26:425-40, 2007.

Singh, et al., "Expression of IGF-II and IGF-binding proteins by colon cancer cells in relation to growth response to IGFs," The American Physiological Society 267. G608-G617, 1994.

Sureban et al., "Nanoparticle-based delivery of siDCAMKL-1 increases microRNA-144 and inhibits colorectal cancer tumor growth via a Notch-1 dependent mechanism," *J Nanobiotechnology.* 2011, 9:40.

Sureban, et al., "Selective blockade of DCAMKL-1 results in tumor growth arrest by a Let-7a MicroRNA-dependent mechanism," Gastroenterol. 137:649-59, 2009.

Vedeld, et al., "The recently suggested intestinal cancer stem cell marker DCLK1 is an epigenetic biomarker for colorectal cancer," Epigenetics. 9(3):346-50, 2014.

Verissimo et al., "Silencing of the microtubule-associated proteins doublecortin-like and doublecortin-like kinase-long induces apoptosis in neuroblastoma cells," *Endocr Relat Cancer.* 2010, 17(2):399-414.

Verissimo et al., "Silencing of Doublecortin-Like (DCL) Results in Decreased Mitochondrial Activity and Delayed Neuroblastoma Tumor Growth," *PLoS One.* 2013, 8(9):e75752.

Vreugdenhil et al., "Kainate-elicited seizures induce mRNA encoding a CaMK-related peptide: a putative modulator of kinase activity in rat hippocampus," *J Neurobiol.* 1999, 39(1):41-50.

Westphalen et al., "Long-lived intestinal tuft cells serve as colon cancer-initiating cells," *J Clin Invest.* 2014, 124(3):1283-95.

Zufferey, et al., "Woodchuck hepatitis virus posttranscriptional regulatory element enhances expression of transgenes delivered by retroviral vectors," J Virol. 73(4):2886, 1999.

\* cited by examiner

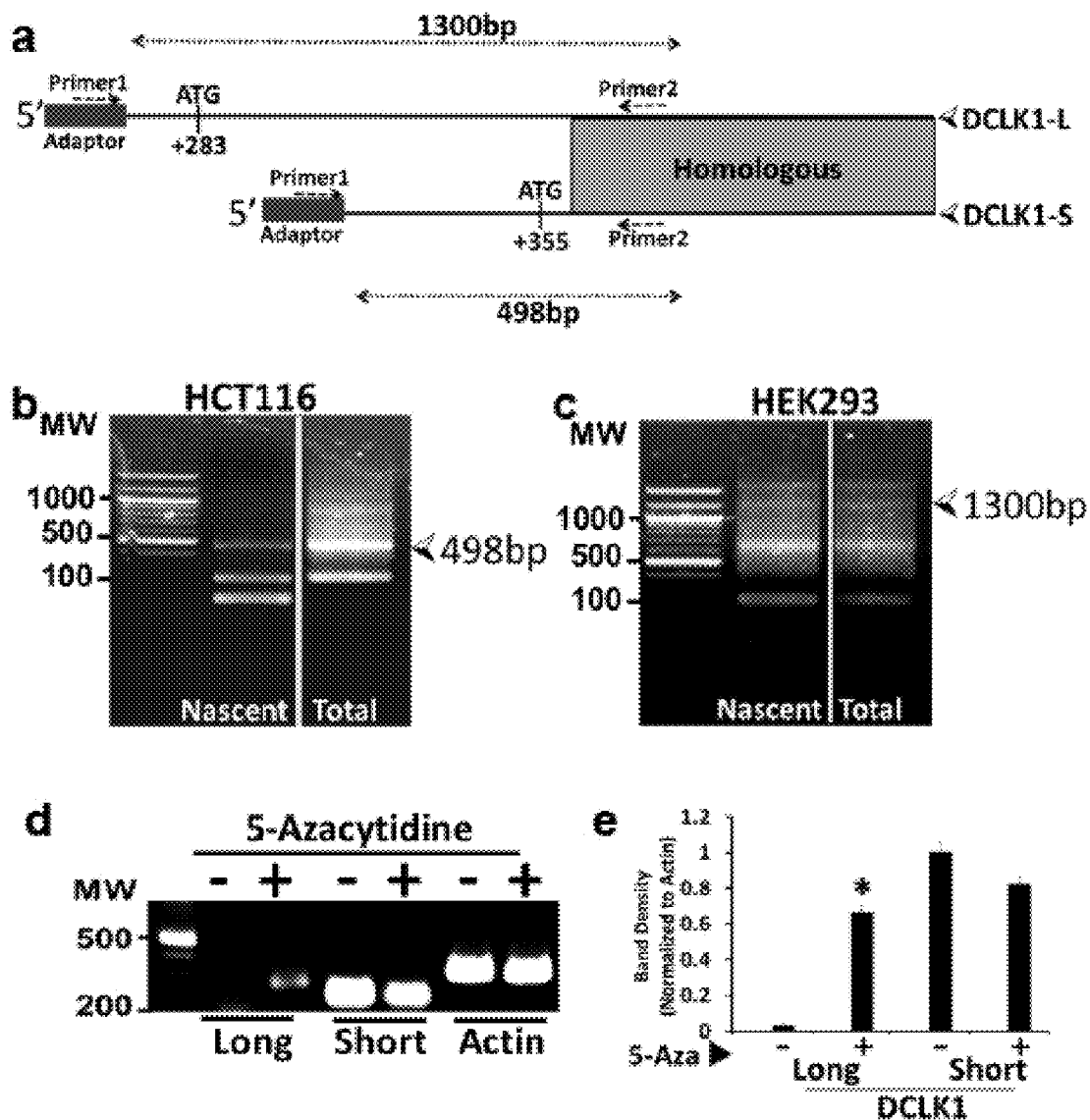
FIG. 4A-E

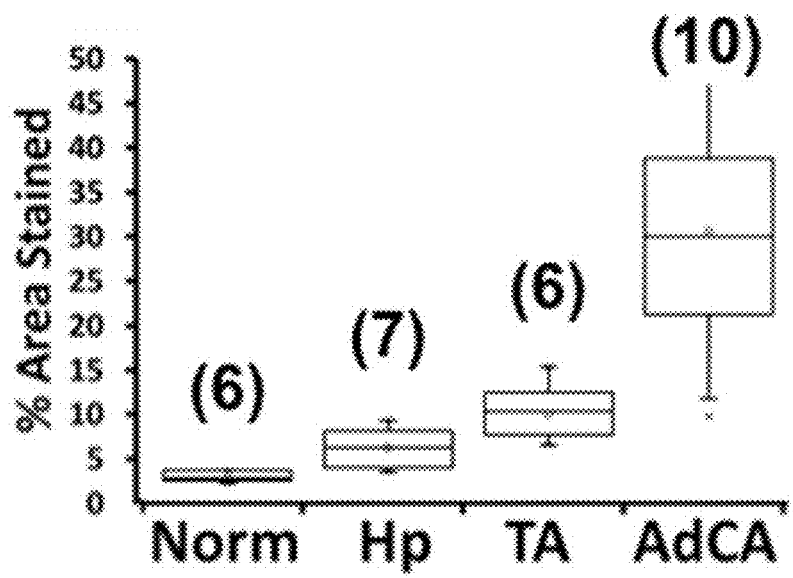
FIG. 19
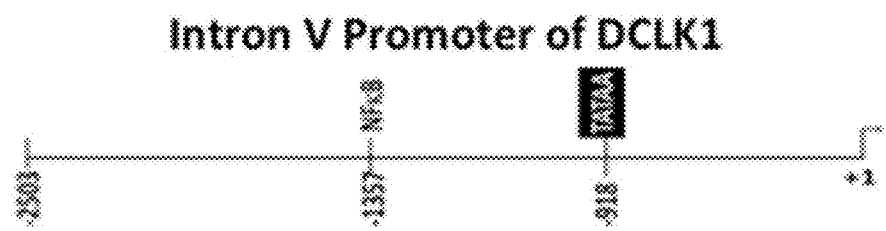
FIG. 20
Antigenic Peptide to raise polyclonal
Antibody against DCLK1-S
NH2-(MLELIE)8K4K2KXC-NH2----KLH
FIG. 21

DCLK1 SHORT FORM SPECIFIC BINDING AGENTS

PRIORITY PARAGRAPH

This Application claims priority to U.S. Provisional Patent Application Ser. No. 62/151,317 filed Apr. 22, 2015, which is incorporated herein by reference in its entirety.

STATEMENT REGARDING FEDERALLY FUNDED RESEARCH

This invention was made with government support under CA979509, CA72851, and CA181572 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Colorectal cancer (CRC) is the third most prevalent cancer in the U.S. (Siegel et al., *CA Cancer J Clin.* 2014, 64(2):104-17). Cancer stem cells (CSCs) are thought to be resistant to current best practice treatments and believed to contribute to tumor metastasis (Ning et al., *Cancer Biol Ther.* 2013, 14(4):295-303). There is thus a critical need for identifying and selectively targeting CSCs. Several cancer stem cell markers have been identified in literature, including CD44, CD133, Lgr5 and DCLK1 (Park et al., *Oncol Rep.* 2012, 27(2):339-46; Nomura et al., *Oncotarget,* 2015, PubMed PMID: 25829252; Schepers et al., *Science,* 2012, 337(6095):730-5; Kemper et al., *Stem Cells,* 2012, 30(11): 2378-86; May et al., *Stem Cells,* 2008, 26(3):630-7; Nakanishi et al., *Nat Genet.* 2013, 45(1):98-103). Besides marking the cancer stem cells, CD44, CD133 and Lgr5 have been reported to play an important functional role in either maintaining the growth of the cancer cells and/or in aiding the metastatic potential of the cells (Park et al., *Oncol Rep.* 2012, 27(2):339-46; Nomura et al., *Oncotarget,* 2015, PubMed PMID: 25829252; Schepers et al., *Science,* 2012, 337(6095):730-5; Kemper et al., *Stem Cells,* 2012, 30(11): 2378-86). More recently, an equally important role of DCLK1 has been implicated in colon tumorigenesis in mice (Nakanishi et al., *Nat Genet.* 2013, 45(1):98-103; Westphalen et al., *J Clin Invest.* 2014, 124(3):1283-95; Bailey et al., *Gastroenterology.* 2014, 146(1):245-56) and in maintaining the proliferative potential of human colon cancer cells (Kantara et al., *Cancer Res.* 2014, 74(9):2487-98; Sarkar et al., *Int J Cancer.* 2012, 131(7):E1088-99; Sureban et al., *J Nanobiotechnology.* 2011, 9:40). It was recently reported that a subset of DCLK1+CSCs were resistant to inhibitory effects of chemopreventive/chemotherapeutic agents, and down-regulation of DCLK1 combined with chemoprevention was required for eliminating CSCs, in vitro and in vivo, and for avoiding relapse (in terms of re-formation of tumorospheres from treated cells) (Kantara et al., *Cancer Res.* 2014, 74(9):2487-98). These findings highlighted a possible critical role of DCLK1 in maintaining the growth of human colon cancer cell lines, by perhaps protecting the CSC-like populations. Isogenic clones of human embryonic epithelial cells (HEK293), that were either poorly tumorigenic (HEKC) or highly metastatic (HEKmGAS), expressed identical set of stem cell markers, including DCLK1 (Sarkar et al., *Int J Cancer.* 2012, 131(7): E1088-99). Thus, specifically targeting CSCs has remained a challenge and there remains a need for addition methods for identifying cancerous cells and cancer therapies, particularly for CRC.

SUMMARY

The cDNA sequence of DCLK1-S is almost identical to that of DCLK1-L, other than the fact that DCLK1-S lacks the cDNA sequence at the 5' end which corresponds to the double-cortin domains in DCLK1-L. By comparing the nucleotide sequences, a 17 bp sequence was identified at the 5' end of DCLK1-S that was specific to DCLK1-S and was not homologous with any part of the DCLK1-L sequence. The peptide fragment, at the N-terminal end of DCLK1-S, which corresponded to the unique 17 bps of DCLK1-S transcript (FIG. 21) was used to generate monospecific polyclonal antibodies, i.e., polyclonal antibodies that recognize the MLELIE (SEQ ID NO:1) epitope specific for DCKL1-S. Certain aspects are directed to monoclonal antibodies that are specific for the DCLK1-S isoform.

Certain embodiments are directed to antibodies that specifically bind DCLK1-S. Western blot analysis of normal and cancer cell lines that either expressed only the long isoform or the short isoform where used to verify the specificity of the DCLK1-S specific antibody. In certain aspects the DCLK1-S specific antibody binds the peptide MLELIE (SEQ ID NO:1). In certain aspects the DCLK1-S specific antibody can be used in immunohistochemical and/or immunofluorescent detection assays. In a further aspect DCLK1-S specific antibody can be used to detect the short isoform in human adenocarcinomas.

Certain embodiments are directed to methods of detecting the presence of transformed and dyspastic cells in the colonic mucosal samples of patients (see FIG. 18 and FIG. 19) using the DCLK1-S specific antibody and using these methods as a prognostic/diagnostic marker for predicting the risk for developing colorectal cancers. The relative expression of DCLK1-S in the tumor tissue sections can be used for predicting disease-free interval and overall survival of the patients, based on data presented in FIG. 9, FIG. 31, and FIG. 32. Patients positive for DCLK1-S staining in their mucosal/tumor specimens/tissue sections could then be treated with specific inhibitors which can target the expression of DCLK1-S or target the functions of DCLK1-S for prevention/treatment purposes. In addition to using DCKL1-S as a biomarker other related biomarkers can be used in conjunction with DCKL1-S as a biomarker panel. In certain aspects the absence or presence of DCKL1-S can be detected or measured. In a further aspect DCLK1-S can be detected or measured with one or more additional biomarkers including FOXD3, COL3A1, or SPARC (FIG. 31 and FIG. 32). In certain aspects one of skill can conclude a poor prognosis if DCLK1-S is elevated and FOXD3 is decreased. A high DCLK1-S to FOXD3 ratio signals a poor prognosis. A DCLK1-S specific antibody, e.g., PS-41014, does not significantly detect the presence of DCLK1-L.

Certain embodiments are directed to a recombinant DCLK1-S human antigenic peptide or an immunogenic composition comprising the same for producing DCLK1-S specific antibodies. In certain aspects the immunogenicity of a six amino acid MLELIE peptide can be enhanced using 8 copies of the peptide called MAP-8 (Multiple Antigen Peptide octavalent) fused to a lysine-branched scaffold. This conjugation produced the peptide ($NH_2$-MLELIE)

8K4K2KXC-NH$_2$, (C=cysteine; X=beta-Ala) and was conjugated finally to KLH. 100-200 µg of this modified antigenic peptide mixed with Complete Freund's Adjuvant (CFA) was used as an immunogen and injected to New Zealand rabbit. Immunogen was diluted in 0.5 ml sterile saline solution and mixed with 0.5 ml adjuvant to form an emulsion that was injected subcutaneously in the shoulder region of the animal and intramuscularly in the large muscle of the rear leg. For subsequent booster injection the CFA was replaced by IFA (Incomplete Freund's Adjuvant). First bleed was collected on day 21 post immunization and following bleeds were collected every two weeks till day 91. The collected serum was purified in an immune-affinity matrix coupled to native peptide and polyclonal IgG was purified to homogeneity. The purified antibody was used for subsequent western blot and IHC/IF assays.

In another aspect, the present invention provides kits for specifically detecting DCLK1-S. The kits can be used to detect DCLK1-S. In one embodiment, the kit comprises a solid support, such as a chip, a microtiter plate or a bead or resin having a capture reagent attached thereon, wherein the capture reagent binds DCLK1-S. Thus, for example, the kits of the present invention can comprise mass spectrometry probes for SELDI, such as ProteinChip® arrays. In the case of DCLK1-S specific capture reagents, the kit can comprise a solid support with a reactive surface, and a container comprising the biospecific capture reagent.

The kit can also comprise a washing solution or instructions for making a washing solution, in which the combination of the DCLK1-S capture reagent and the washing solution allows capture of DCLK1-S on the solid support for subsequent detection by, e.g., mass spectrometry. The kit may include more than type of adsorbent, each present on a different solid support. In a further embodiment, such a kit can comprise instructions for suitable operational parameters in the form of a label or separate insert. For example, the instructions may inform a consumer about how to collect the sample, how to wash the probe or the particular biomarkers to be detected.

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

"Antibody" refers to all isotypes of immunoglobulins (IgG, IgA, IgE, IgM, IgD, and IgY) including various monomeric and polymeric forms of each isotype, unless otherwise specified. "Functional fragments" of such antibodies comprise portions of antibodies that retain antigen-binding specificity of the parent antibody molecule. For example, functional fragments can comprise at least the CDRs of either the heavy chain or light chain variable region. Functional fragments can also comprise the heavy chain or light chain variable region, or sequences that are substantially similar to the heavy or light chain variable region. Further suitable functional fragments include, without limitation, antibodies with multiple epitope specificity, bispecific antibodies, diabodies, and single-chain molecules, as well as Fab, F(ab')2, Fd, Fabc, and Fv molecules, single chain (Sc) antibodies (also called ScFv), individual antibody light chains, individual antibody heavy chains, chimeric fusions between antibody chains and other molecules, heavy chain monomers or dimers, light chain monomers or dimers, dimers consisting of one heavy and one light chain, and the like. All antibody isotypes can be used to produce functional fragments of the antibodies herein. Functional fragments can be recombinantly or synthetically produced, with natural or unnatural nucleic acid or amino acid molecules. In certain aspects an antibody can be a monospecific polyclonal antibody or a monoclonal antibody.

The antibodies or functional fragments thereof of the disclosed subject matter can be generated from any species. The antibodies or functional fragments thereof described herein can be labeled or otherwise conjugated to various chemical or biomolecule moieties, for example, for therapeutic or diagnostic or detection or treatment applications. The moieties can be cytotoxic, for example, bacterial toxins, viral toxins, radioisotopes, and the like. The moieties can be detectable labels, for example, fluorescent labels, radiolabels, biotin, and the like, which are known in the art. In certain aspects the antibodies of the present invention are used for flow cytometric detection, for scanning laser cytometric detection, or for fluorescent immunoassay, they can usefully be labeled with fluorophores. There are a wide variety of fluorophore labels that can usefully be attached to the antibodies of the present invention. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCPCy5.5, PE-Cy5, PE-Cy5.5, PE-Cy7, PE-Texas Red, and APC-Cy7. Other fluorophores include, inter alia, Alexa Fluor® 350, Alexa Fluor® 488, Alexa 25 Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention. For secondary detection using labeled avidin, streptavidin, captavidin, or neutravidin, the antibodies of the present invention can be labeled with biotin. When the antibodies of the present invention are used, e.g., for western blotting applications, they can usefully be labeled with radioisotopes, such as $^{33}$P, $^{32}$P, $^{35}$S, $^{3}$H, and $^{125}$I. As another example, when the antibodies of the present invention are used for radio-immunotherapy, the label can usefully be $^{3}$H, $^{228}$Th, $^{227}$Ac, $^{225}$Ac, $^{223}$Ra, $^{213}$Bi, $^{212}$Pb, $^{212}$Bi, $^{211}$At, $^{203}$Pb, $^{194}$Os, $^{188}$Re, $^{186}$Re, $^{153}$Sm, $^{149}$Tb, $^{131}$I, $^{125}$I, $^{111}$In, $^{105}$Rh, $^{99m}$Tc, $^{97}$Ru, $^{90}$Y, $^{90}$Sr, $^{88}$Y, $^{72}$Se, $^{67}$Cu, or $^{47}$Sc.

"Prognosis" refers to a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression-free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis and/or cancer progression in a patient susceptible to or diagnosed with a cancer. Prognosis also includes prediction of favorable responses to cancer treatments, such as a conventional cancer therapy. A good or bad prognosis may, for example, be assessed in terms of patient survival, likelihood of disease recurrence, disease metastasis, or disease progression. Patient survival, disease recurrence, and metastasis may for example be assessed in relation to a defined time point, e.g. at a given number of years after cancer surgery (e.g. surgery to remove one or more tumors) or after initial diagnosis. In one embodiment, a good or bad prognosis may be assessed in terms of overall survival, disease-free survival, or progression-free survival.

In one embodiment, the marker level is compared to a reference level representing the same marker. In certain aspects, the reference level may be a reference level of expression from non-cancerous tissue from the same subject. Alternatively, reference level may be a reference level of expression from a different subject or group of subjects. For example, the reference level of expression may be an expression level obtained from tissue of a subject or group of subjects without cancer, or an expression level obtained from non-cancerous tissue of a subject or group of subjects with cancer. The reference level may be a single value or may be a range of values. The reference level of expression can be determined using any method known to those of ordinary skill in the art. In some embodiments, the reference level is an average level of expression determined from a cohort of subjects with cancer. The reference level may also be depicted graphically as an area on a graph.

The reference level may comprise data obtained at the same time (e.g., in the same hybridization experiment) as the patient's individual data, or may be a stored value or set of values that can be stored on a computer or on computer-readable media. If the latter is used, new patient data for the selected marker(s), obtained from initial or follow-up samples, can be compared to the stored data for the same marker(s) without the need for additional control experiments.

A "biological sample" in terms of the invention means a sample of biological tissue or fluid. Examples of biological samples are sections of tissues, blood, blood fractions, plasma, serum, urine, or samples from other peripheral sources, such as cell cultures, cell colonies of even single cells, or a collection of single cells. Furthermore, also pools or mixtures of the above mentioned samples may be employed. A biological sample may be provided by removing a sample of cells from a subject, but can also be provided by using a previously isolated sample. For example, a tissue sample can be removed from a subject suspected of having a disease by conventional biopsy techniques. In a preferred embodiment, a blood sample is taken from the subject. In one embodiment, the blood or tissue sample is obtained from the subject prior to initiation of radiotherapy, chemotherapy, or other therapeutic treatment. According to the invention, the biological sample preferably is a blood or a serum sample. In certain aspects the sample is or comprises blood cells, e.g. erythrocytes, leukocytes, or thrombocytes.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

Figures 1A, 1B, 1C:
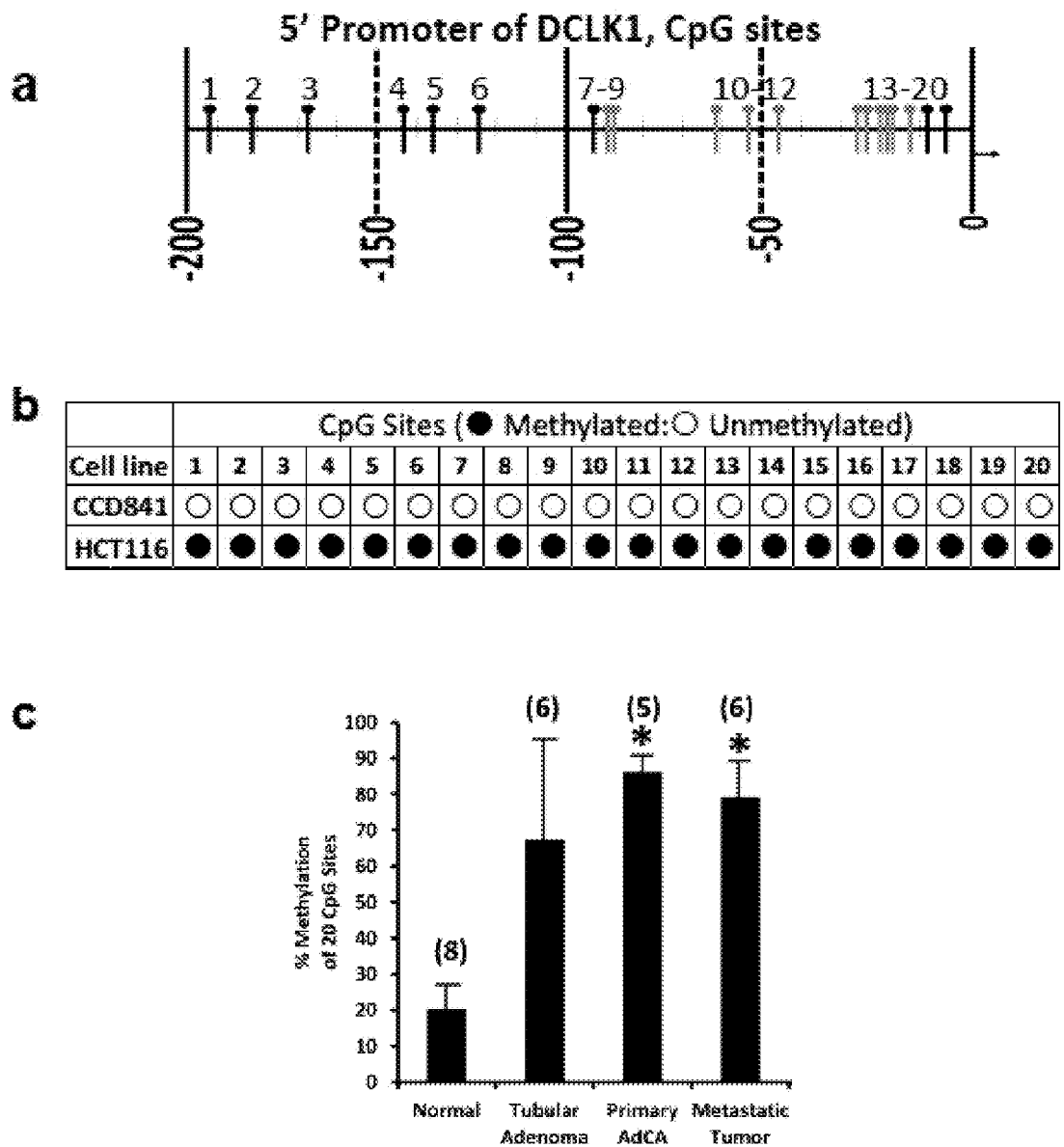
FIG. 1A-1C. Methylation of 5'(α)-promoter of hDCLK1. (α) CpG sites that can be potentially methylated within 200 bps of the 5'(α)-promoter of DCLK1-gene are depicted as vertical lines, and numbered 1-20. Vertical lines depict CpG sites used for assessing DNA methylation of 5'(α)-promoter of DCLK1-gene in a recent study (Vedeld et al., *Epigenetics*. 2014, 9(3):346-50). (b) Methylation status of 20 CpG sites was determined using the bisulfate method of sequencing as described in Methods. Methylation status of the 20 sites is shown for representative normal (CCD841) and colon cancer (HCT116) cell lines. Open circles indicate unmethylated CpG sites; filled circles indicate methylated CpG sites. (c)

Methylation status is presented as bar graphs, and represents % CpG sites methylated (of the 20 sites analyzed) in samples from normal colons (Normal), colonic tubular-adenomas (TAs), primary adenocarcinomas (AdCAs), and metastatic (MET) tumors. Each bar graph=mean±SEM of data from the indicated number of samples in parentheses, that were analyzed. *=$p<0.05$ vs methylation status of normal-colons that were obtained from patients free of adenomas and adenocarcinomas. The procurement of samples is described in methods.

FIG. 2A-2F. Western blot (WB) analysis of DCLK1 protein in human cell lines and patient samples. The molecular weight of the proteins correspond to the long (~80 KDa) and short (~45 KDa) DCLK1 protein in human cells. (a-f) Tissue samples were obtained from patients with either normal-colons (hNCs), free of Ads/AdCAs, or from patients with adenocarcinomas, as described in methods. Representative WB of samples from hNCs (a) and hCRCs (c) are presented, demonstrating relative expression of L/S DCLK1; laboratory numbers for patient samples are indicated above the Blots in a and c. WBs in each case were densitometrically analyzed and ratio of relative levels of L/S DCLK1 to corresponding β-actin levels are presented as bar-graphs, from all samples analyzed (b, normal-colons; d, adenocarcinomas). Each bar-graph in b and c=mean±SEM of calculated ratios for the two isoforms in patient samples obtained from 8-22 patients, as described in methods. (e) Representative Western blots from normal (CCD841) and colon cancer (HCT116) cell lines. (f) Representative WBs from isogenic HEKC/HEKmGAS cells.

FIG. 3A-3H. RT-PCR analysis of long and short transcripts of DCLK1 in human and mouse cell lines and in patient samples. (a) Diagrammatic representation of hDCLK1 gene with transcription of DCLK1-L/S transcripts from the indicated exons (see FIG. 10 for details). The α promoter for DCLK1-L is located at 5'-end and the alternate β promoter for DCLK1-S is located within IntronV of the gene. Transcriptional start sites (ATG) and end sites (TGA) are shown and homologous sequences between the two transcripts are shaded. Numbered boxes=exons; lines between boxes=introns. (b-h) Samples from mice and humans (patients) were obtained as described in methods and processed for RT-PCR using human/mouse primers for DCLK1-L/S transcripts. Representative RT-PCR data are shown from: human cell lines (b,c); Normal-colonic-mucosa and brain tissues from wild type FVB/N mice (d); uninvolved mouse colon-mucosa (Norm) and mouse colon-tumor samples (Ads) (e); mouse cancer cell line (CT26) (f). Human (b,c) and mouse (d-f) β-actin was run as internal controls. The molecular weight (MW) in terms of bps is shown on left-hand side of each image in b-f. Representative RT-PCR data from patient samples are presented in FIG. 15. Relative levels of short (g) and long (h) DCLK1 transcripts in human patient samples are presented as a ratio of the corresponding β-actin levels; hNC samples=Norm, tubular-adenomas=TA and colon-adenocarcinomas=AdCAs. Each bar-graph in g and h=mean±SEM of 5-8 separate patient samples, analyzed in duplicate.

FIG. 4A-4E. Primer extension analysis for confirming transcription of DCLK1-L/S transcripts. (a) Schematic representation of 3'-5' primer-extension analysis. The shaded portion shows 100% homology in the sequences between the two isoforms. A common primer-2 from the two transcripts was used for 3'-5' extension, followed by ligating with non-mammalian adapter sequence (black box), as described in methods. Primers 1 and 2 were used for PCR amplification of the products. (b-c) Both nascent mRNA and total RNA were used for primer extension analysis, followed by PCR amplification, as described above. Resulting PCR products are presented in b (HCT116 cells) and c (HEK-293 cells). HCT116 cells were positive for only the short transcript (498 bps) and HEK-293 cells were positive for only the long transcript (1,300 bps). All other bands were either non-specific or fragments thereof, as confirmed by sequencing. (d-e) Confirmation of epigenetic silencing of 5'(α)-promoter of DCLK1-gene in HCT116 cells. Relative expression (RT-PCR) of L/S DCLK1 in HCT116 cells, in presence or absence of treatment with 5-aza-2'-deoxycytidine (5-azacytidine) is shown. (d) Representative RT-PCR data; (e) densitometric data presented as % of β-actin in corresponding samples. Each bar-graph in e=mean±SEM of three experiments.

FIG. 5A-5E. Role of TCF4/LEF binding-sites in activation of 5'(α)-promoter. (a) In silico analysis of ~3 kb of 5'(α)-promoter (transcribing DCLK1-L), identified several binding sites for TCF-4/LEF and NF-κB, with >90% conserved sequences. The construct (DCLK1-L-LUC) used for the promoter-reporter assays is diagrammatically shown below the mapped promoter. (b-e) Relative transcriptional/luciferase activity (RLU) in the indicated cells, transiently-transfected with the plasmids for 48 hours, in the presence or absence of transfection with either PG expressing plasmid (p-mGAS) (c), or the indicated siRNA (d,e), as shown. Cells were co-transfected with promoter-reporter construct±p-mGAS/siRNA. VEC=control LUC vector; TOP=TOPFlash plasmid with wild type TCF4/LEF binding sites for β-catenin binding; FOP=mutant FOPFlash plasmid. Each bar-graph in b-e represents mean±SEM of three separate experiments conducted in triplicate/experiment. *=$p<0.05$ vs corresponding values with control vector. † in b=$p<0.05$ vs corresponding values in HEKC cells; † in c=$p<0.05$ vs corresponding values with DCLK1-L-LUC vector alone. † in d and e=$p<0.05$ vs control siRNA values.

FIG. 6A-6G. In situ binding of endogenous β-catenin to the two functional TCF4/LEF binding sites in the 5'(α)-promoter of DCLK1-gene. (a) Map of functional TCF4/LEF binding sites in 5'(α)-promoter of DCLK1-gene, as determined by ChIP analysis for β-catenin binding. (b-d) Relative binding of β-catenin to the indicated TCF4/LEF binding sites in the indicated cell lines, by ChIP analysis. Total level of β-catenin in the samples is presented as input. (e-f) Relative binding of β-catenin to functional TCF4/LEF binding sites in HEK-293 cells, transfected with either control vector (e) or PG expressing (p-mGAS) vectors (f), 48 hours before ChIP. Data presented in b-f is representative of six observations from three experiments. (g) Relative binding of β-catenin, in situ, to functional binding sites in 5'(α)-promoter of DCLK1-gene, in different cell-lines, in presence or absence of mPG expression (described above), presented as % of input. Each bar-graph=mean±SEM of duplicates from three experiments. % binding of β-catenin was determined by densitometric analysis of indicated bands.

FIG. 7A-7E. Role of NF-κB binding site in activation of IntronV(β)-promoter of DCLK1 gene. (a) In silico analysis of IntronV(β)-promoter demonstrated presence of a consensus TATA box and a consensus NF-κB binding site, as shown. IntronV(β)-promoter-luciferase constructs, used in the current studies, are diagrammatically shown as DCLK1-S-LUC-1 and DCLK1-S-LUC-2. (b-e) Transcriptional activity of promoter-reporter constructs in the indicated cell lines (b), in the presence or absence of PG expression (c) or treatment with either control or NF-κBp65-siRNA (d-e), as described in the legend of FIG. 5. Transcriptional activation in terms of luminescence (RLU) is presented in b-e. Each bar-graph=mean±SEM of data from three experiments, conducted in triplicate. *=p<0.05 vs control vector in (b-e). † in (c)=p<0.05 vs LUC-1 or LUC-2 vector alone, in the absence of PG expression. † in (d,e)=p<0.05 vs corresponding data with control siRNA treated samples.

FIG. 8A-8F. Binding of endogenous activated NF-κBp65 to the single NF-κB binding site in the IntronV(β)-promoter, in situ, in human cell lines. (a) In silico analysis of IntronV (β)-promoter DNA, mapped a conserved NF-κB binding site within 500 bps of TATA box. (b,c) ChIP analysis, demonstrating relative binding of NF-κBp65 to the single NF-κB binding site in the indicated cell lines. (d) Relative levels of NF-κBp65 bound to NF-κB binding site was calculated as % of input by densitometric analysis of the bands from all experiments and are presented as bar-graphs for the indicated cell lines. (e) Relative binding of NF-κBp65 to the single NF-κB binding site, in the presence or absence of PG expression (p-mGAS), was measured by ChIP analysis, as described in the legend of FIG. 6. (f) Relative levels of NF-κBp65 bound to the NF-κB binding site in HEK-293 cells, in the presence of PG expression, is presented as % of input, by densitometric analysis of the bands. (b,c,e) representative ChIP data from one of three experiments. Each bar-graph in (d,f)=mean±SEM of data from three experiments, run in duplicate.

Figures 9A, 9B, 9C:
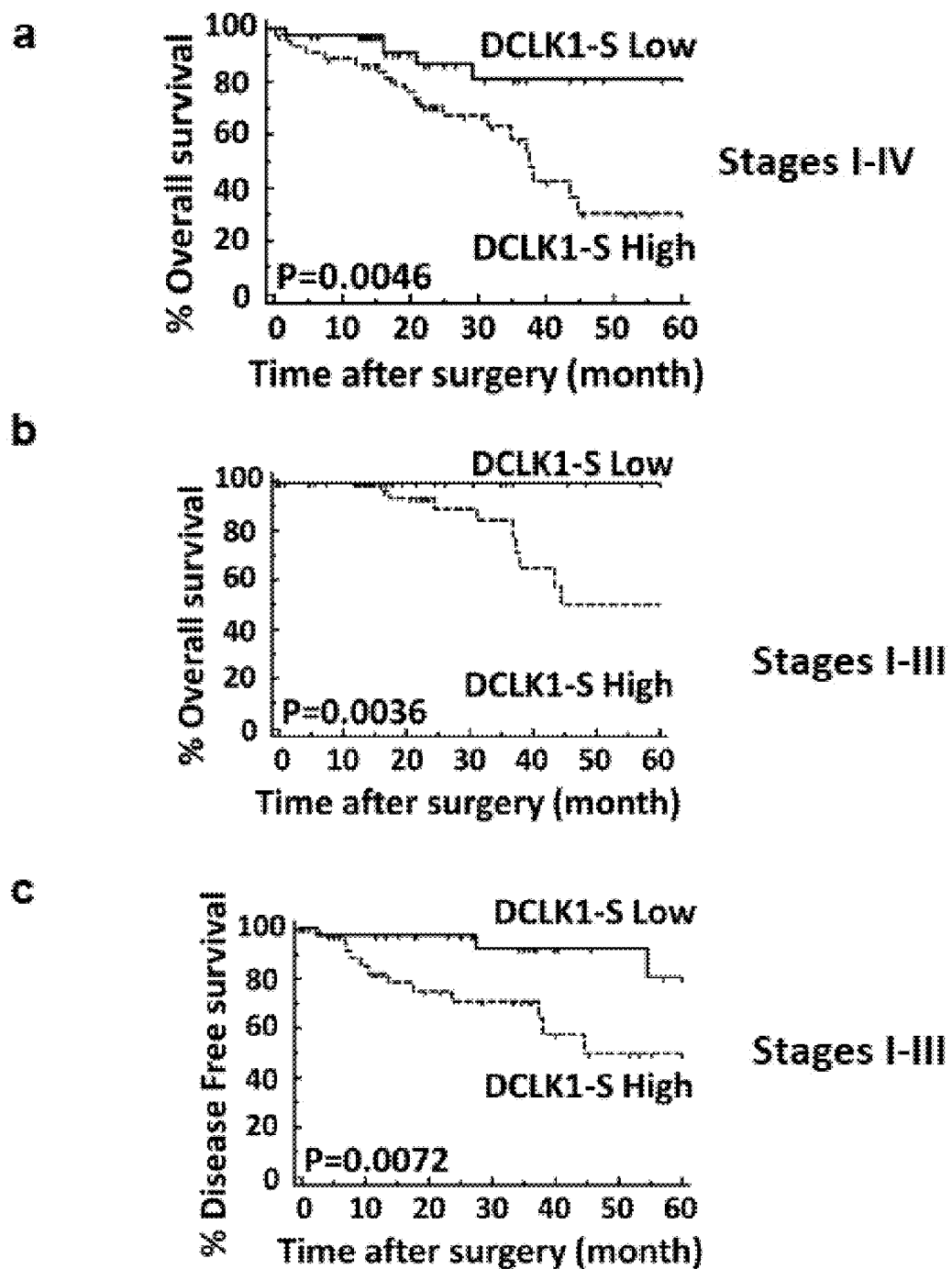

FIG. 9A-9C. Overall survival and disease free survival of patients with CRC, in relation to low or high expression of DCLK1-S. (a) Kaplan-Meier overall survival curves of CRC patients, with stages I-IV disease in relation to relative expression levels of DCLK1-S measured by qRT-PCR, n=92 patients. (b) Kaplan-Meier overall survival curves of CRC patients with stages I-III disease, in relation to relative expression levels of DCLK1-S measured by qRT-PCR n=71 patients. (c) Kaplan-Meier disease free survival curves of CRC patients with stages I-III disease, in relation to relative expression levels of DCLK1-S measured by qRT-PCR, n=67 patients. The cutoff threshold values were defined by using the median values of DCLK1-S expression of each cohort in cancer tissues.

Figures 3A, 3B, 3C, 3D, 3E, 3F, 3G, 3H:
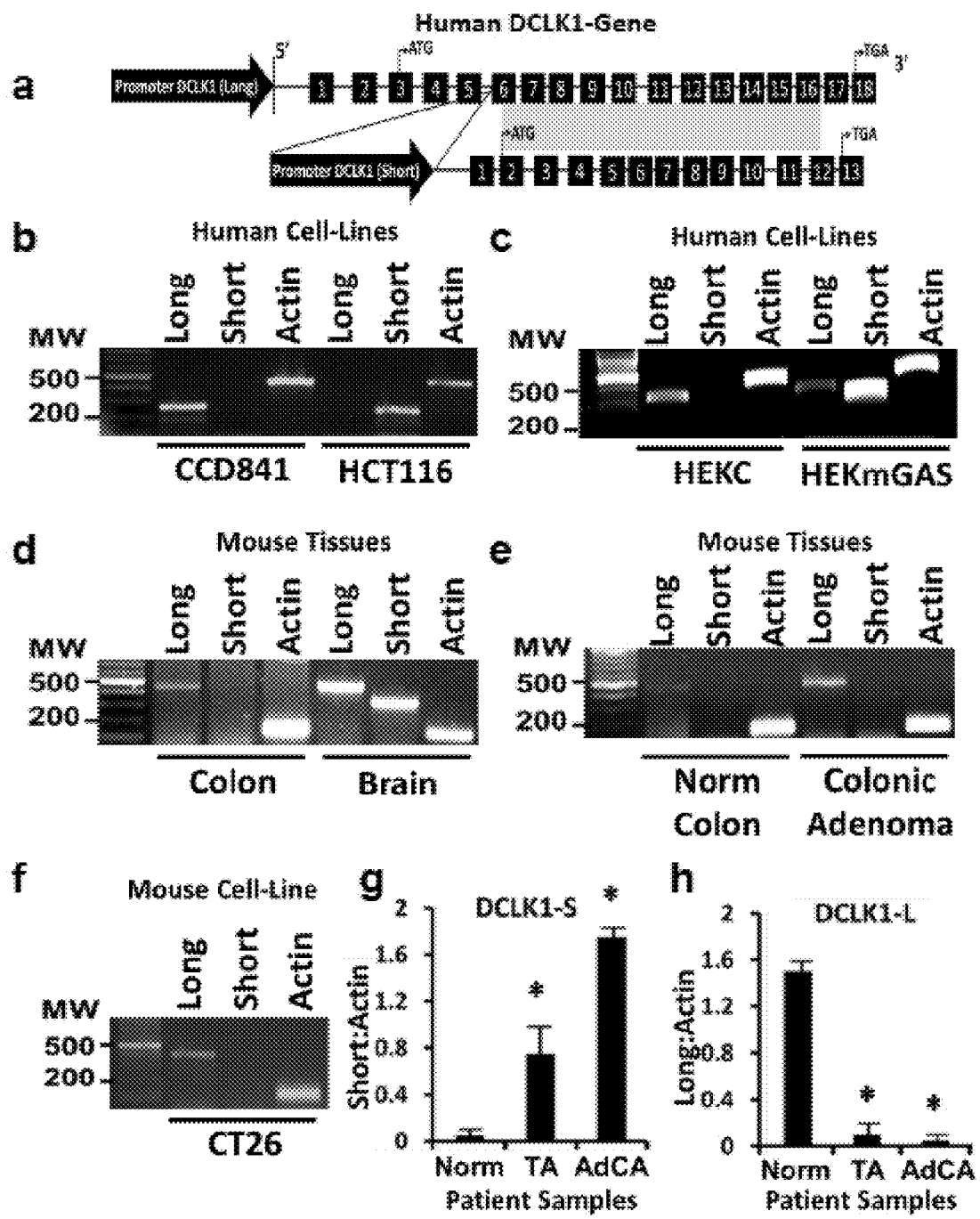
Figure 10:
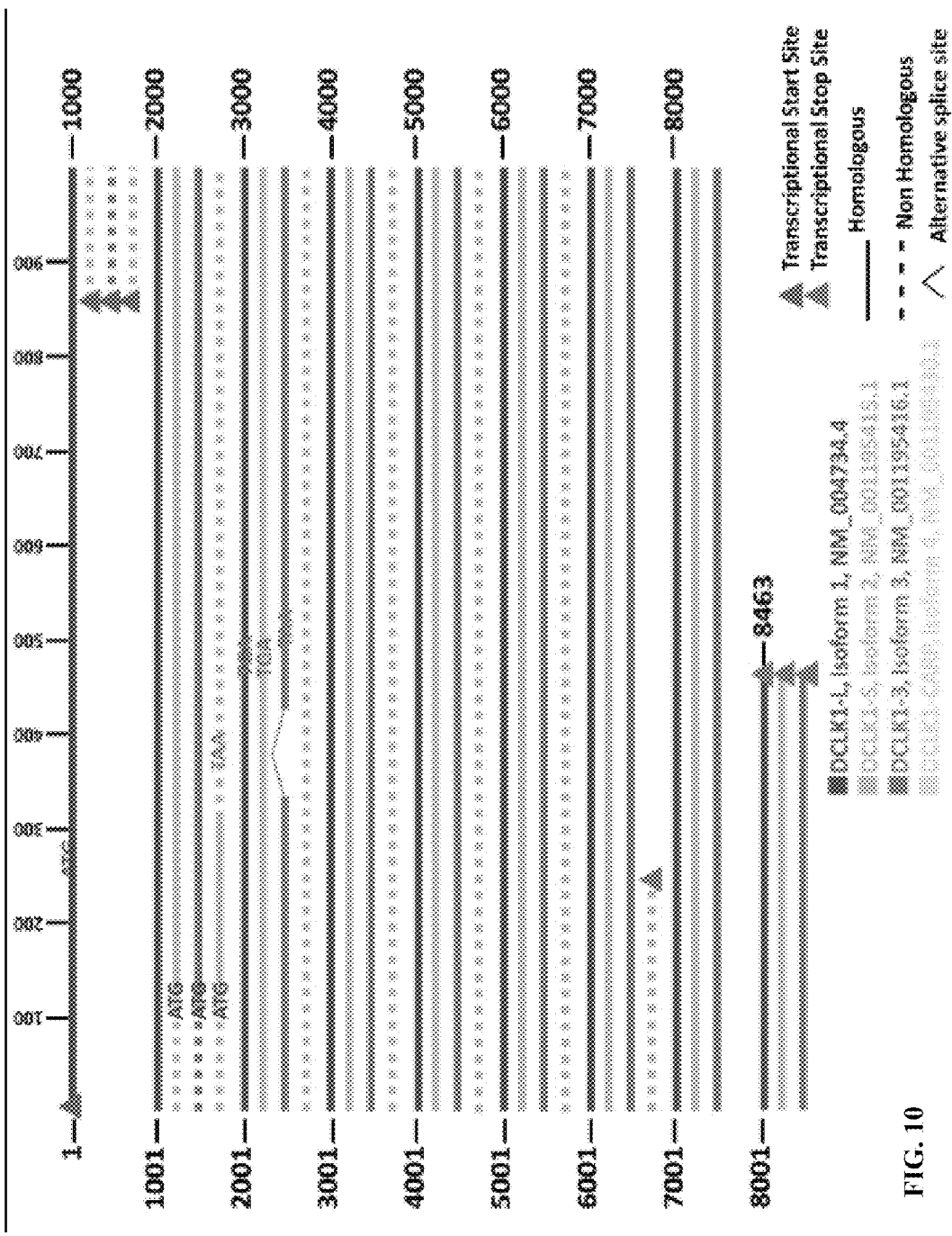

FIG. 10. Homology between the nucleotide sequence between 4 isoforms of human DCLK1 in NCBI data base. Nucleotide sequence homology between the transcripts for the 4 isoforms of human DCLK1. Diagrammatic representation of the nucleotide sequence homology of isoforms 1, 2, 3, 4 of hDCLK1 (formerly known as DCAMKL1), as described in the NCBI database. Isoform 1 (NM_004734.4), isoform 2 (NM_001195415.1), isoform 3 (NM_001195416.1), and isoform 4 (NM_001195430.1). Solid lines=homologous regions, dashed lines=non-homologous regions, arrow head=alternative splice site, triangles=transcriptional start sites or transcriptional stop sites. Start and stop codons are indicated. The coding region of DCLK1 isoform 1 (arbitrarily termed long isoform, DCLK1-L) starts at by 284 (from exon 2, as shown in FIG. 3A) and ends at by 2473 (exon 18). The 5' untranslated region includes exon 1 and part of exon 2, downstream of 5'(α)-promoter as shown in FIG. 3A. The 3' untranslated region includes most of exon 18 (3301 bp). The coding region of DCLK1 isoform 2 (arbitrarily termed short isoform, DCLK1-S) starts at base 334 (of exon 1, 3' of IntronV, as shown in FIG. 3A), and ends at base 1602 (in exon 14, as shown in FIG. 3A). Isoform 2 consists of 14 exons. The 5' untranslated region includes most of exon 1 (352 bp) and 3' untranslated region includes most of exon 14 (3301 bp). The coding region of DCLK1 isoform 3 (DCLK1-3) starts at base 334 (in exon 1, 3' of IntronV) and ends at base 1635 (exon 14). Isoform 3 is transcribed from 13 exons rather than 14 exons. Isoforms 2 and 3 represent splice variants of transcripts originating in the same exon of the gene that are different by 74 bps, since isoform 2 contains sequences that are transcribed from an additional exon compared to isoform 3 (Sossey-Alaoui et al., *Genomics.* 1999, 56(1):121-6). The coding region of DCLK1 isoform 4 (DCLK1-Carp) starts at base 334 and ends at base 504, and is transcribed from 4 exons. The 5' untranslated region is homologous between isoforms 2, 3, and 4. The 3' untranslated region of isoform 4 includes most of exon 4. Isoform 1 (DCLK1-L) and isoform 2 (DCLK1-S) share 7200 bps, and were the only two transcripts that were detected in normal colons and colon cancer cells. The 5' UTR of L and S transcripts were non-homologous and at least 17 bps of the S-transcript, from the ATG site, was also non-homologous; primers were thus designed from this non-homologous region to detect DCLK1-S transcripts, and the specific sense and anti-sense primers used for detecting either the L isoform or the S isoform are presented in Table 4. Sense and anti-sense primers were similarly designed from non-homologous sequences of the transcripts, to distinguish between isoforms 2, 3, and 4, and it was confirmed that normal and cancer cells examined in this study were positive for only isoforms 1 and 2, which have been arbitrarily termed long (L) and short (S) isoforms of DCLK1, for the purpose of these studies.

Figure 11A:
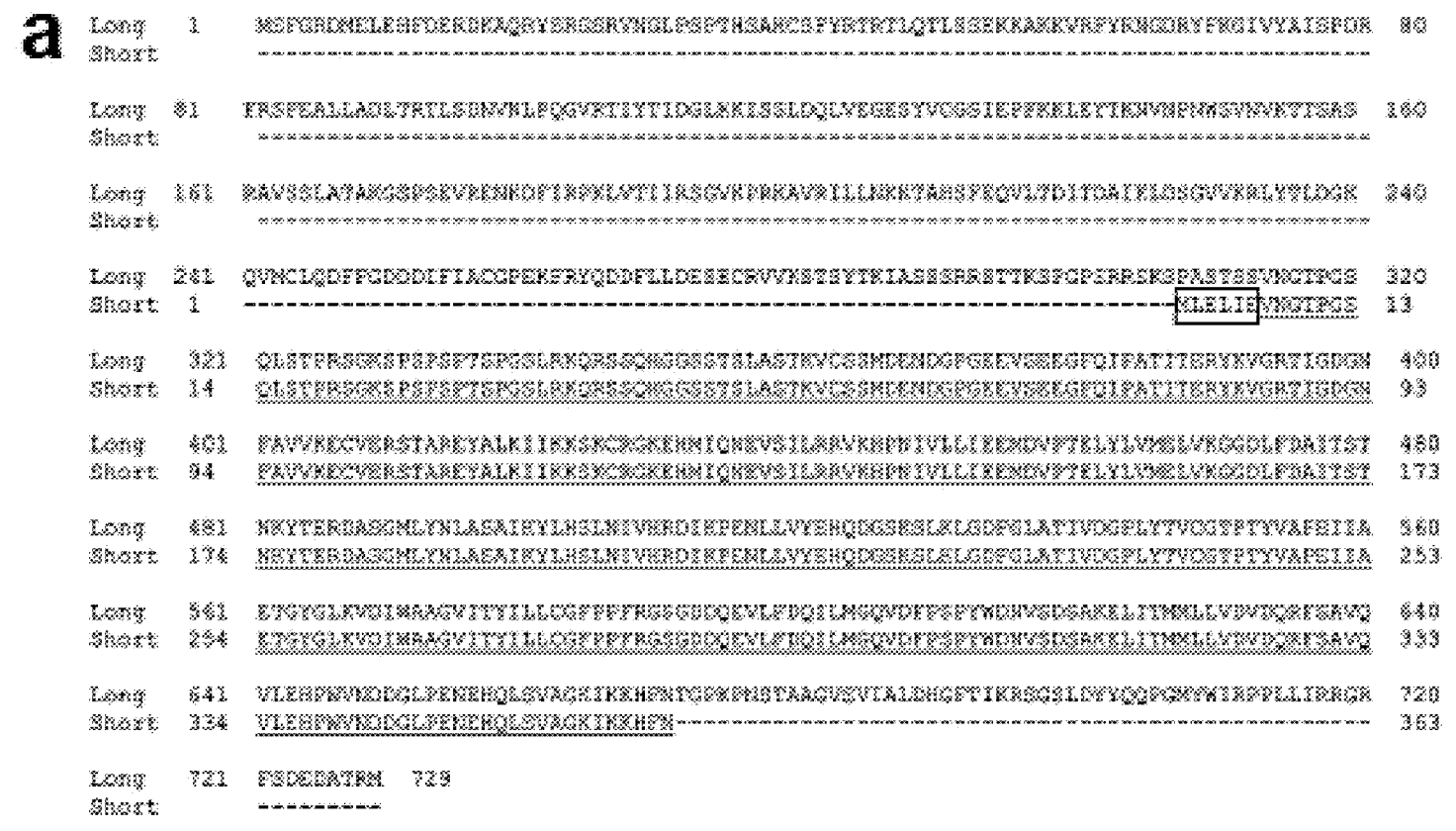
Figure 11B:
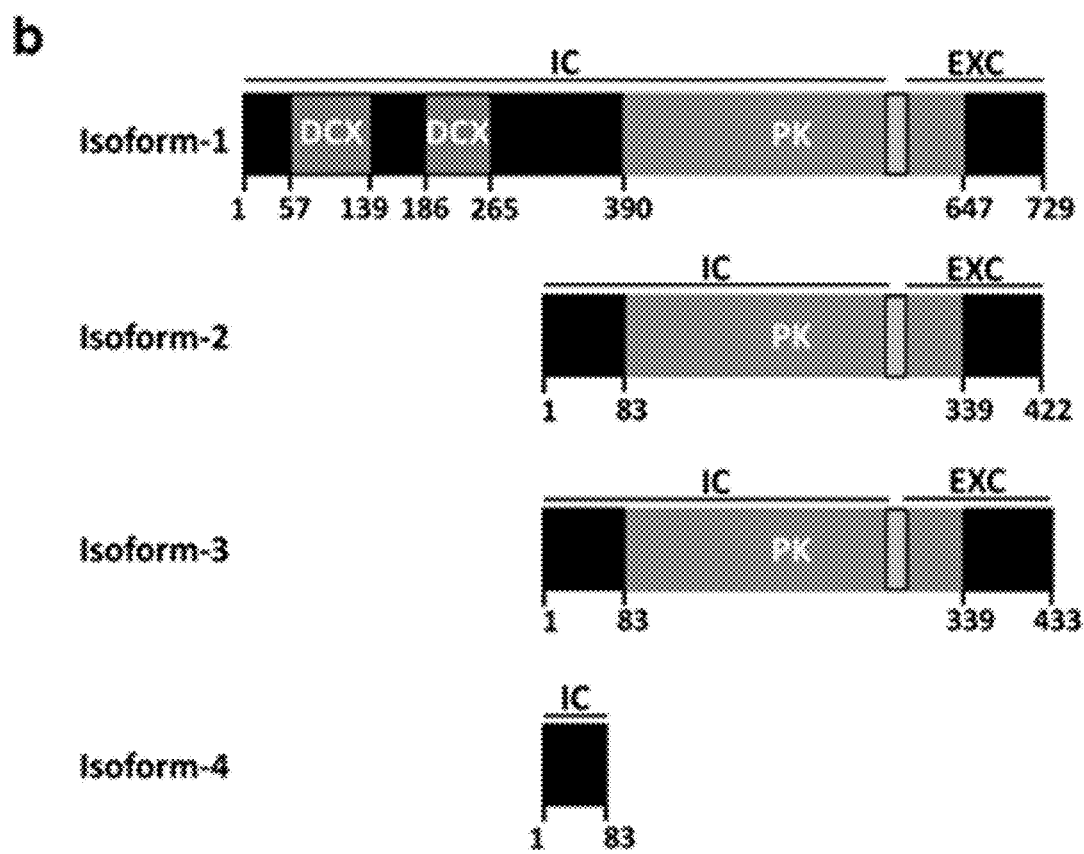

FIG. 11A-11B. (a) Homology between the amino-acid sequence of isoforms 1 (DCLK1-L) and 2 (DCLK1-S); (b) diagrammatic representation of protein domains in the 4 isoforms of hDCLK1. (a) Homology between the amino-acid sequence of isoforms 1 (DCLK1-L) and 2 (DCLK1-S). Amino-acid sequences of the two L/S isoforms have been aligned, and homologous sequences are underlined. Only a few amino acids in the S isoform were different and have been boxed. Dashed line depicts absence of corresponding amino acids in S isoform compared to the L isoform. (b) diagrammatic representation of protein domains in the 4 isoforms of hDCLK1. DCX=doublecortin domain; PK=calmodulin-like protein kinase domain; IC=intracellular domains of the indicated isoforms; EC=extracellular domain of the four isoforms; Isoforms are named according to the NCBI database. The total number of amino acids in the four isoforms, as it relates to the various domains is indicated. Briefly, isoform (DCLK1-L) consists of two doublecortin domains, a protein kinase domain, and a serine/proline rich area. The transmembrane domain was present only in isoforms 1, 2 and 3. Protein analysis using PSORT (available on the web at psort.nibb.ac.jp.org, University of Tokyo, Japan) suggested only one transmembrane domain (located between 568-584 AAs of isoform 1); labeled as DCLK1-L in the current studies). However, protein analysis using BCM Search Launcher (available on the web at searchlauncher.bcm.tmc.edu/multi-align/multi-align.html, Baylor College of Medicine, Houston, Tex.) identified 2 transmembrane domains (located between AA 534-559 and 568-585). Isoforms 2 and 3 retain the protein kinase domain but lack the doublecortin domains, compared to isoform 1. Isoform 4 lacks both the doublecortin domains and the protein kinase domain. Note that SwissProt describes a 740 AA isoform (015075-1) that is not described in the NCBI database. This 740 AA protein consist of two doublecortin domains, a protein kinase domain, and a serine/proline rich area. Isoform 1 (NP_004725.1) has been previously referred to as DCLK1-long-B (Engels et al., *Brain Res Mol Brain Res.* 2004, 120(2):103-14), KIAA0369AS (Omori et al., *J Hum Genet.* 1998, 43(3):169-77), DCK-α1 (Pal et al., *Genome Res.* 2011, 21(8):1260-72), and DCLK1β (Burgess and Reiner, *J Biol Chem.* 2002, 277(20):17696-

705). Isoform 2 (NP_001182344.1) has been previously referred to as DCLK1-short-B (Engels et al., *Brain Res Mol Brain Res.* 2004, 120(2):103-14), DCK-β1 (Shang et al., *Biochemistry.* 2003, 42(7):2185-94), and KIAA0369-BS (Omori et al., *J Hum Genet.* 1998, 43(3):169-77). Isoform 3 (NP_001182345.1) has been previously referred to as DCLK1-short-A (Engels et al., *Brain Res Mol Brain Res.* 2004, 120(2):103-14), DCK-02 (Shang et al., *Biochemistry.* 2003, 42(7):2185-94), KIAA0369-BL (Omori et al., *J Hum Genet.* 1998, 43(3):169-77), and CPG16 (Burgess and Reiner, *J Biol Chem.* 2002, 277(20):17696-705; Silverman et al., *J Biol Chem.* 1999, 274(5):2631-6). Isoform 4 has been previously referred to as ania-4 (Berke et al., *J Neurosci.* 1998, 18(14):5301-10) and CARP (Vreugdenhil et al., *J Neurobiol.* 1999, 39(1):41-50). The 740 AA protein described in the SwissProt database (015075-1) has been referred to as DCLK1-long-A (Engels et al., *Brain Res Mol Brain Res.* 2004, 120(2):103-14), KIAA0369-AL (Omori et al., *J Hum Genet.* 1998, 43(3):169-77), DCK-α2 (Shang et al., *Biochemistry.* 2003, 42(7):2185-94), and DCLK α (Burgess and Reiner, *J Biol Chem.* 2002, 277(20):17696-705). Most investigators in this field have been using commercially available antibodies which were generated against a peptide sequence between 700-729 bp of isoform 1 (DCLK1-L), which is homologous to C-terminal end of isoform 2 (DCLK1-S), but is not homologous to isoforms 3 and 4. Since it is now known the normal and cancer epithelial cells, examined here, only express isoforms 1 (L) and 2 (S), commercially available antibodies can be used to detect these isoforms, which differ in molecular mass: L=~82 kDa; S=~47 kDa.

Figures 12A, 12B:
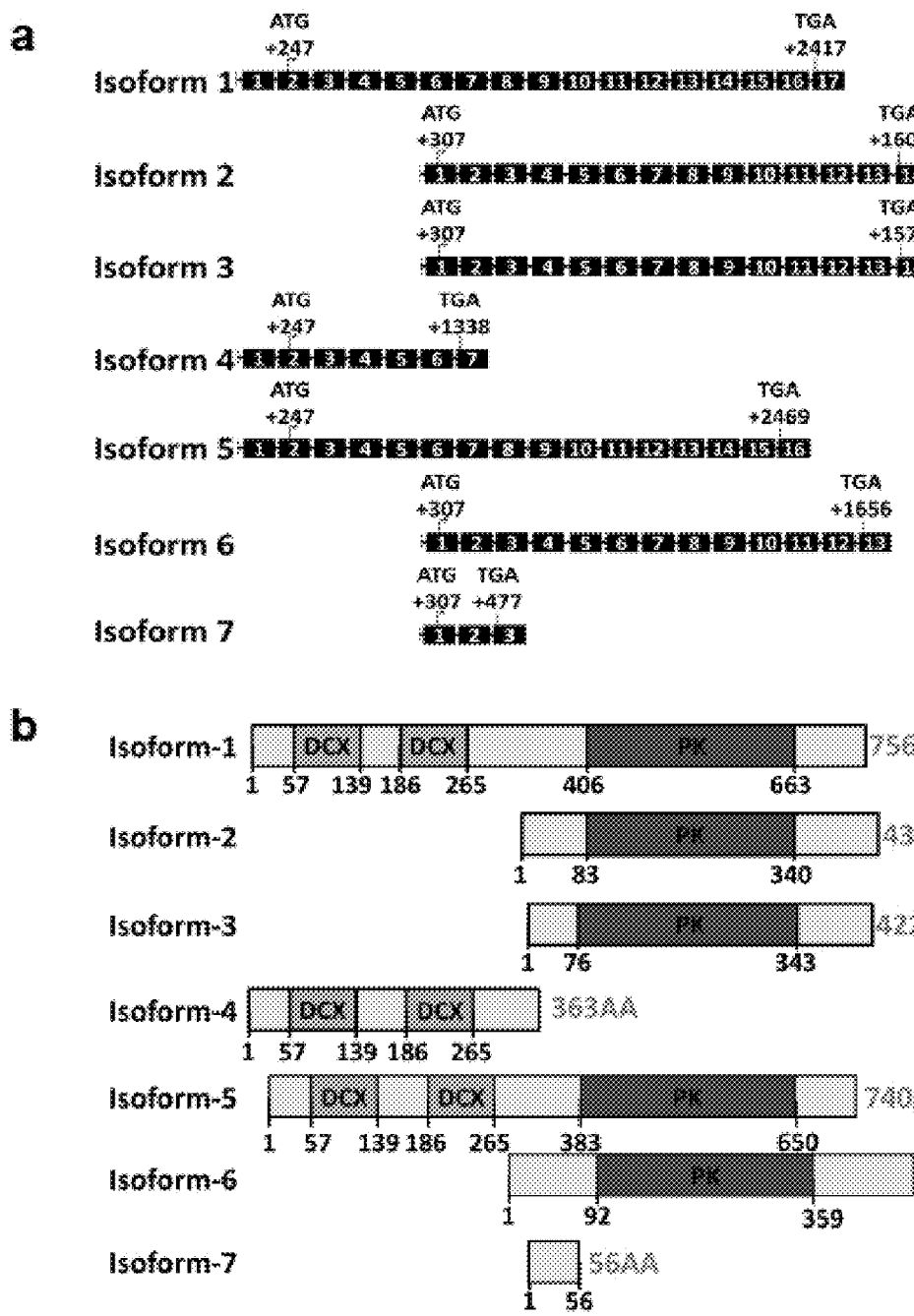
Figures 14A, 14B, 14C, 14D, 14E:
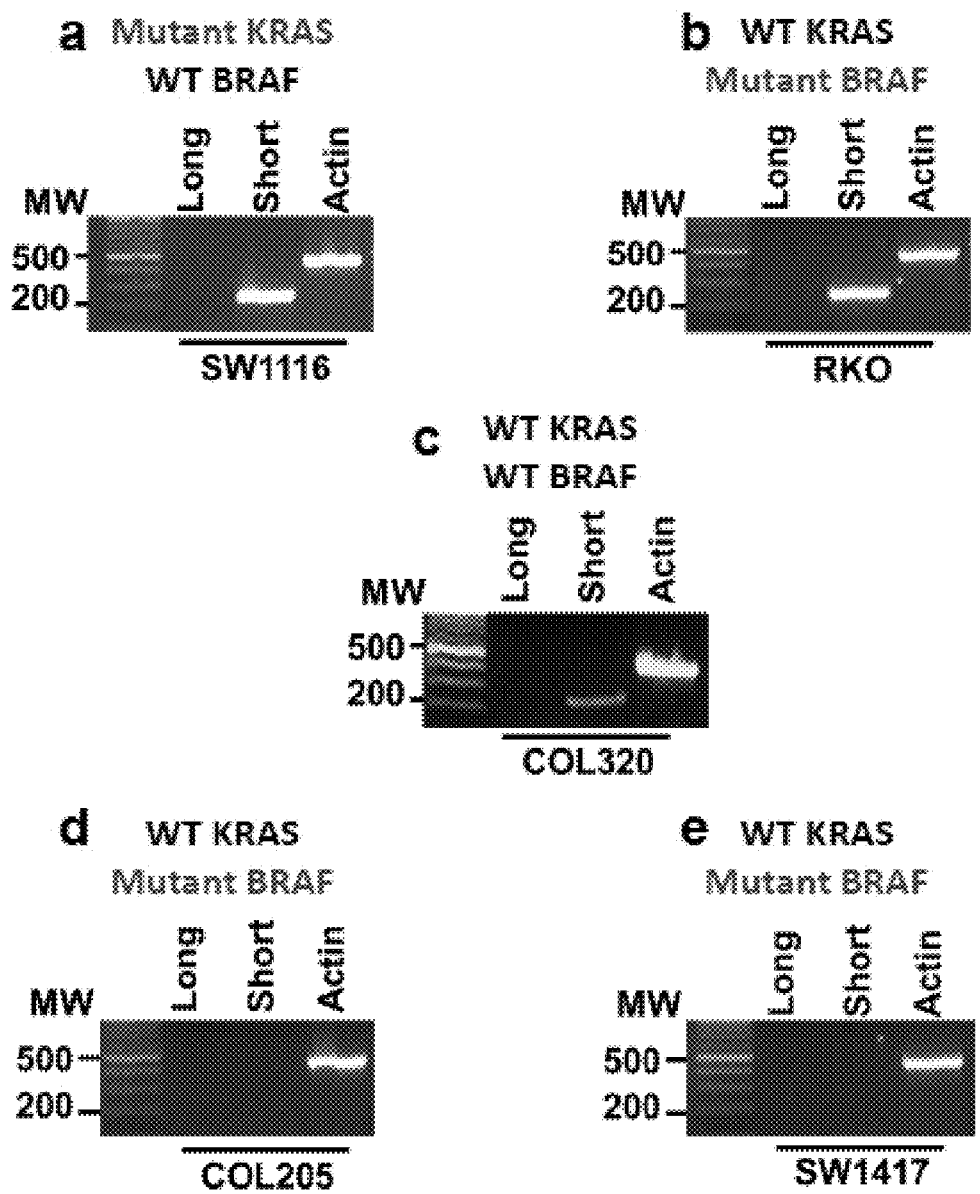

FIG. 12A-12B. Diagrammatic representation of the various mouse isoforms of Dclk1 at the genetic (a) and protein (b) levels. (a) Diagrammatic representation of the transcripts for the 7 mouse isoforms of Dclk1. Isoform 1 (NM_019978.3), Isoform 2 (NM_001111051.1), Isoform 3 (NM_001111052.1), Isoform 4 (NM_001111053.1), Isoform 5 (NM_001195538.1), Isoform 6 (NM_001195539.1), and Isoform 7 (NM_001195540.1). Transcriptional start sites (ATG) and end sites (TGA) are shown. Numbered boxes=exons; lines between boxes=introns. Introns and Exons are not drawn to scale. Promoter for isoforms 1, 4, 5 is located at 5'-end and promoter for isoforms 2, 3, 6, 7 is located within IntronV of the gene. Dclk1-L mouse primers utilized throughout our study recognize isoforms 1, 4, and 5. Dclk1-S mouse primers utilized by us recognizes isoforms 2, 3, 6 and 7, and was confirmed to detect the short mouse transcript(s) in the mouse brain as shown in FIG. 3d. (b) Diagrammatic representation of the protein domains present in the 7 isoforms of mouse Dclk1. DCX=doublecortin domain; PK=calmodulin-like protein kinase domain. The total number of amino acids in the seven isoforms, as it relates to the various domains is indicated. Briefly, isoform 1 consists of two doublecortin domains and a protein kinase domain. Isoforms 2 and 3 retain the protein kinase domain but lack the doublecortin domains, compared to isoform 1. Isoform 4 retains the doublecortin domains but lacks the protein kinase domain. Isoform 5, like, isoform 1, consists of two doublecortin domains and a protein kinase domain. Isoform 6 lacks the doublecortin domains and consists of a protein kinase domain. Isoform 7 lacks both the doublecortin and protein kinase domains.

Figure 13:
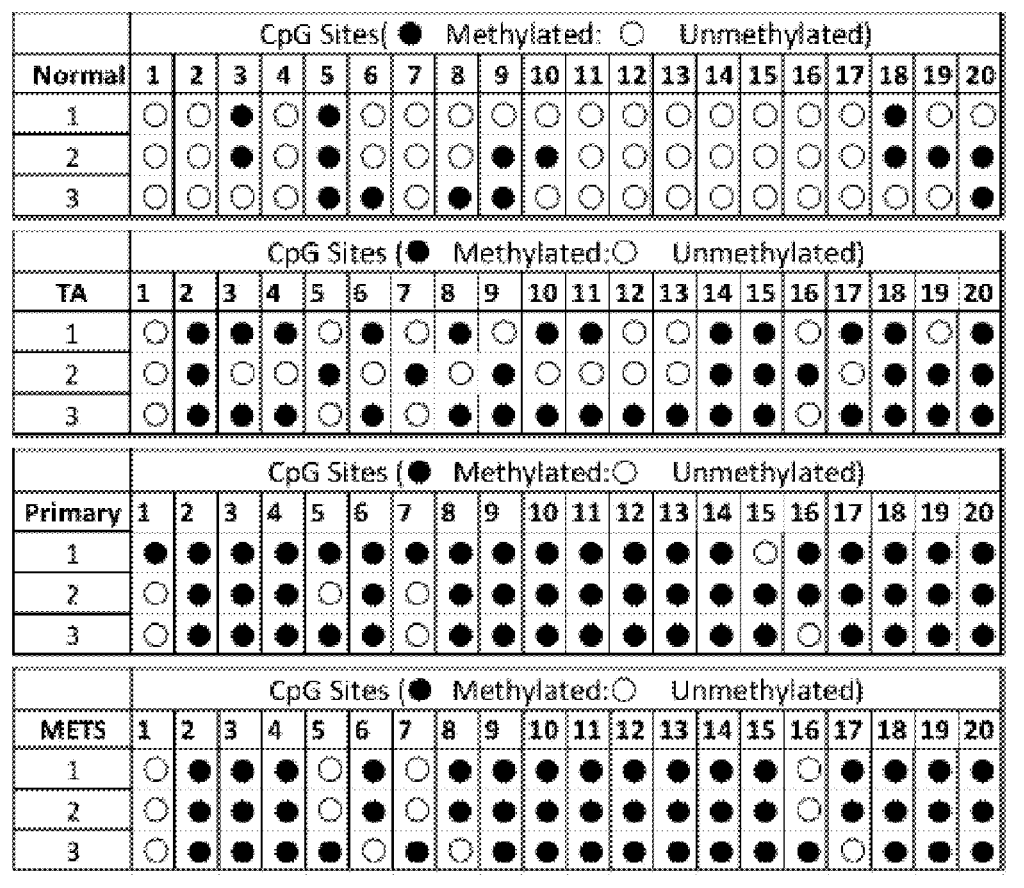

FIG. 13. DNA methylation analysis of 5'(α)-promoter of hDCLK1 in human samples. Methylation status of all twenty CpG sites in representative normal, tubular adenoma (TA), primary tumors (primary), and metastatic tumors (METS) is presented. Open circles=unmethylated CpG sites; filled circles=methylated CpG sites. The procurement of all the samples has been described in the methods below.

FIG. 14A-14E. Representative RT-PCR analysis of long and short transcripts of DCLK1 in human colon cancer (hCCC) cell lines. Representative RT-PCR data are shown from: hCCC cell lines (a-e); β-actin was run as internal controls. The molecular weight (MW) in terms of bps is shown on left-hand side of each image.

Figures 15A, 15B:
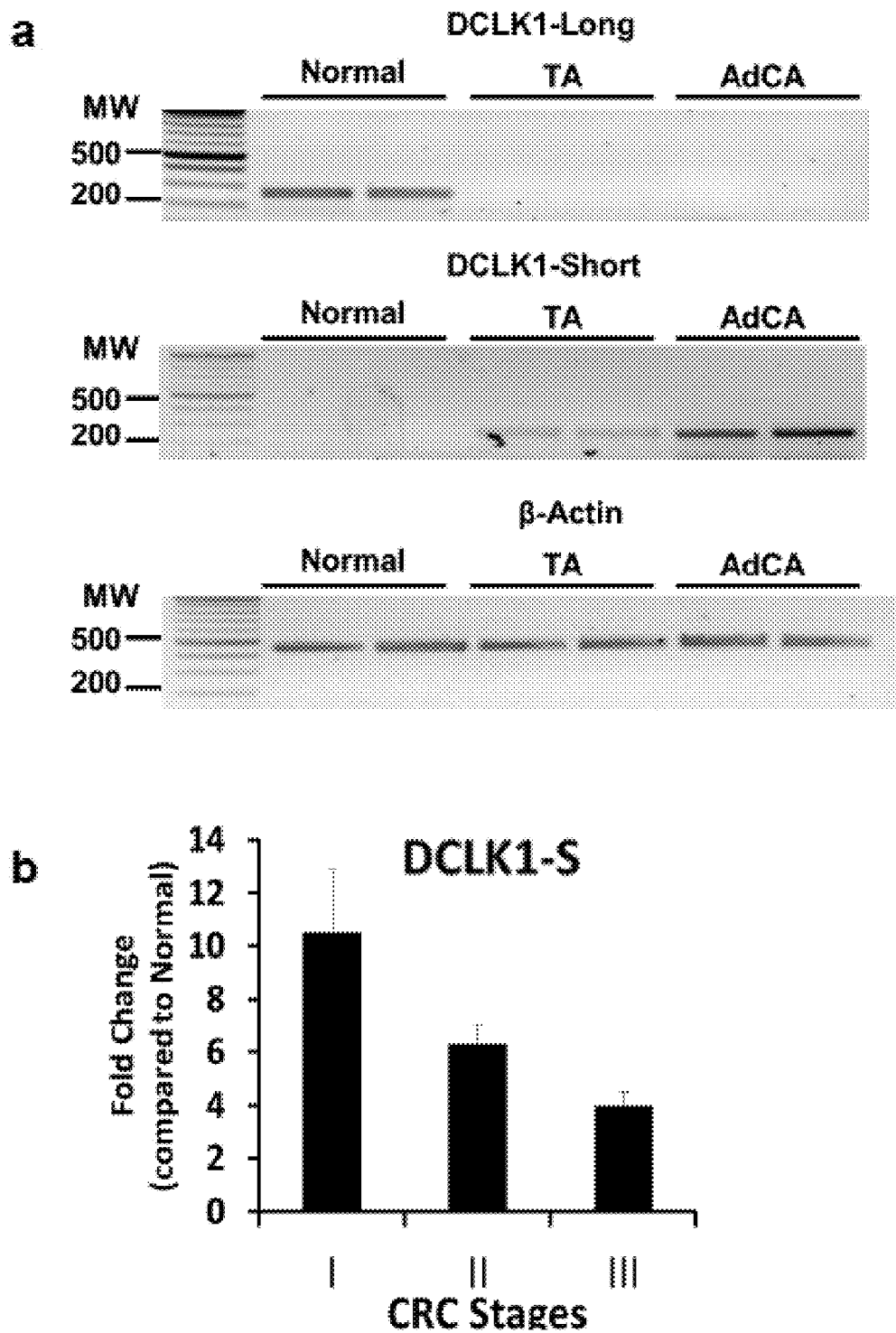

FIG. 15A-15B. Relative expression levels of long and short transcripts of DCLK1-isoforms in patient samples. Total RNA from indicated tissue samples were amplified by RT-PCR by using sense and anti-sense primers for amplifying either DCLK1-L transcripts or DCLK1-S transcripts, as described below. Representative data are presented from normal colons, tubular adenomas (TA) and advanced adenocarcinomas (AdCAs), obtained from two patients each; the samples were co-amplified and co-run at the same time for L/S transcripts and corresponding β-actin levels. Densitometric data from all samples that were similarly analyzed are presented as a ratio of β-actin levels in the corresponding samples, and are presented as bar-graphs in FIGS. 3G and 3H.

FIG. 16A-16D. Role of NFκB binding site in activation of the 5'(α)-promoter of DCLK1. (a) In silico analysis of ~5 kb of 5'-promoter of human DCLK1-gene (transcribing DCLK1-L), identified several binding sites for TCF-4/LEF and three NFκB binding sites, with >90% conserved sequences. (b) Relative transcriptional/luciferase activity (RLU) in the indicated cells, transiently-transfected with the plasmids for 48 hrs, in the presence or absence of transfection with either control or NFκBp65-siRNA. Cells were co-transfected with promoter-reporter construct±siRNA. VEC=control LUC vector. Each bar represents mean±SEM of four experiments. (c) Western-Blot analysis, demonstrating efficacy of NF-κBp65-siRNA for down-regulating the expression of NF-κBp65 protein in the cell lines. (d) Representative RT-PCR data for DCLK1-L isoform from indicated cells, in the presence of absence of either control-siRNA or NFκBp65-siRNA. The indicated cell lines were transfected with either (scrambled) siRNA (con-siRNA) or target-specific NF-κBp65-siRNA for 48 hrs, before processing the cells by RT-PCR.

Figures 17A, 17B:
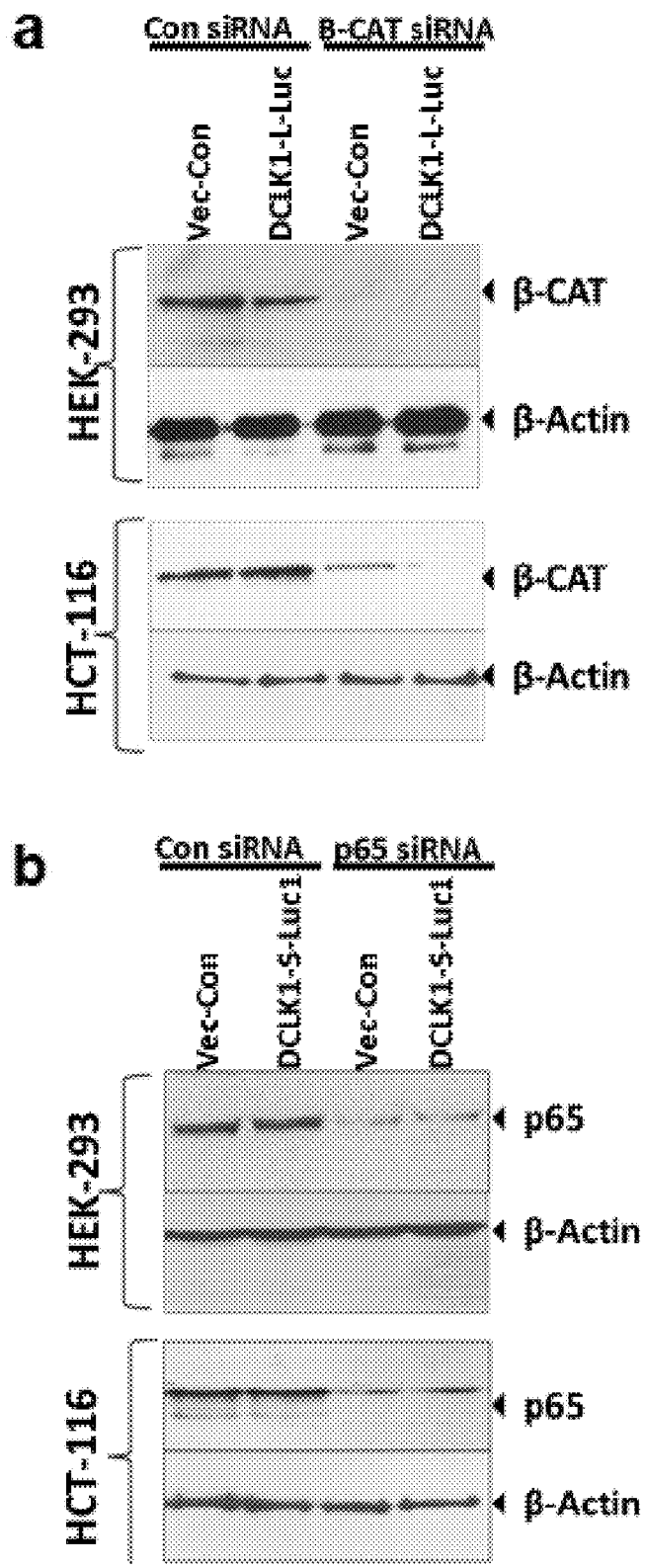

FIG. 17A-17B. Western blot analysis, demonstrating efficacy of β-catenin-siRNA and NF-κBp65-siRNA for down regulating the expression of the corresponding protein in the cell lines. The indicated cell lines were transfected with either empty vectors (Vec-con) or vectors expressing promoter-reporter constructs DCLK1-L-LUC (a), or DCLK1-S-LUC-1 (b), and co-transfected with either control (scrambled) siRNA (con siRNA) or target-specific siRNA: (β-catenin-siRNA (a) or NF-κBp65-siRNA (b), for 48 hrs, as described below. In each case the target specific siRNA was effective in significantly down-regulating the expression of the target proteins by >80-90%. The data presented are representative of three separate experiments conducted similarly in duplicate. β-cat=β-catenin; p65=NF-κBp65; Vec-con=empty vector; Con=control. The corresponding β-actin levels in each sample are shown.

Figure 18:
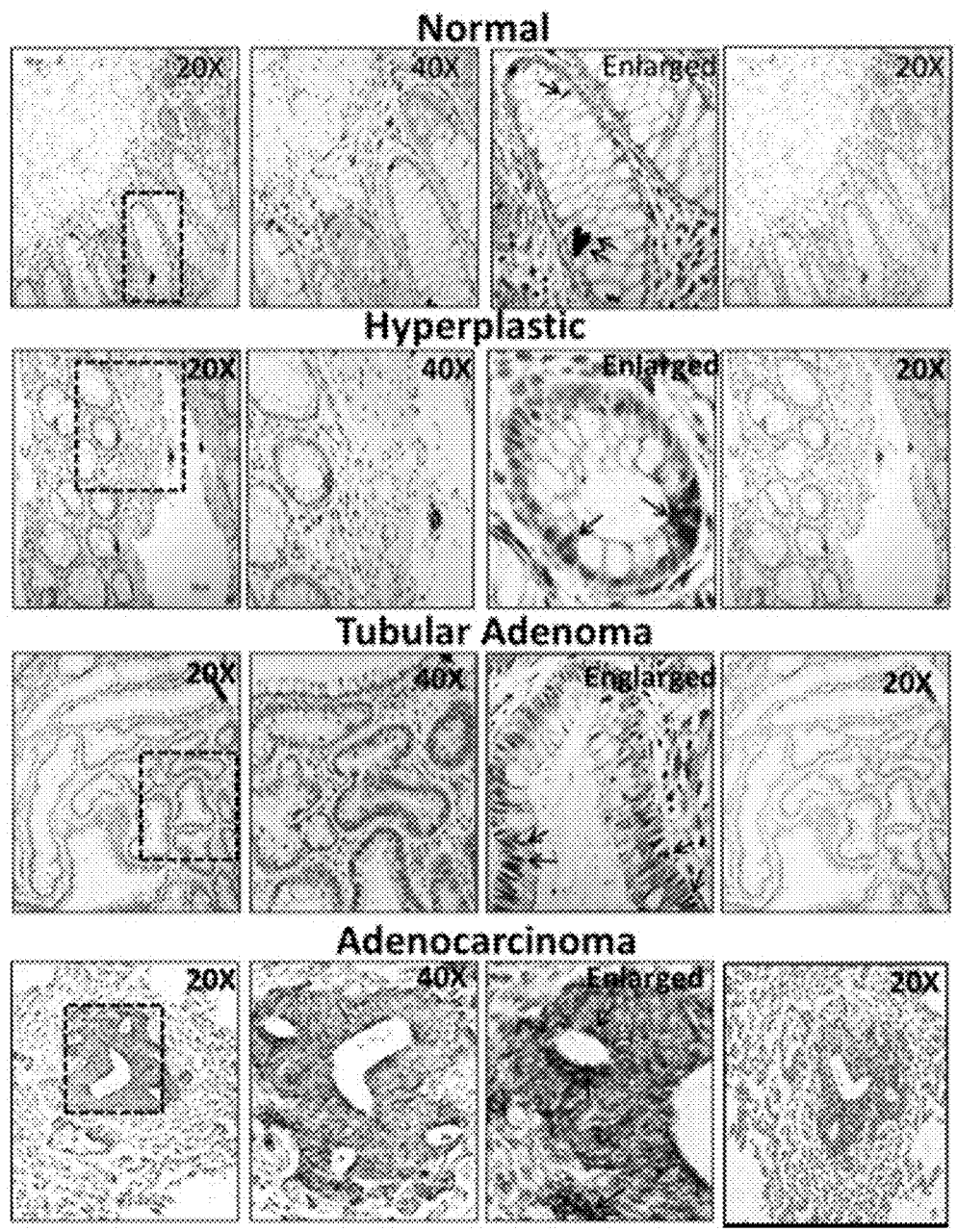

FIG. 18. Immunohistochemical staining of tissue sections from patient samples for DCLK1. In the left two vertical panels of (a-d), representative images of tissue sections, stained for DCLK1 protein, are presented from the indicated samples, obtained from patients. The tissue sections (5µ) were processed for IHC staining with commercially available antibodies against hDCLK1. The images were obtained at 20× and 40×, as shown. An inset was magnified to enlarge stained areas. The antibody used for staining does not differentiate between long and short isoforms of DCLK1. Single arrows highlight DCLK1 staining in the samples. In the case of normal colonic crypts in (a), the single arrows specifically highlight DCLK1 staining in colonic crypt cells at ~position 4. Crypts were also heavily stained in cells towards the luminal end of the crypts as highlighted by the double arrow, which may represent staining in tuft-cells, and needs to be confirmed by counter staining in future studies. Quantitative analysis of IHC images, stained for DCLK1. In the right vertical panels of (a-d), images were analyzed by Image J software (NIH) by method described in the working manual of the program (see imagej.nih.gov/ij/docs/examples/stained-sections/index.html). In brief the unit length of 50 μm was scaled as known distance and was used for all images selecting global scale. Images were then stacked to make montage of three colors: red, green and blue. The green image was adjusted to match the brown DCLK1 staining with red color to clearly reveal the stained regions. The threshold of the images was adjusted and the area stained was determined by selecting region of interests (ROI). The ROI for % area stained was analyzed and these numbers plotted using Microcal origin graphing and analysis software to achieve the distribution of staining across the sections.

FIG. 19. DCLK1 protein expression is significantly increased during colon-carcinogenesis in humans. The % area stained for hDCLK1 in normal (norm), hyperplastic (Hp), tubular adenoma (TA), and adenocarcinoma (AdCA) samples was quantified in duplicate sections of 6-10 patient samples. Briefly, the images were analyzed by Image J software and percent area stained was plotted as box plots (using Microcal Origin, Microcal Software, Inc.), wherein the first and third quartiles, median, maximum and minimum values from indicated number of samples are presented. At least 2-3 sections from each sample were analyzed and data from 6-10 patients/group are presented.

FIG. 20. Role of NF-κB binding site in activation of IntronV-promoter of DCLK1 gene. In silico analysis of IntronV-promoter demonstrated presence of a consensus TATA box and a consensus NF-κB binding site, as shown.

FIG. 21. PS41014 Peptide. The modified peptide used as an immunogen for injecting into the rabbit for generating DCLK1-S specific antibodies.

FIG. 22A-22E. Specificity of PS-41014 Ab for detecting DCLK1-S. (A) Western blot analysis of cell lysates with the Long specific DCLK1-Ab from Abcam; (B) WB analysis with the Abcam common Ab that detects both the short and long isoforms of DCLK1; (C) PS-41014 Ab for specifically detecting only the short isoform of DCLK1 in human samples; (D) Western blot analysis of tissue lysates from normal colon and adenocarcinomas with the PS-41014 Ab. (E) Western blot analysis of colorectal cancer cell lines with PS-41014 Ab.

Figures 23A, 23B:
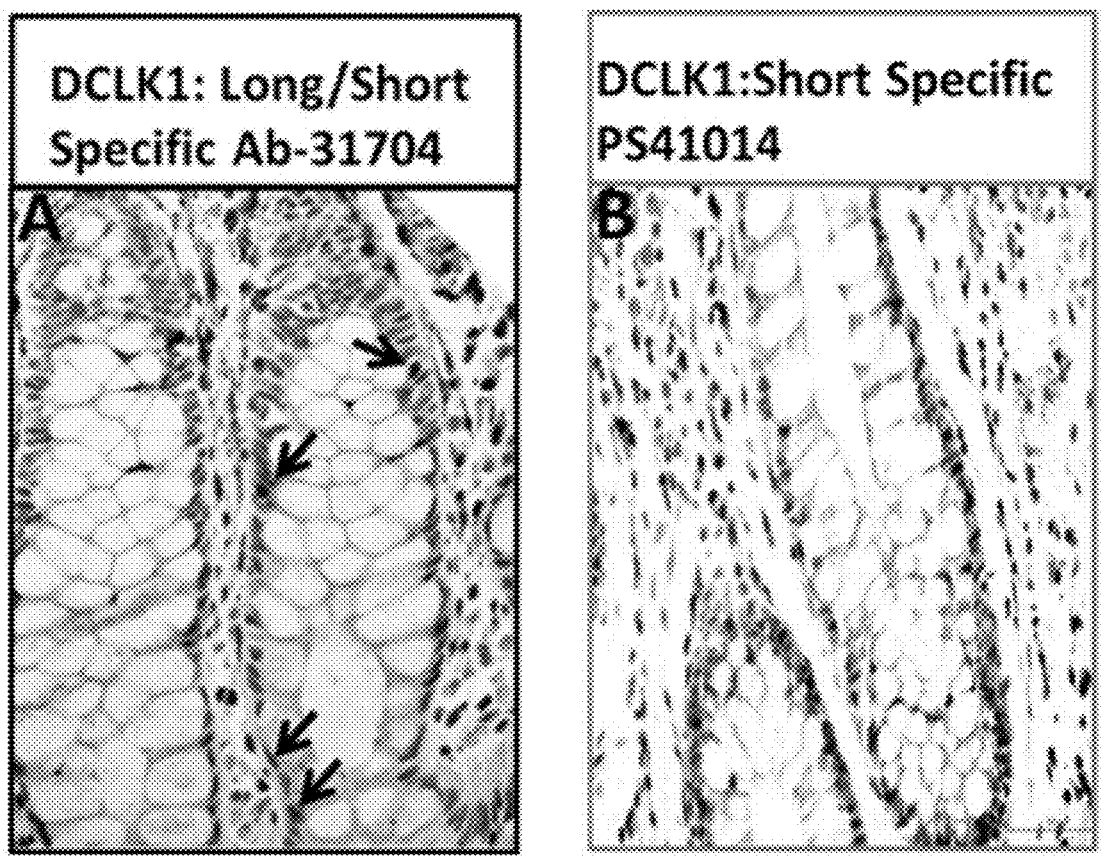

FIG. 23A-23B. Specificity of PS-41014 Ab. (A) Immunostaining of DCLK1 in normal colon stained with DCLK1 Ab from Abcam which detects both isoforms. Arrow heads indicate specific staining of DCLK1-L. (B) Stained with PS-41014 Ab to specifically detect only DCLK1-S in human samples.

Figures 24A, 24B, 24C:
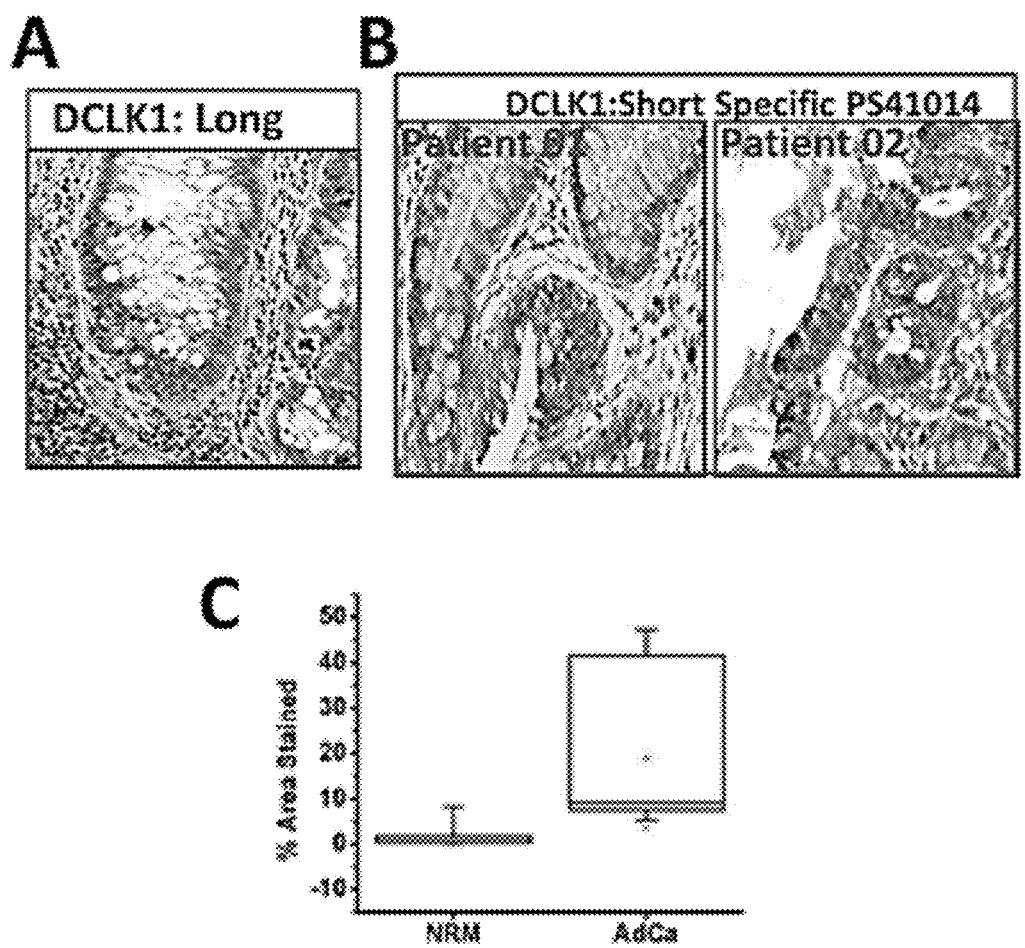
Figures 25A, 25B, 25C, 25D, 25E:
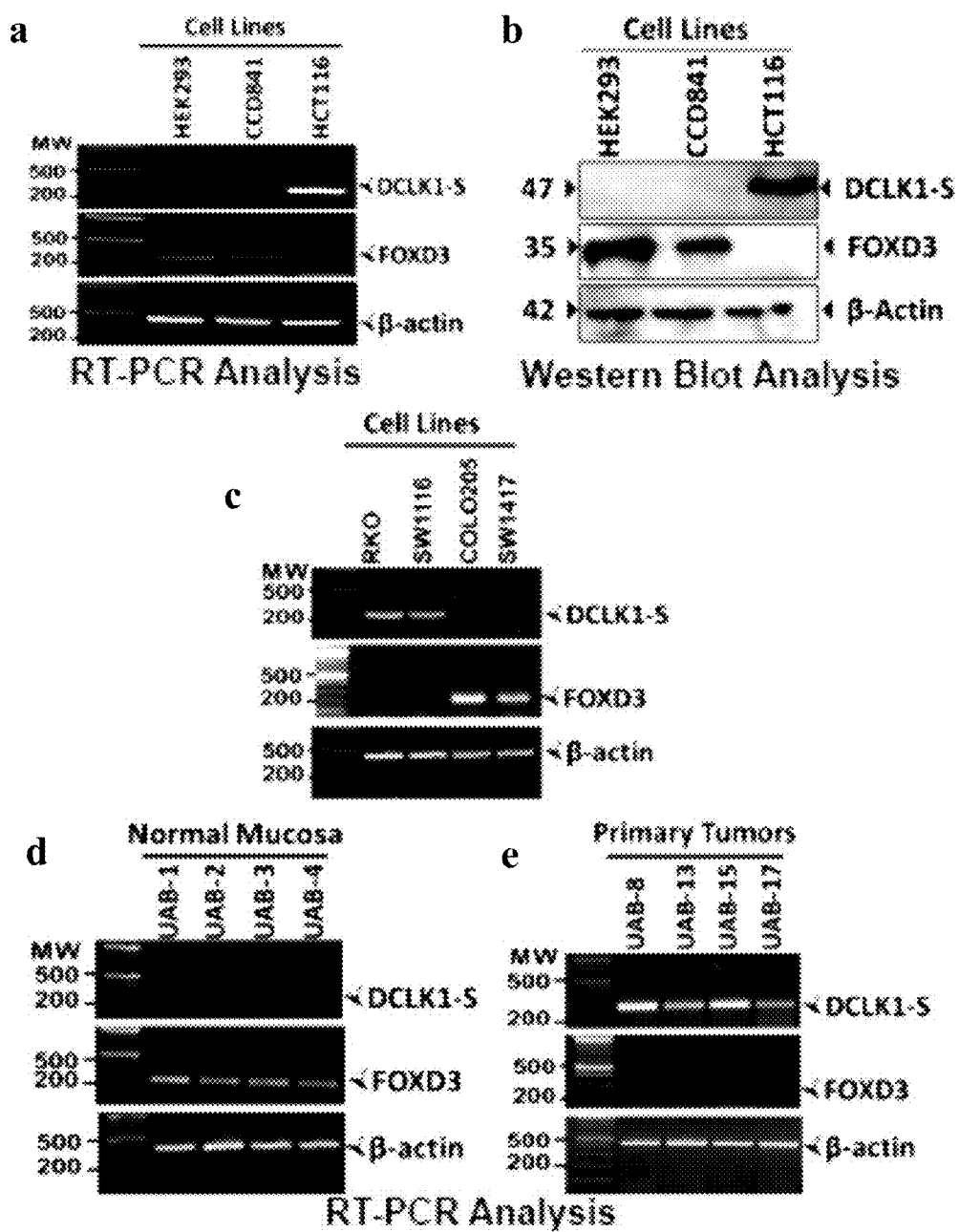

FIG. 24A-24C. Specificity of PS-41014 Ab. Immunostaining of DCLK1 in adenocarcinoma tissue sections. (A) Tissue sections stained with abcam Ab specific for DCLK1-L. (B) DCLK1-S stained with PS-41014 Ab. (C) the images were analyzed by Image J software and percent area stained was plotted as box plots (using Microcal Origin, Microcal Software, Inc.), wherein the first and third quartiles, median, maximum and minimum values from indicated number of samples are presented. At least 2-3 sections from each sample were analyzed and data from 6-10 patients/group are presented.

FIG. 25A-25E. Expression of DCLK1-S and FOXD3 in Human Cell Lines and Human Patient Samples.

Figure 26:
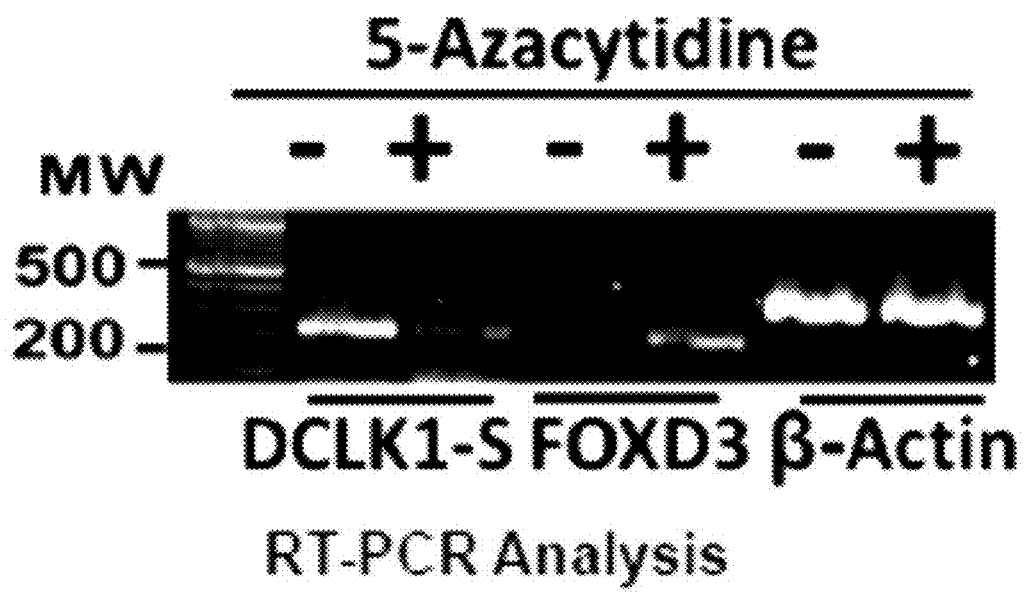

FIG. 26. Epigenetic Silencing of FOXD3 promoter in HCT116 Colon Cancer Cells.

Figures 27A, 27B, 27C:
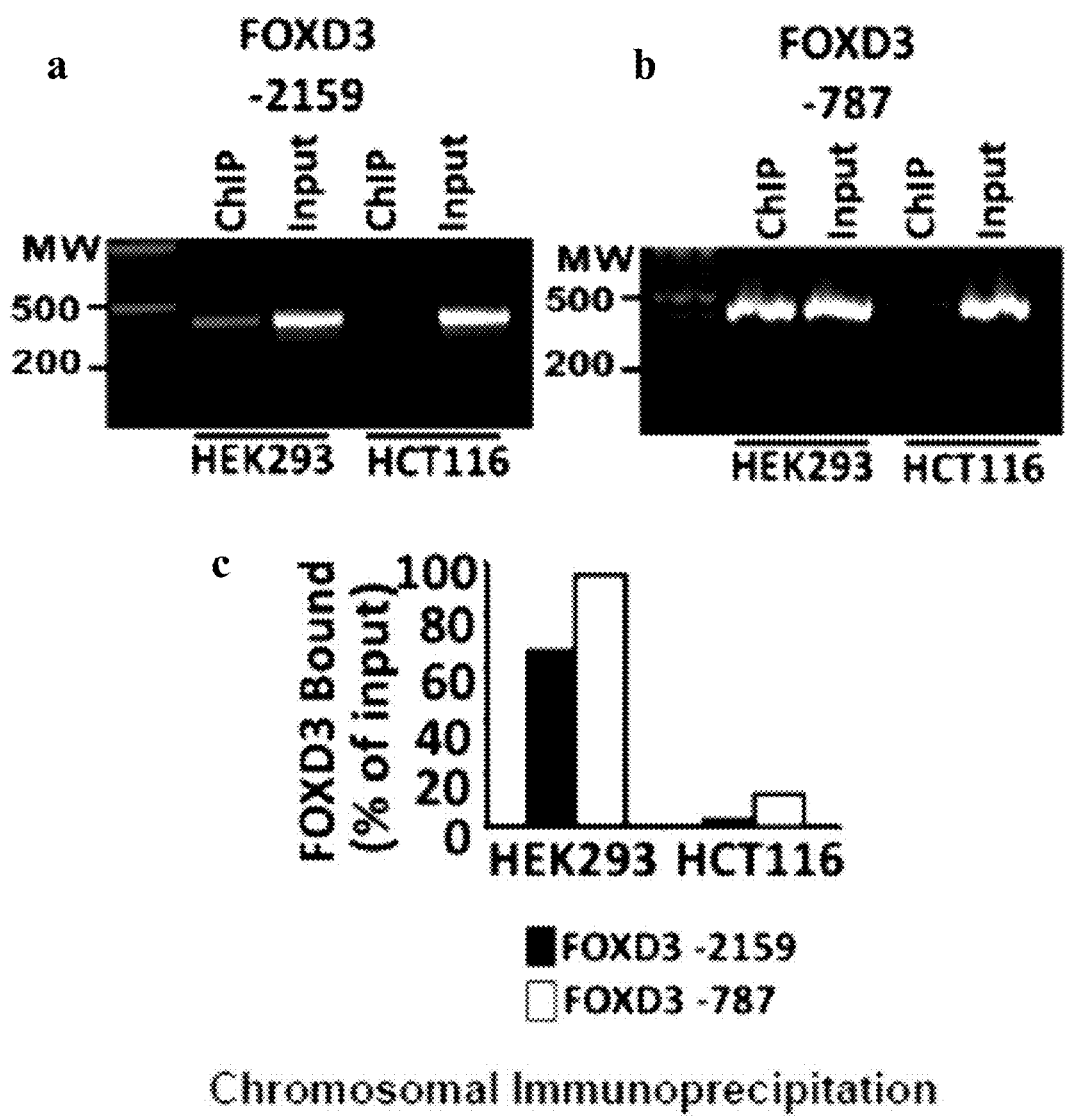

FIG. 27A-27C. Role of FOXD3 Binding Sites in Activation of the IntronV-(β)-promoter of DCLK1-Gene.

Figures 28A, 28B, 28C:
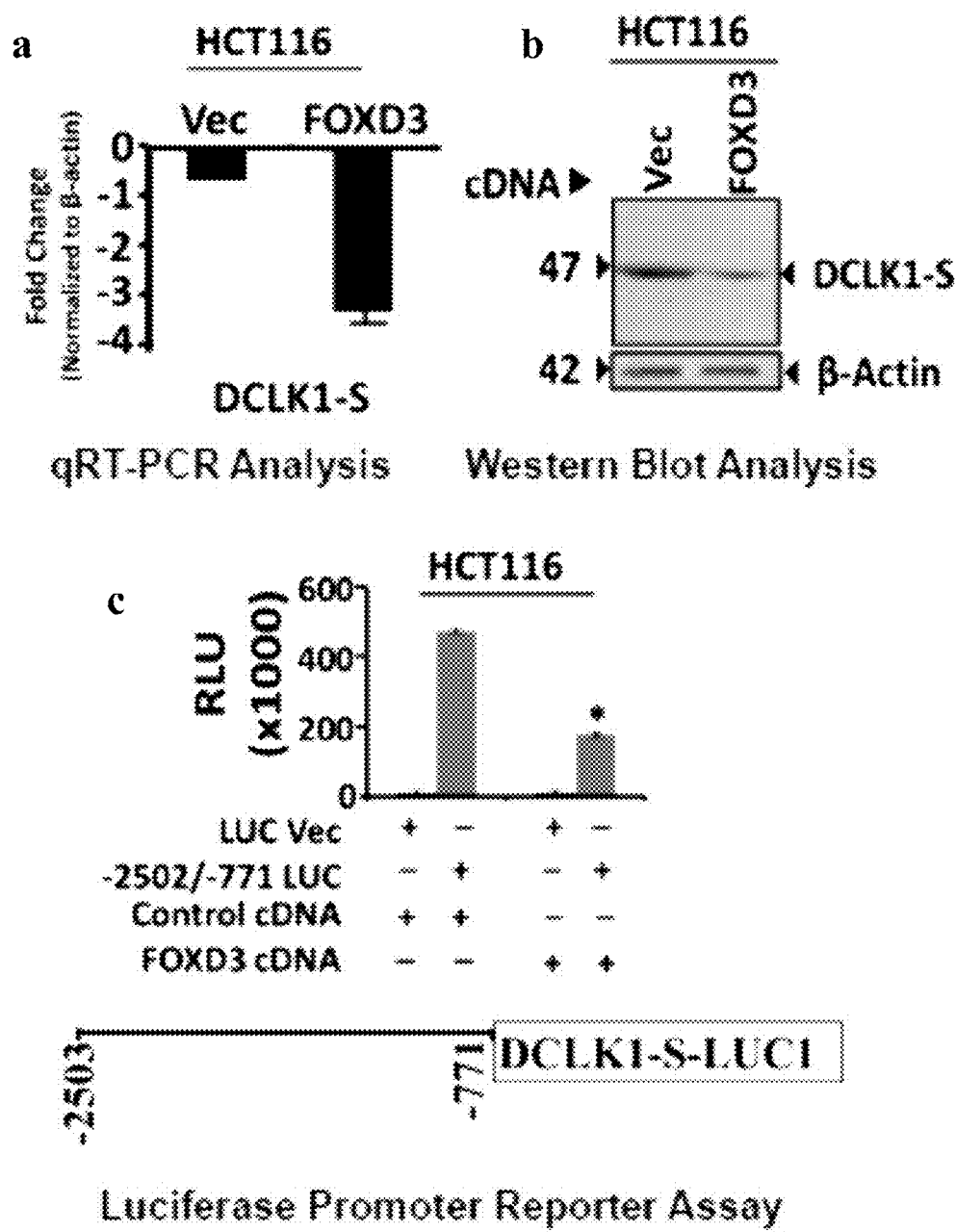

FIG. 28A-28C. Overexpression of FOXD3 Results in Inhibition of the IntronV-(β)-promoter of DCLK1-Gene.

Figures 29A, 29B, 29C:
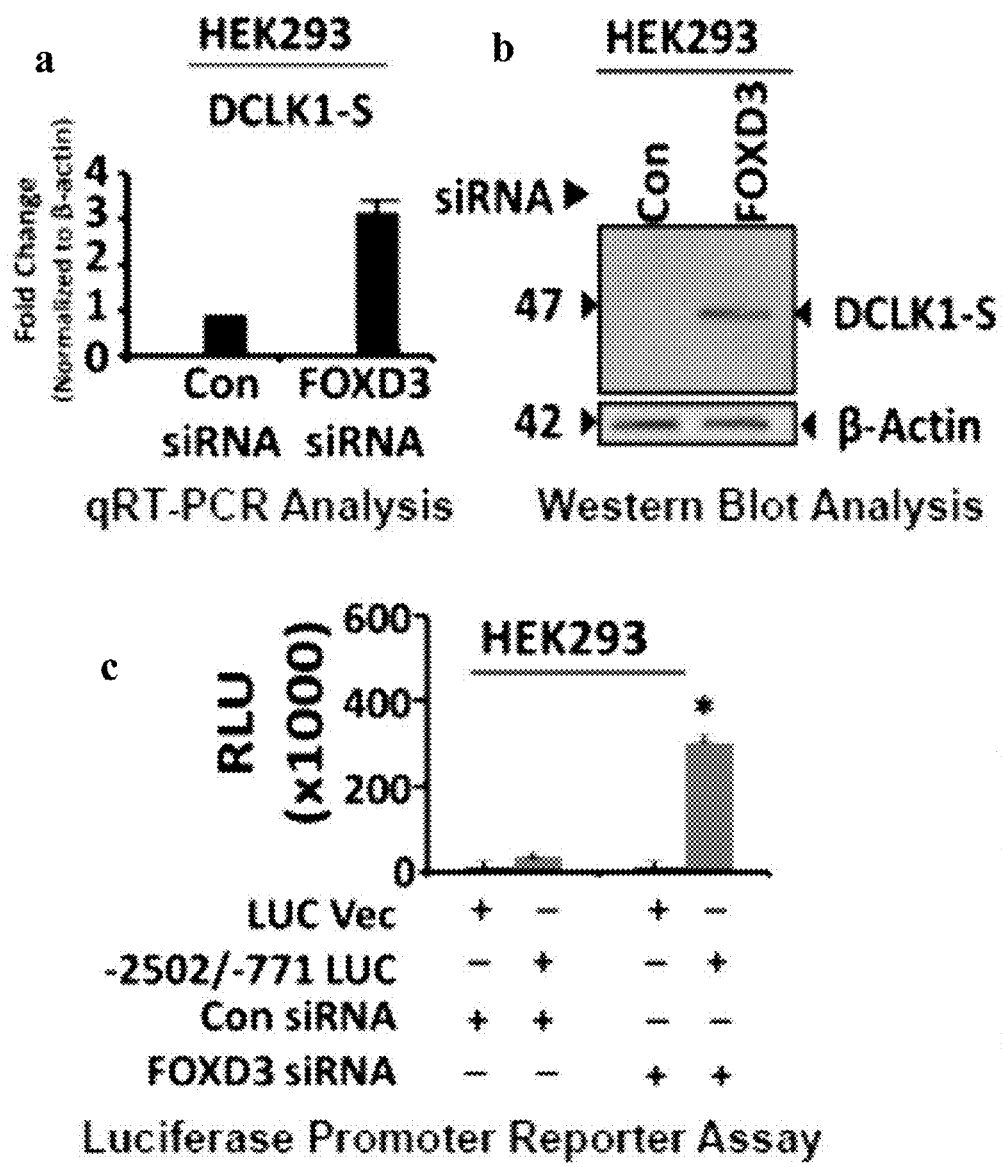

FIG. 29A-29C. Downregulation of FOXD3 Results in Activation of the IntronV-(β)-promoter of DCLK1-gene.

Figure 30:
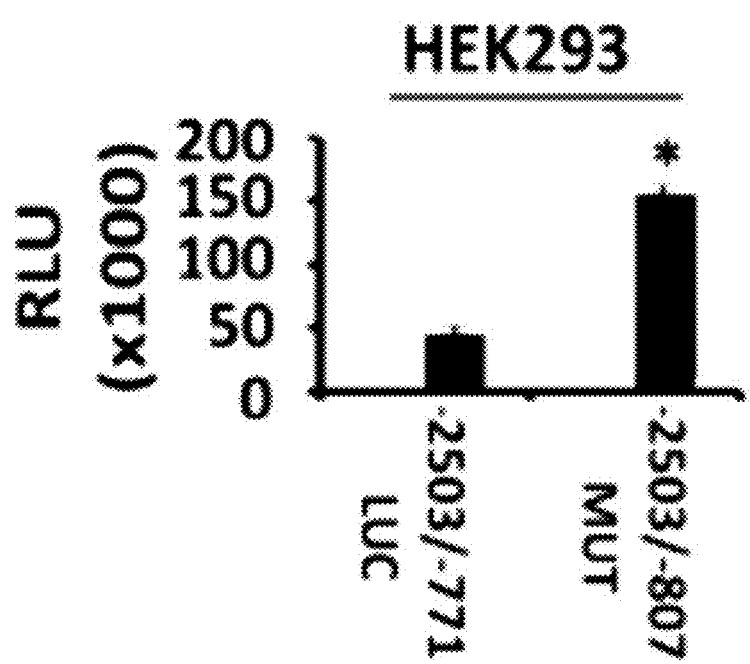

FIG. 30. Mutation of FOXD3 Binding Sites Results in Activation of the IntronV-(β)-promoter of DCLK1-gene.

Figure 31A:
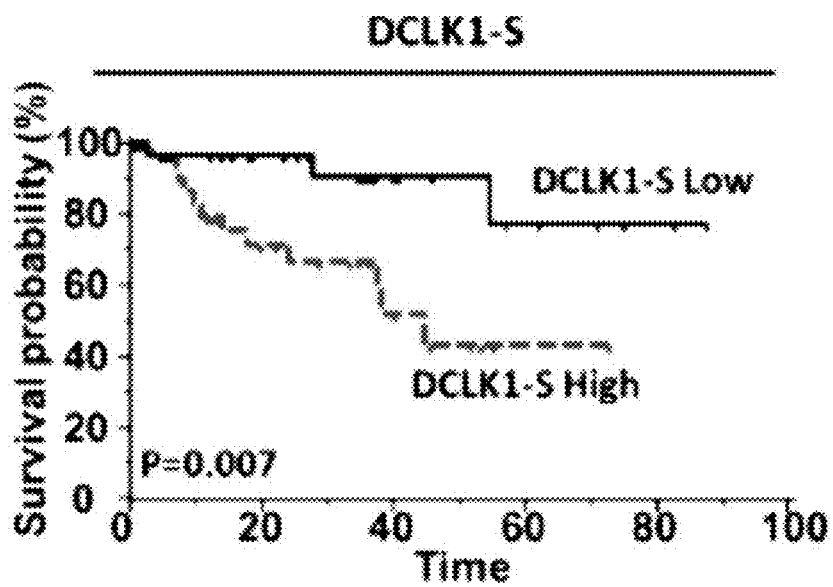
Figure 31B:
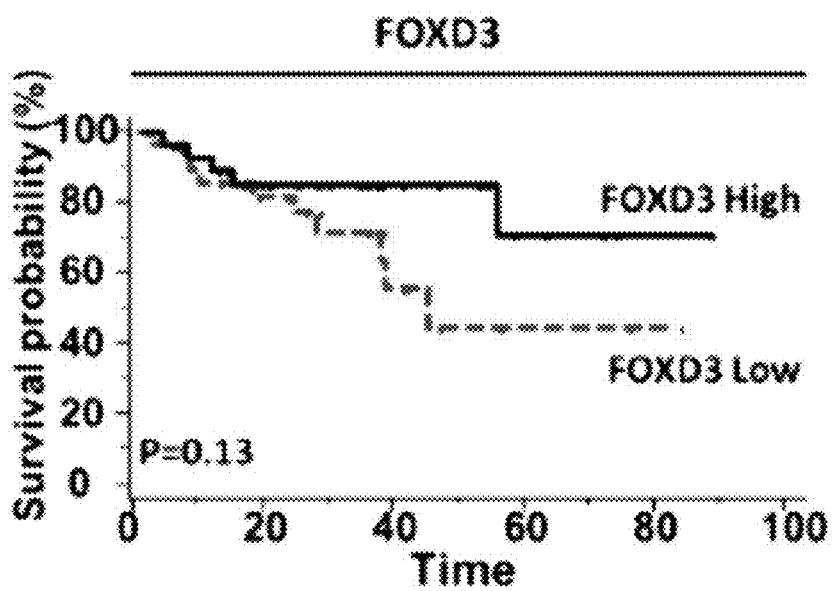

FIG. 31A-31B. High expression of DCLK1-S and Low expression of FOXD3 in hCRC samples is associated with poor patient survival.

Figure 32:
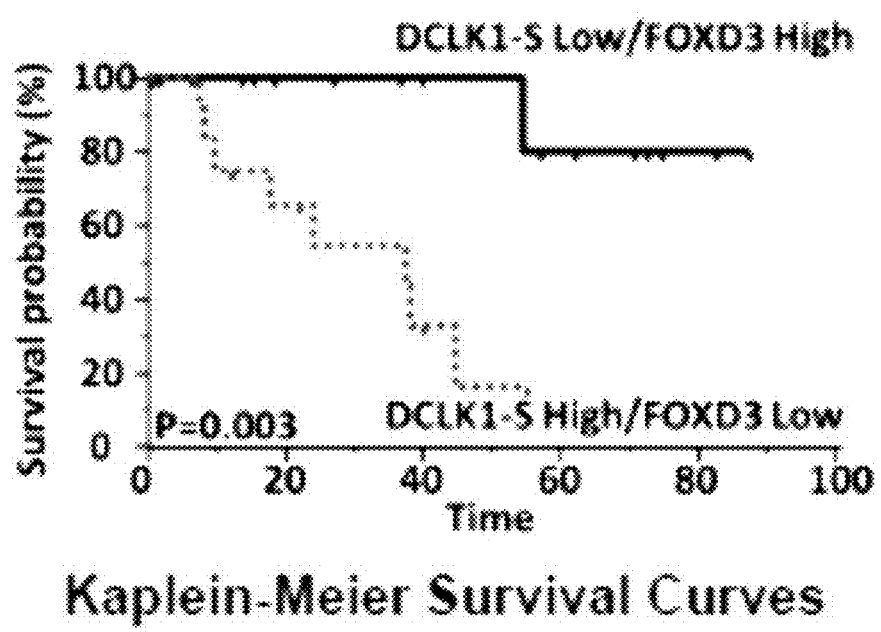

FIG. 32. High expression of DCLK1-S and low expression of FOXD3, was a stronger independent prognostic factor than high expression of DCLK1-S alone.

DESCRIPTION

DCLK1-gene encodes a member of the protein kinase family and double-cortin family (Lin et al., *J Neurosci*. 2000, 20(24):9152-61), and was initially reported to play a critical role in neurogenesis and neuronal migration (Lin et al., *J Neurosci*. 2000, 20(24):9152-61; Shu et al., *Neuron*. 2006, 49(1):25-39; Shin et al., *Nat Commun*. 2013, 4:1440). Thereafter, investigators reported an important role of DCLK1 in dictating cognitive behavior of mice and humans (Shin et al., *Nat Commun*. 2013, 4:1440; Le Hellard et al., *PLoS One*. 2009, 4(10):e7534). A possible important role of DCLK1 in maintaining tumorous growths was first learned from experiments with neuroblastomas (Verissimo et al., *PLoS One*. 2013, 8(9):e75752; Verissimo et al., *Endocr Relat Cancer*. 2010, 17(2):399-414). Only in the past 7-8 years, epithelial expression of DCLK1 was described for the first time in mouse gastric epithelial cells (Giannakis et al., *J Biol Chem*. 2006, 281(16):11292-300), and the authors speculated that DCLK1 was being expressed by gastric stem cells. Several papers were published describing DCLK1 expression in mouse intestinal crypts (May et al., *Stem Cells*, 2008, 26(3):630-7; May et al., *Stem Cells*. 2009, 27(10): 2571-9). Expression of DCLK1 in mouse colonic crypts was reported to be significantly elevated in response to progastrins (potent mitogens for colonic epithelial cells and colon cancers (Sarkar et al., *Gastroenterology*. 2011, 140(2):583-95.e4; Jin et al., *J Clin Invest*. 2009, 119(9):2691-701), which correlated with hyperproliferation of the crypts (Sarkar et al., *Gastroenterology*. 2011, 140(2):583-95.e4). DCLK1 is also expressed by acetylated Tuft cells, located in the upper ⅓ of colon crypts in mice (Gerbe et al., *Gastroenterology*. 2009, 137(6):2179-80; author reply 80-1). More recently, a critical role of DCLK1 positive Tuft cells was reported in developing colon and pancreatic tumors/lesions in mutant mouse models of carcinogenesis (Westphalen et al., *J Clin Invest*. 2014, 124(3):1283-95; Bailey et al., *Gastroenterology*. 2014, 146(1):245-56). DCLK1 positive Tuft cells were reported to be required for restitution of mouse intestinal crypts in response to inflammation/radiation damage (May et al., *Stem Cells*. 2014, 32(3):822-7). Thus the literature so far strongly implicates a possible important role of DCLK1 in mouse colon tumorigenesis and in maintaining the growth of human colon cancers.

A number of long (~80-82 KDa) and short (~45-50 KDa) isoforms of DCLK1 have been identified in the mice and human brains/neurons (Engels et al., *Brain Res Mol Brain Res.* 2004, 120(2):103-14; Omori et al., *J Hum Genet.* 1998, 43(3):169-77; Shang et al., *Biochemistry.* 2003, 42(7):2185-94; Burgess and Reiner, *J Biol Chem.* 2002, 277(20):17696-705; Silverman et al., *J Biol Chem.* 1999, 274(5):2631-6). The ~82 kDa long isoform of DCLK1 contains: two N-terminal doublecortin domains which bind microtubules, a C-terminal serine/threonine kinase domain with homology to $Ca^{2+}$/calmodulin dependent protein kinases and a middle serine/proline rich domain, which mediates protein interactions. The nomenclature for the various isoforms has remained a source of confusion, and differs even in the Swiss-Prot and NCBI databases. The specific biological function of the various isoforms has remained undefined. The shorter isoforms lack the two N terminal doublecortin domains. Thus the 3D structure of the long vs short isoforms can be expected to be quite different, with perhaps some differences in their biological interactions and activities. The longer isoforms and their splice variants are presumed to be transcriptionally regulated by the 5'($\alpha$)-promoter. The origin of the shorter isoforms has not been investigated to a significant extent, but a 3' promoter (termed $\beta$-promoter (Shang et al., *Biochemistry.* 2003, 42(7):2185-94)), downstream of the 5'($\alpha$)-promoter has been implicated in transcribing shorter-transcripts of DCLK1 in mouse cerebellum (Pal et al., *Genome Res.* 2011, 21(8):1260-72). In at least one report, a TATA box containing promoter was described in the intron-V of DCLK1-gene in neuronal cells (Le Hellard et al., *PLoS One.* 2009, 4(10):e7534). Unlike the neuronal cells, possible expression of different isoforms of DCLK1 by normal colonic epithelial cells and colon cancer cells/tumors has not been investigated to-date. The presence of DCLK1 protein in epithelial cells has so far been mainly examined by using commercial antibodies, generated against the common C terminal end of long and short isoforms. Thus the specific isoform(s) being expressed by epithelial cells has remained unknown.

DCLK1 is a specific marker of colon and pancreatic cancers in mice, and is expressed by human colon adenocarcinomas (hCRCs). It was recently reported that, down-regulation of DCLK1 results in loss of cancer-stem-cells (CSCs), and inhibits spheroidal/xenograft growths from hCRC cells. The 5'-promoter of DCLK1 gene was recently reported to be hypermethylated in hCRCs, resulting in loss of expression of DCLK1 transcripts, originating from 5'($\alpha$)-promoter (termed DCLK1-L isoform). However, in mouse colon-tumors, 5'-promoter of DCLK1 gene remains unchanged, and DCLK1-L isoform, originating from 5'($\alpha$)-promoter, is expressed. The inventors contemplate that elevated levels of DCLK1 protein, previously reported in hCRC cell lines, may be transcribed/translated from an alternate-promoter.

In one example, a human anti-DCLK1-S-antibody (e.g., PS-41014) was generated to specifically detect DCLK1-S protein in colon cancer cells and not in normal human colon cells. To confirm the specificity of the Ab generated (PS-41014), two commercially available antibodies were used that either detect only the long isoform of DCLK1 (Abcam Cat#Ab-106635) or detect both long and short isoforms of hDCLK1 (Abcam Cat#Ab-31704). Cell lysates were made from logarithmically growing normal and cancer cell lines that were found to either express only DCLK1-L or only DCLK1-S at the transcript level. Approximately 50 µg of the cell lysates were loaded per well and resolved via 10% SDS-PAGE. The proteins were immunoblotted to nylon membrane and probed with the three antibodies described above. All three antibodies were diluted and used at a concentration of 0.4 µg/ml.

Figures 22A, 22B, 22C, 22D, 22E:
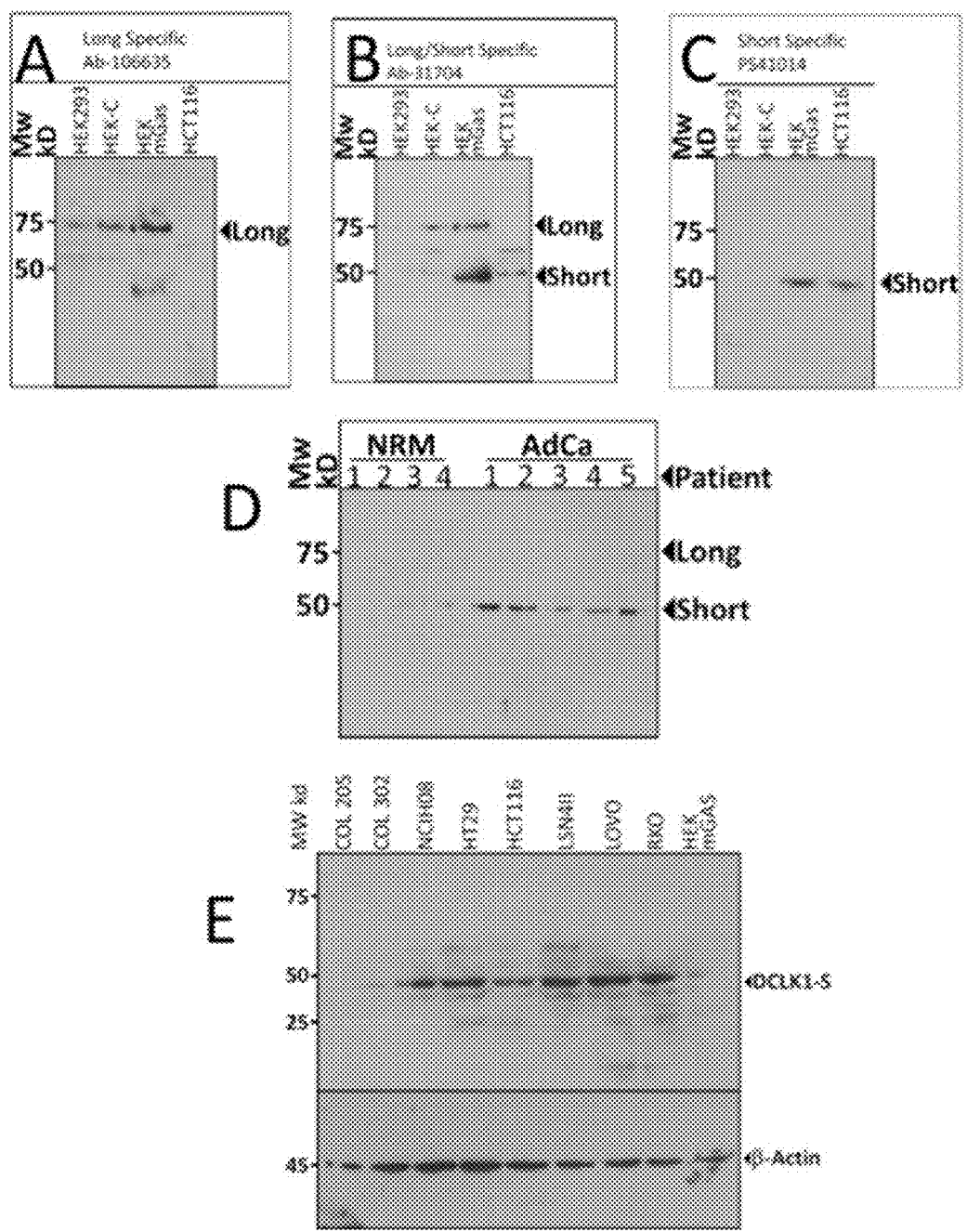

The Abcam Ab (Cat#Ab-106635) was generated against a 14 amino acid peptide near the amino terminus of human DCLK1 (NP_004725) and only detects the DCLK1-L isoform of ~80 KDa, as was confirmed in HEK293, HEK-C and HEK-mGAS cells (FIG. 22A), which are known to express either only the L isoform or both the L and S isoforms. The same set of cells were also probed with the common Abcam Ab (Cat#Ab-31704) which detects both the long and short isoform of human DCLK1, since this Ab was generated against C terminal amino acids between 700 and 729 amino acids, common to all the isoforms of DCLK1, other than CARP, which is not expressed in colonic epithelial cells. As shown in FIG. 22B, this common Ab detected both the long and short isoforms of DCLK1. DCLK1-L was detected only in HEK293, HEK-C and HEKm-GAS cells, while HCT116 colon cancer cells which only express the short isoform demonstrated only the shorter isoforms (~47 kD protein) in FIG. 22B. However, unlike the commercial Ab 31704, which detects both DCLK1-L and S isoforms, the DCLK1-S specific antibody (PS-41014) only detected the expression of the short isoform (47 KDa) in HEKmGAS and HCT116 cells and did not detect the long isoform expressed by non-transformed cells (HEKc and HEK-293) (FIG. 22C). Thus at similar concentrations, the PS-41014 Ab was equally effective and specific for DCLK1-S isoform, with minimum background and cross reactivity.

Similarly, PS41014 antibody was found to specifically detect the short isoform of DCLK1 in the lysates from adenocarcinoma samples obtained from patients, but not in lysates prepared from normal human colonic mucosa, by western blot analysis (FIG. 22D). Lysates prepared from several human colon cancer cell lines were also examined by the DCLK1-S specific antibody, and the panel of colorectal cancer cells showed a strong and specific band for the presence of DCLK1-S in the lysates, with no background and minimal non-specific reactivity (FIG. 22E).

Paraffin embedded sections were de-paraffinized in a gradient of xylene, alcohol, and water using standard protocols. For better immunoreactivity, the antigenic sites were retrieved by boiling for 20 min in citrate buffer pH 6.0 containing Tween 20. The sections were cooled to room temperature and then blocked with 5% normal goat serum mixed in Tris-Cl buffer (25 mM, pH 7.4) containing 5% BSA. The sections were incubated in the blocking buffer with 50 ng of the commercial Ab described above and the PS-41014 Ab in a humidified chamber at 4° C. overnight. The sections were washed in TBST (Tris-Cl 25 mM, pH 7.4; NaCl 0.9 g/100 ml; Tween20 0.2%) buffer 10 min×3. The Ab bound to the protein was detected by ABC kit (Vector lab Inc) as per manufacturer's protocol, followed by DAB and hemotoxylin staining.

The normal colon sections stained for DCLK1-L with the DCLK1-long specific Ab from Abcam (Cat#Ab-106635) (FIG. 23A), confirming that the staining protocol followed detected the expected staining. The PS-41014 Ab, however, did not detect the expression of any DCLK1 in the normal colons, with no appreciable background staining (FIG. 23B). These findings confirmed our earlier findings, described above, that normal colon cell lines and normal human colons do not express DCLK1-S.

Tissue sections of colon Adenocarcinomas from patients were similarly stained with DCLK1-long specific Ab from Abcam (Cat#Ab-106635) and as expected this Ab did not detect any appreciable staining in the adenocarcinoma sections (FIG. 24A). However, the same sections from adenocarcinomas stained clearly and strongly with the PS-41014 Ab (FIG. 24B). The staining was intense in the epithelial cells but few stromal cells were also very lightly stained, with hardly any background, non-specific, staining. All stained sections were finally analyzed by Image J software to get a quantitative estimation of the staining intensity (FIG. 24C).

The DCLK1-S specific antibody was tested for its use in the immunofluorescence (IF) detection of DCLK1-S in colorectal cancer cells and adenocarcinomas. The colon cancer cells were grown on glass cover overnight and then fixed in Acetone:methanol for 20 min followed by immunostaining protocol and the tissue sections were processed as described for immunohistochemistry. Both the cells and the tissue sections were blocked and probed with DCLK1-S specific PS-41014 Ab as described for immunohistochemistry. Primary Ab binding was detected by anti-rabbit Texas Red for 2 hours at room temperature (RT) and stained for the nucleus with DAPI for 5 min at RT. The sections were washed and mounted on glass slides and imaged under epifluorescence microscope. Colorectal cancer cell lines showed cytoplasmic staining of DCLK1-S in all the cells tested by the Ab. Intense staining of DCLK1-S in adenocarcinoma tissue sections correlated with the immunostaining and western blot analysis, shown in FIGS. 22A and 24B. Tissue Sections were analyzed by Image J software to get a quantitative estimation of the staining intensity.

Several in silico and molecular biology approaches were used to study DCLK1 isoforms. The majority of hCRCs express short-transcripts of DCLK1 (termed DCLK1-S) from an alternate β-promoter in intron-V of the gene, while normal colons mainly express the long transcript (DCLK1-L) from 5'(α)-promoter. β-catenin and TCF4/LEF binding-sites are used for activating (α)-promoter, while binding of activated NF-κBp65 to NF-κB cis element, activates (β)-promoter in cancer cells. DCLK1-S expression was examined in a cohort of 92 CRC patients, in relation to overall survival and clinicopathological parameters. High expressors had significantly worse overall-survival and disease free intervals compared to low expressors, and DCLK1-S expression was found to be an independent prognostic factor.

The usage of the alternate (β)-promoter in intron-V by hCRCs, suggests that DCLK1-S may represent an important target for preventing or inhibiting colon cancers, and for eliminating colon-CSCs. Measuring DCLK1-S in colonic tumors of patients may be used in prognosing and/or diagnosing CRC.

In studies with mutant mouse models of colon/pancreatic tumorigenesis a bac construct, expressing either the reporter gene or diphtheria toxin, downstream of the 5' promoter of mouse DCLK1 gene was used, suggesting that 5' promoter remains functional during intestinal/pancreatic tumorigenesis in mice, which likely results in the expression of the long isoform(s). The 5' promoter of hDCLKJ-gene, however, was recently reported to be hypermethylated in hCRCs, by several investigators (Vedeld et al., *Epigenetics*. 2014, 9(3):346-50; Vedeld et al., *Int J Cancer*. 2014. PubMed PMID: 24948044), suggesting the possibility that the 5' promoter of hDCLK1-gene may be epigenetically silenced in hCRCs. This intriguing possibility was examined and findings suggest that hypermethylation of 5' promoter is an early event during adenoma-carcinoma sequence of colon carcinogenesis in humans, unlike mice. The data also suggests an absence of expression of long transcripts/isoforms in all 15 human colon cancer cell lines (hCCCs) screened to-date, suggesting epigenetic silencing of the 5'(α)-promoter due to its hypermethylation in hCRCs.

Even though the 5'(α)-promoter is epigenetically silenced in hCCCs/hCRCs, high levels of DCLK1 protein have been reported in hCCCs/hCRCs (Kantara et al., *Cancer Res.* 2014, 74(9):2487-98; Gagliardi et al., *Pathol Res Pract.* 2012, 208(8):475-9; Singh et al., *Curr Colorectal Cancer Rep.* 2012, 8(4):277-89; Gagliardi et al., *Clin Exp Gastroenterol.* 2012, 5:35-42). The discrepancy between the reported presence of DCLK1 protein in hCCCs/hCRCs, but hypermethylation/epigenetic silencing of 5'(α)-promoter, suggests the possibility that hCCCs/hCRCs may be utilizing an alternate promoter for expressing alternate isoforms of DCLK1.

In silico analysis of hDCLK1 gene, confirmed the presence of a canonical TATA box within the β promoter located within intron-V. The intron-V (β) promoter is used as an alternate-promoter by hCCCs/hCRCs for expressing a short transcript. Based on sequence homology, the long (L) and short (S) transcripts of DCLK1, found in normal human colon cell lines/normal human colons (hNCs) vs hCCCs/hCRCs, respectively, were determined to be identical to isoforms 1 (NM_004734.4) and 2 (NM_001195415.1) in the NCBI data base. Isoform 1 is referred to as DCLK1-L and isoform 2 is referred to as DCLK1-S, to differentiate between the molecular size of the two isoforms. Colon tumors and normal colons from mice, on the other hand, were confirmed to only express the long isoform(s).

Transcriptional regulation of the α/β promoters in the hDCLKJ-gene remains largely unknown. Activation of β-catenin and NF-κBp65 was reported to be critically required for up-regulating DCLK1 protein in response to autocrine and endocrine progastrins (Sarkar et al., *Gastroenterology*. 2011, 140(2):583-95.e4). In silico analysis of the two promoters was conducted followed by promoter-reporter/ChIP assays, in the presence or absence of the known activator (progastrin), identifying the role of β-catenin binding to TCF4/LEF binding-sites for activating 5'(α)-promoter.

In order to define pathophysiological relevance of DCLK1-S expression by hCRCs, the overall-survival of a cohort of 92 CRC patients was examined in relation to high/low expression of DCLK1-S. A clinically important finding was that high-expressors of DCLK1-S had significantly worse overall-survival, and disease free interval. DCLK1-S expression represented an independent diagnostic/prognostic marker for CRC patients. Thus specifically targeting DCLK1-S may eliminate CSCs, since hCCCs, downregulated for DCLK1, lost the ability to form tumorospheres/tumors (Kantara et al., *Cancer Res.* 2014, 74(9): 2487-98).

A clinically important discovery described herein is that an alternate-promoter (β) within IntronV of DCLK1 gene is used by human colon cancer cell lines (hCCCs) and hCRCs to express a short-transcript of DCLK1 (DCLK1-S) (termed Isoform 2 in NCBI data base). In a cohort of 92 patients, it was found that high-expressers of DCLK1-S had an overall worse survival and disease free survival than low-expressers (FIG. 9). DCLK1-S expression was determined to be an independent prognostic factor for patients with CRCs (Table 8). Another important finding was that activation of IntronV (β)-promoter of hDCLK1-gene, followed epigenetic silencing of 5'(α)-promoter and loss of expression of DCLK1-L during adenoma-carcinoma sequence of colon-carcinogenesis. Since the shorter transcripts lack doublecortin-domains, the 3D structure of S vs L isoforms will be significantly different, and impact biological activity. The latter possibility is supported by findings with isogenic clones of HEK-293 cells (HEKmGAS, HEKC) which differed in their tumorigenic/metastatic potential (Sarkar et al., *Int J Cancer.* 2012, 131(7):E1088-99). A significant increase in activation of IntronV(β)-promoter was measured in HEKmGAS cells, resulting in the expression of relatively high levels of short-isoform, which may have played an important role in imparting tumorigenic/metastatic potential to the cells. The control HEKC cells remained poorly tumorigenic, and only expressed the L-transcript. In preliminary studies the inventors have found that overexpression of the S-isoform in non-tumorigenic HEK293 cells imparts clonogenic/tumorigenic potential to the cells, which supports the possibility that the S-isoform plays a role in increasing the tumorigenic potential of the cells. The crystallographic structures of the intact isoforms have yet to be studied, which may provide important clues to functional interactions and biological activity of L/S isoforms.

Interestingly, the inventors did not observe DNA-methylation of 5'(α)-promoter in HEKmGAS cells, suggesting that epigenetic silencing of 5(α)'-promoter is not a prerequisite for activating IntronV(β)-promoter. Sustained activation of NF-κB, downstream of autocrine PG, may play an important role as well, as suggested by data in FIG. 7. Overexpression of PG in normal intestinal epithelial cells was ineffective towards imparting tumorigenic potential to the cells (Singh et al., *Gastroenterology.* 2000, 119(1):162-71), suggesting that overexpression of PG and activation of NF-κB pathway, in the context of human embryonic cells, up-regulates tumorigenic pathway which appears to include activation of IntronV(β)-promoter of hDCLK1-gene. Inflammatory microenvironment of tumors, potentially leading to sustained activation of NF-κB pathway, may also play a role in elevated levels of DCLK1-S in Ads/AdCAs, in situ, (FIG. 2 and FIG. 3), as suggested in literature (Schwitalla et al., *Cell.* 2013, 152(1-2):25-38). Thus, factors up-stream of activation of DCLK1-S expression, such as an inflammatory-microenvironment/progastrins/activation of oncogenic-pathways, likely play an important role in the expression of DCLK1-S in hCRCs.

A critical role of DCLK1 expression in maintaining tumorigenic/metastatic potential of hCCCs/CSCs was previously reported (Kantara et al., *Cancer Res.* 2014, 74(9): 2487-98; Sureban et al., *J Nanobiotechnology.* 2011, 9:40). In the current studies, DCLK1-S was identified as the major isoform in hCCCs/hCRCs, with a few exceptions (FIG. 2 and FIG. 3), suggesting that DCLK1-S likely supports the previously reported tumorigenic/metastatic potential of hCCCs (Kantara et al., *Cancer Res.* 2014, 74(9):2487-98; Sarkar et al., *Int J Cancer.* 2012, 131(7):E1088-99). However, in mouse models of colon-carcinogenesis, high levels of Dclk1-L in the absence of Dclk1-S are expressed (FIG. 3E). Co-expression of diphtheria-toxin in Dclk1+cells in small-intestines/colons, results in loss of tumorigenesis in mouse models of colon carcinogenesis (Nakanishi et al., *Nat Genet.* 2013, 45(1):98-103; Westphalen et al., *J Clin Invest.* 2014, 124(3):1283-95). These findings suggest that Dclk1-L expression is required for colon tumorigenesis in mice. Metastatic spread of mouse colon tumors, however, has not been reported in $Apc_{Min/+}$ mice or in mice treated with AOM±DSS (Nakanishi et al., *Nat Genet.* 2013, 45(1):98-103; Westphalen et al., *J Clin Invest.* 2014, 124(3):1283-95; Cobb et al., *Cancer.* 2004, 100(6):1311-23; Singh et al., *Gastroenterology.* 2000, 119(1):162-71). Epithelial-mesenchymal-transition by hCCCs requires DCLK1 expression (Chandrakesan et al., *Oncotarget.* 2014. PubMed PMID: 25211188), suggesting that metastatic spread of colon cancer cells may require the expression of DCLK1-S by hCCCs, which only express DCLK1-S (Table 6). The inventors recently reported expression of DCLK1-S by circulating cancer-stem-cells in hCRC patients (Kantara et al., *Lab Invest.* 2015, 95(1):100-12), providing further evidence that DCLK1-S may be required for imparting metastatic potential to hCCCs. The latter possibility is further supported by the fact that, HEKmGAS cells overexpressing DCLK1-S (FIG. 2 and FIG. 3), implanted in the cecum of athymic nude mice, metastasized to the liver (Sarkar et al., *Int J Cancer.* 2012, 131(7):E1088-99). Thus, metastasis of colon tumors is possible in mice, but absence of Dclk1-S expression by mouse tumors may impede metastasis.

As discussed in introduction, DNA methylation and epigenetic-silencing of 5'(α)-promoters has been documented for many genes during tumorigenesis. Multiple promoters are methylated in both mouse tumors and hCRCs (Grimm et al., *PLoS Genet.* 2013, 9(2):e1003250). However, in a recent report (Borinstein et al., *Mol Carcinog.* 2010, 49(1):94-103), it was confirmed that 5'(α)-promoter of some genes (including DCLK1) are methylated and silenced in human colon tumors, but not in mouse colon tumors. Reports in literature confirm that 5'(α)-promoter of mouse Dclk1-gene does not get silenced during tumorigenesis, as confirmed (FIG. 3). In the current studies, it is further confirm that loss of DCLK1-L in hCCCs is due to DNA methylation and can be reversed with de-methylating agents (FIG. 4D and FIG. 4E). Normal human colon cell line and hNCs, on the other hand, continue to express DCLK1-L from 5'(α)-promoter. This important difference in hNCs and hCCCs was confirmed by primer-extension analysis (FIG. 4A-4C). Majority of the hCCCs/CRCs up-regulate expression of DCLK1-S from an alternate-promoter within IntronV, while mouse colon tumors do not (FIG. 3), for unknown reasons.

The underlying reason(s) contributing to the differences in methylation of 5'(α)-promoter of DCLK1-gene in human vs mouse colon tumors may reflect lack of ascorbic acid synthesis by humans, unlike mice (Venturelli et al., *Front Oncol.* 2014, 4:227). GULO (L-gulono-γ-lactone oxidase), an enzyme necessary for ascorbic acid synthesis, is mutated in primates, preventing ascorbic acid synthesis (Gabbay et al., *J Biol Chem.* 2010, 285(25):19510-20). Ascorbic acid was reported to inhibit DNA methyltransferase (Venturelli et al., *Front Oncol.* 2014, 4:227), suggesting that ascorbic acid could change epigenetic signature of cancers. It is possible that high levels of endogenous ascorbate protects mouse tissues from excessive DNA methylation (Venturelli et al., *Front Oncol.* 2014, 4:227; Gabbay et al., *J Biol Chem.* 2010, 285(25):19510-20). Alternatively, low ascorbate in humans could diminish epigenetic re-programming by Tet family of demethylases (Minor et al., *J Biol Chem.* 2013, 288(19): 13669-74). These possibilities may be clinically impactful, and need to be examined.

The activation of IntronV(β)-promoter for transcribing Dclk1-S isoform was recently described in mouse cerebellum (Pal et al., *Genome Res.* 2011, 21(8):1260-72). The use of alternate-promoters for transcribing shorter isoforms, especially for genes which have hypermethylated 5'-promoters, is a dominant phenomenon and more common than transcription of splice-variants during development and disease progression. There is thus accumulating evidence in recent literature which strongly supports the findings regarding the use of an alternate-promoter within IntronV for expressing shorter isoforms of DCLK1 in hCCCs/hCRCs. More recently, shorter isoforms of DCLK1 (47 KDa) were reported in KRAS mutant hCCCs (Hammond et al., *J Proteome Res.* 2015, 14(3):1535-46), which further supports our findings; however, the inventors did not observe a specific correlation between expression of DCLK1-S and mutant phenotype of hCCCs (Table 6).

By in silico analysis, it was discovered that while the 5'(α)-promoter was positive for functional TCF4/LEF binding sites and a few NF-κB binding sites (FIG. 5, FIG. 6, and FIG. 16), the IntronV(β)-promoter was positive for a functional NF-κB binding site, upstream of a TATA box (FIG. 7 and FIG. 8). The inventors therefore examined the role of NF-κB/β-catenin signaling pathways in regulating the activity of α/β promoters. Since progastrins activates NF-κB/β-catenin signaling pathways (Sarkar et al., *Gastroenterology.* 2011, 140(2):583-95.e4; 51. Umar et al., *Oncogene.* 2008, 27(42):5599-611; Umar et al., *J Biol Chem.* 2009, 284(33): 22274-84; Rengifo-Cam et al., *Cancer Res.* 2007, 67(15): 7266-74), resulting in increased expression of stem cell markers, including DCLK1 in normal colon crypts and transformed cells (Sarkar et al., *Int J Cancer.* 2012, 131(7): E1088-99; Sarkar et al., *Gastroenterology.* 2011, 140(2): 583-95.e4), progastrin was used for activating NF-κB/β-catenin in HEK293/HEKC cells, and examined their role in activating 5'(α)-promoter for DCLK1-L expression. Since tumorigenic/metastatic potential of HCT116/HEKmGAS cells is dependent on autocrine PG (Sarkar et al., *Int J Cancer.* 2012, 131(7):E1088-99; Singh et al., *Cancer Res.* 1996, 56(18):4111-5), these cell lines were used to examine the role of NF-κBp65 in mediating transcriptional activation of intronV(β)-promoter for expressing DCLK1-S. Experiments with Promoter-reporter constructs along with ChIP assays, in the presence or absence of siRNAs against the two transcriptional factors (FIG. 5-FIG. 8), confirmed that TCF4/LEF binding sites, in response to activated β-catenin, activates 5'(α)-promoter of Dclk1-L (in tissues such as mouse colons/tumors (Sarkar et al., *Gastroenterology.* 2011, 140(2):583-95.e4; Jin et al., *J Clin Invest.* 2009, 119(9): 2691-701), while NF-κB binding site, in response to activated NF-κBp65 and its partners, activates IntronV(β)-promoter (thus up-regulating DCLK1-S expression in hCCCs, FIG. 2 and FIG. 3, Table 6). NF-κB binding sites in the 5'(α)-promoter, on the other hand, did not appear to be playing any role in activating the (α)-promoter and/or the expression of DCLK1-L (FIG. 16). Both the 5'(α) and IntronV(β) promoters are positive for several other binding sites, which likely play synergistic/antagonistic roles in dictating transcriptional activity of the promoters.

I. BIOMARKERS

A biomarker is an organic biomolecule that is differentially present in a sample or in a cell within a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics) and of drug toxicity.

Recent advances in global scale proteomics technologies enable the detection of candidate protein biomarkers. These biomarkers include proteins, peptides, or metabolites whose measurement alone (or in a combination) would reliably indicate disease outcome. With the advancement of multi-dimensional profiling techniques, the systematic and quick identification of predictive proteins associated with a disease is now feasible.

In certain aspects, the biomarkers of this invention can be measured or detected by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

Immunohistochemistry.

In particular embodiments of the invention, the expression of biomarker in a sample is examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods.

For sample preparation, a tissue or cell sample from a mammal (typically a human patient) may be used. Examples of samples include, but are not limited to, cancer cells such as colon, breast, prostate, ovary, lung, stomach, pancreas, lymphoma, and leukemia cancer cells; or tissues, organs, or fluids that may have cancer cells. The sample can be obtained by a variety of procedures known in the art including, but not limited to surgical excision, aspiration or biopsy. The tissue may be fresh or frozen. In one embodiment, the sample is fixed and embedded in paraffin or the like. One of skill in the art will appreciate that the choice of a fixative is determined by the purpose for which the sample is to be histologically stained or otherwise analyzed.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. If paraffin has been used as the embedding material, the tissue sections are generally deparaffinized and rehydrated to water.

Optionally, subsequent to the sample preparation, a tissue section may be analyzed using IHC. IHC may be performed in combination with additional techniques such as morphological staining and/or fluorescence in-situ hybridization. Two general methods of IHC are available; direct and indirect assays.

II. KITS

In another aspect, the present invention provides kits for detecting the presence or absence of cancer cells in a sample using biomarkers described herein. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected. In yet another embodiment, the kit can comprise one or more containers with biomarker samples, to be used as standard(s) for calibration.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Reagents Used

Antibodies used in these studies included: anti-total-p65NF-κB, anti-β-catenin (total) (Cell Signaling Technology, Danvers, Mass.); anti-β-actin (total) (Sigma, St. Louis, Mo.); anti-DCLK1 antibody (Abcam AB31704, Cambridge, Mass.). Mono-specific rabbit polyclonal anti-progastrin-antibody and eukaryotic plasmid, expressing triple mutant human gastrin gene, for overexpressing human progastrin (PG) peptide, were generated as previously described (Sarkar et al., *Gastroenterology.* 2011, 140(2):583-95.e4). Smart Pool of target-specific small interfering RNA (siRNA) and non-targeting (control) siRNA Pool were purchased from Dharmacon (Lafayette, Colo.). Sepharose beads and all other chemical reagents were purchased from Sigma. TissueScan™ Disease Tissue qPCR array (Catalogue Number HCRT102) for colon cancer and normal colons was purchased from OriGene (Rockville, Md.). cDNA synthesis master mix was purchased from GeneDEPOT (Baker, Tex.). Syber green qRT-PCR kit was purchased from Bio-Rad (Hercule, Calif.). Promega GoTaq® green Master Mix (Maddison, Wis.) was used for PCR amplification, using a Thermal Cycler from Eppendorf (Hauppauge, N.Y.). Cloning vector pGL2 was from Promega, and TOPO-TA cloning vector was purchased from Invitrogen (Grand Island, N.Y.). Restriction enzymes and competent cells were purchased from New England BioLabs (Ipswich, Mass.). Transfection reagent FuGENE®6 was bought from Roche (Branford, Conn.), and all primers used were synthesized by Sigma.

Cell Culture

HEK293 and HCT116 cell lines were obtained from ATCC, and have been maintained in the laboratory for several years. CCD841 and CT26 cells were generously gifted by Dr. Carla Kantara (Department of BMB, UTMB) and Dr. Iryna Pinchuk (Department of Surgery, UTMB). CCD841 and CT26 were purchased from ATCC and confirmed by ATCC. CT26 cells were previously termed MC-26 mouse colon cancer cells. All cell lines were monitored regularly for absence of mycoplasma and HEK293 and HCT116 cell lines were confirmed to represent human epithelial cell lines with the help of Biosynthesis Company (Lewisville, Tex.). Stable clones of HEK293 cells were generated to overexpress either the control vector (HEKC) or a triple mutant hGAS vector, in order to overexpress full-length progastrin (PG) peptide (HEKmGAS cells), as described previously (Sarkar et al., *Int J Cancer.* 2012, 131(7):E1088-99; Sarkar et al., *Gastroenterology.* 2011, 140(2):583-95.e4). The HEKmGAS cells were confirmed to overexpress full-length hPG (80 AAs), as previously reported (Sarkar et al., *Int J Cancer.* 2012, 131(7):E1088-99; Sarkar et al., *Gastroenterology.* 2011, 140(2):583-95.e4). The wild type parental cell lines (HEK293, HCT116) were cultured in DMEMF medium (Invitrogen, Grand Island, N.Y.), supplemented with 10% FCS containing 1% penicillin/streptomycin in a humid atmosphere at 37° C. with 5% $CO_2$. The stable clones of HEKC and HEKmGAS cells were cultured in the same medium supplemented with 100 μg/mL Geneticin (Invitrogen) under similar conditions. CCD841 and CT26 were similarly cultured using MEM (CCD841) and RPMI-1640 (CT26), media, along with supplements as described above. In addition, for screening purposes only, several panels of human colon cancer cell lines were purchased from ATCC, and maintained in culture as suggested by the company.

Procurement of Samples from Normal Colonic Mucosa and Colonic Tumors of Patients Samples of normal colonic mucosa were obtained from consented patients at the time of endoscopy for screening purposes, as per our approved IRB protocol (IRB#03-237). Normal samples were obtained only if the colons were free of adenomas (Ads) and adenocarcinomas (AdCAs), but positive for small hyperplastic (Hp) growths. Pinch biopsies of tubular adenomas (TAs) (polyps) were also obtained at the time of screening endoscopy, from patients who were positive for polyps but negative for AdCAs, as per approved IRB Protocols; the rest of the snared polyps were sent to pathology department. Samples of primary or metastatic tumors, with or without the adjoining uninvolved colonic tissue (matched paired sample) were obtained as discarded samples (as per our approved IRB protocol #91-310) from either UTMB Hospital, at time of surgery, or from Tissue Core Facility at Cancer Center, University of Alabama, as part of CHTN Program funded by NIH. All samples were collected and flash-frozen and stored in liquid nitrogen or −80° C. until analyzed. Pathology of all samples, thus obtained, was confirmed. In few experiments tissue samples were harvested from colons, liver, and brain of male FVB/N mice (2-4 month old) (Taconic, Hudson, N.Y.) by published methods (Cobb et al., Cancer. 2004, 100(6):1311-23). Ninety-two colorectal carcinoma tissues were used for clinical validation of DCLK1-S expression from an independent cohort, for data presented in FIG. 9 and Tables 7 and 8. These specimens were preserved immediately after surgical resection in RNA later (QIAGEN, Chartsworth, Calif.) and stored at −80° C. until RNA extraction. The surgical samples were obtained from the Mie University Hospital, Japan, from patients enrolled during 2005 to 2011. The patients included 57 men and 35 women with a mean age of 68 years (range 37-89 years). None of the patients received chemotherapy and radiotherapy before surgery and no perioperative mortalities were observed. The primary lesion was located in the rectum in 41 patients, sigmoid colon in 19, ascending colon in 16, transverse colon in 9, and descending colon in 7. Eleven patients were diagnosed with synchronous liver metastasis. Clinicopathological findings were based on the UICC's criteria for tumor node metastasis (TNM) classification. There were 19 patients with stage I (T1-2N0M0), 30 with stage II (T3-4N0M0), and 22 with stage III (TXN1-2M0) disease. Twenty-one patients with distant metastasis were classified as having stage IV (TX-NXM1) disease. Ten patients had poorly differentiated or mucinous adenocarcinoma, whereas 82 patients had well or moderately differentiated colorectal tumors. Postoperative follow-up data were obtained from all patients, and the median follow-up duration was 21.8 months (range: 1-88). All patients were followed up after the initial hospital discharge, with physical examination and tumor marker assays (CEA, CA19-9) performed every 1-3 months and computed tomography performed every 6 months. Endoscopic examinations were performed when necessary. Written informed consent was obtained from each patient (as per approved IRB protocol #005-134).

Analysis of Tissue Samples and Cell Lines by RT-PCR/qRT-PCR

Total RNA was isolated from cell lines in monolayer cultures at 60-70% confluency, or from human and mouse tissues (described above), using Trizol Reagent (Invitrogen), as previously described (Singh et al., Oncogene. 2007, 26(3):425-40). Briefly, 2 µg of total RNA was reverse transcribed, using cDNA Synthesis Master Mix (GenDEPOT, Tex.). The product was diluted (1:10) and used for amplification by either quantitative (q) or regular PCR. For qRT-PCR, the iTaq Universal SYBR Green Supermix (Bio-Rad, CA) was used as per the manufacturer's instructions. Expression levels of DCLK1-S in tissues for data presented in FIG. 9 were normalized against GAPDH using the 2-ACt method, as previously described (Hur et al., Gut. 2014, 63(4):635-46). The primer sequences used for PCR amplification of cDNA for both RT-PCR/qRT-PCR amplification of the long (L) and short (S) isoforms of DCLK1 from either human (h) or mouse (m) specimens are provided in Table 4. Relative band-density of electrophoresis blots was analyzed using Image J program (rsbweb.nih.gov/ij/download) and expressed as a ratio or % of β-actin in the corresponding samples.

3'-5' Primer-Extension-Assay

Total RNA was extracted from HCT116 and HEK-293 cells as described above. Nascent RNA was isolated using a Click-iT Nascent RNA Capture Kit (Life Technologies) according to the manufacturer's instructions. 5 µg of total RNA or nascent RNA was reverse transcribed using a DCLK1-common primer (primer 2 in FIG. 4A), that encompassed the nucleotide sequence from homologous coding sequence of both long and short isoforms of DCLK1. The pool of cDNA was purified using a column (Oligo Clean & Concentrator, Zymogen). The purified cDNA was ligated to a non-mammalian adapter sequence (atgctgaaacgcgagagaaaccgcgtatcaacccc (SEQ ID NO:2)) at the 5'-end by T4 DNA ligase followed by purification of the ligated cDNA product. 2 µl of the ligated product was PCR amplified using the forward adapter primer (primer 1) and reverse primer 2. Using these primers, the expected size for the DCLK1-S transcript is 498 bps (NM_001195415.1) and for the DCLK1-L transcript is 1300 bps (NM_004734.4) as shown in FIG. 4A.

Treatment of Colon Cancer Cells with 5-Azacytidine (De-Methylating Agent)

HCT116 cells were seeded in 100 mm dishes at a density of $5\times10^6$ cells/dish, one day prior to drug treatment. The cells were treated with 10 µM 5-aza-2'-deoxycytidine (5-Azacytidine) on days 2 and 5 of culture. The cells were harvested on day 6 of culture and total RNA isolated. RNA was processed for measuring relative levels of DCLK1-L/S by RT-PCR.

Generation of DCLK1 5'(α)-Promoter-Reporter (Luciferase) Constructs

The long isoform (Isoform 1) of human DCLK1 is transcribed from 5'-promoter (NM_004794.4). Based on the published promoter sequence (AL160392.12), several primer sets were designed to amplify three promoter segments of 0.5 to >2.0 Kb of the 5'-promoter from −100 through −2234 nucleotides using genomic DNA from either normal colonic mucosa or HEK-293 cells, which gave identical results. The primers were synthesized with the restriction sites XhoI at 5'-end and HindIII at 3' end, in order to clone into PGL2 basic vector (as shown in Table 4). The PCR products were purified using QIAquick PCR Purification kit (Qiagen, Valencia, Calif.), cloned into luciferase expression vector (PGL2 basic vector, Promega, Wis.) and amplified in DH5α competent cells (New England Biosciences, MD). Positive colonies were processed for purifying the promoter-reporter expression plasmids; control plasmids lacked the DCLK1 5'-promoter sequences. In initial experiments promoter-reporter plasmids were transfected into HEK-293/HEKmGAS and HCT116 cells, and the construct which demonstrated the maximum luciferase activity (−2234/−504 promoter-luciferase construct) (termed DCLK1-L-LUC), was used in all the studies presented in FIG. 5.

Generation of Promoter-Reporter Constructs for IntronV-(β)Promoter of DCLK1-Gene The short isoform of DCLK1 (isoform 2) (NM_001195415.1) is transcribed from a promoter within intron-V, as recently reported for neuronal cells (Le Hellard et al., *PLoS One.* 2009, 4(10):e7534). Unlike the 5'-promoter, the intron-V promoter has a consensus TATA binding site at −918 nt (FIG. 7A), and promoter-reporter constructs surrounding the TATA box have been shown to be active in promoter-reporter assays (Le Hellard et al., *PLoS One.* 2009, 4(10):e7534). Therefore, promoter fragments within intron-V (−2503/−771 and −1348/−771) were amplified using genomic DNA and cloned into PGL2 basic vector as XhoI and HindIII sites. The purified intron-V promoter-reporter constructs, DCLK1-Luc-S1 (−2503/−771) and DCLK1-Luc-S2 (−1348/−771), were confirmed by DNA sequencing. Primer sequences used for PCR amplification of the promoter segments are listed in Table 4.

lysis buffer and luciferin was added according to instructions of the manufacturer (E2510, Promega Wis.). Luciferase activity was measured using a luminometer (Dynex Technologies, VA) after 10 sec of addition of substrate.

Chromatin Immunoprecipitation Assays (ChIP)

For ChIP assays, cells were cultured in 100 mm dishes until the cells were 60-70% confluent, and fixed in 1% formaldehyde for 10 min to crosslink DNA to bound proteins. The crosslinking reactions were stopped by adding glycine at final concentration of 0.125 M. Cells were washed with cold PBS, scraped with a rubber policeman into 500 μl of PBS+protease inhibitor cocktail (Sigma) and centrifuged

TABLE 4

Primer Sequences Used for RT-PCR/qRT-PCR and Other Assays

| Target cDNA/gDNA | Species | Primer Sequence | Assay |
|---|---|---|---|
| DCLK1-Long (cDNA) | Human | F:GGAGTGGTGAAACGCCTGTAC (SEQ ID NO: 3)<br>R:GGTTCCATTAACTGAGCTGG (SEQ ID NO: 4) | RT-PCR &<br>qRT-PCR |
| DCLK1-Short (cDNA) | Human | F:ACACTAAGACTGTGTCCATGTTAGAACTC (SEQ ID NO: 5)<br>R:AAGCCTTCCTCCGACACTTCT (SEQ ID NO: 6) | RT-PCR &<br>qRT-PCR |
| DCLK1-Long (cDNA) | Mouse | F:TCAATGAGGACCAGCTCCAG (SEQ ID NO: 7)<br>R:TCCGAGAGAGTTCGGGTCA (SEQ ID NO: 8) | RT-PCR &<br>qRT-PCR |
| DCLK1-Short (cDNA) | Mouse | F:AAGACGTCAGCCTTACGCAG (SEQ ID NO: 9)<br>R:GAGAGATCCTCTGCTTCCGC (SEQ ID NO: 10) | RT-PCR &<br>qRT-PCR |
| −1443 TCF cis element in 5' promoter (gDNA) | Human | F:AGAGCTGTGTCTGCTTGG (SEQ ID NO: 11)<br>R:GTTCATTCCAGGGCAGCTTA (SEQ ID NO: 12) | ChiP PCR |
| −1443 TCF cis element in 5' promoter (gDNA) | Human | F:TAAGCTGCCCTGGAATGAAC (SEQ ID NO: 13)<br>R:CCCAAGCTATGCACTCTGGT (SEQ ID NO: 14) | ChiP PCR |
| NF-κB cis element in intron V promoter (gDNA) | Human | F:CTGTATCCACTGCCCTCTGT (SEQ ID NO: 15)<br>R:GCAAAGCTATCTTCAGGAGG (SEQ ID NO: 16) | ChiP PCR |
| DCLK1-5' promoter (−1067/−650) (gDNA) | Human | F:TTTAGGGGTGTAGTTAAGTTAGATG (SEQ ID NO: 17)<br>R:AACCTCTCTCTCCAAAAAAAA (SEQ ID NO: 18) | DNA methylation of CpG sites |
| DCLK1-L-Luc (−2234/−503) (gDNA) | Human | F:ACATGACTGTGGGCAAATGA (SEQ ID NO: 19)<br>R:CCCAAGCTATGCACTCTGGT (SEQ ID NO: 20) | Promoter Reporter Construct |
| DCLK1-S-Luc1 (−2503/−771) | Human | F:GGTGCTTCCGTTCAAAGTGT (SEQ ID NO: 21)<br>R:CAGTCTCAGGAATACCTTGC (SEQ ID NO: 22) | Promoter Reporter Construct |
| DCLK1-S-Luc2 (−1348/−771) | Human | F:CCTCCTGAAGATAGCTTTGC (SEQ ID NO: 23)<br>R:CAGTCTCAGGAATACCTTGC (SEQ ID NO: 24) | Promoter Reporter Construct |
| Primer 1-Adaptor<br>Primer 2-DCLK1 common | Human<br>Human | F:GAGAACCGCGTATCAACCCC (SEQ ID NO: 25)<br>R:GTGACGTAGAGGAGCCGCCA (SEQ ID NO: 26) | LM-PCR<br>LM-PCR |

Promoter-Reporter Assays

Cells were transiently transfected with the indicated promoter-reporter constructs using FuGENE6 for 24-48 hrs, as per manufacturer's instructions; control cells were transfected with empty pGL2 vector, lacking promoter sequences. In some experiments promoter-reporter plasmids were used for measuring activation of β-catenin (TOPFlash wild type and FOPFlash mutant), obtained from Dr. Bert Vogelstein (John Hopkins, Baltimore, Md.), as previously described (Sarkar et al., *Gastroenterology.* 2011, 140(2): 583-95.e4). Transfected cells were lysed in luciferase assay for 5 min at 400 g at 4° C. The supernatant was discarded and the cells were suspended in 600 μl of ChIP sonication buffer (1% Triton X-100, 0.1% deoxycholate, 50 mM Tris-pH 8.1, 150 mM NaCl, 5 mM EDTA and protease inhibitors). Crosslinked chromatin DNA was then sonicated to obtain an average fragment length of 600-700 bp and centrifuged at 10,000 RPM for 10 min at 4° C. The crosslinked chromatin supernatant was immunoprecipitated using target-specific antibody (2-5 μg purified IgG) at 4° C. overnight in a rotator. Control samples contained no antibody. For obtaining input levels of the corresponding proteins, equivalent numbers of cells were also processed for Western Immunoblot analysis of the indicated proteins as described below. After the incubation, 30 μl of protein A/G Sepharose beads, pre-absorbed by Herring sperm DNA (100 μg/ml) was added to the chromatin-antibody complex and incubated for additional 3-4 hrs in a rotator at 4° C. The samples were centrifuged at 2500 RPM for 5 min at 4° C. to sediment the beads. The beads were washed three times with 1 ml of cold ChIP buffer and two washes with 1 ml cold PBS. DNA was eluted from the beads by adding 100 μl of elution buffer (1% SDS, 0.1% NaHCO$_3$, 0.01 mg/ml Herring Sperm DNA) and incubating for 30 min at room temperature in a rotator, followed by centrifugation at 2500 RPM for 5 min at room temperature. DNA in the supernatant was precipitated using the high-salt method. The extracted DNA was purified using a kit from Zymogen (Catalog number D4060), and 2 μl of the purified DNA was used for PCR amplification of the immunoprecipitated DNA with specific primers designed around the transcription factor binding site of interest. The primer sequences used for this purpose are listed in Table 4.

DNA Methylation Analysis Using the Method of Bisulfite Conversion

Genomic DNA was purified from cell lines and colon tissues using a kit from Qiagen, and 2-5 μg of gDNA was used for methylation analysis. Methylation analysis was conducted as described by Clark et al (Clark et al., *Nucleic Acids Res.* 1994, 22(15):2990-7). Briefly, DNA was treated with sodium hydroxide (3M) for denaturation followed by bisulfite deamination using hydroquinone/sodium bisulfite treatment (16 mM hydroquinone, 4 M sodium bisulfite), overnight at 50° C. The reaction mixture was desalted using Wizard DNA clean-up kit (Promega) and NaOH (3.0 M), followed by incubating at 37° C. for 20 min for alkali de-sulphonation reaction. The DNA was precipitated in the presence of 10 mg/ml glycogen as a carrier. Bisulfite converted DNA (2 μl) was amplified by PCR using bisulfite converted primers (primers used are listed in Table 4). The PCR products were purified by a column (Wizard DNA clean-up kit, Promega) and cloned into a TA cloning vector (Sigma). Clones were confirmed by EcoR1 digestion and positive clones were sequenced using T7 primers in the recombinant DNA Core Facility at UTMB.

Western Immunoblot (WB) Analysis

Treated and control cells growing as mono-layer cultures, were harvested and processed for preparing cellular-lysates, followed by electrophoresis and transferred to PVDF-membranes. Frozen tissue samples obtained from patients as described above were homogenized and processed for preparation of tissue lysates in RIPA buffer. Samples containing 30-50 μg of proteins were subjected to electrophoresis and transferred to PVDF-membranes. Blots were cut into horizontal strips containing target or loading-control proteins ((β-actin), and processed for WB. Antigen-antibody complexes were detected with a chemiluminescence-reagent kit (Thermoscientific, IL or GE Healthcare, UK). Membrane-strips containing either target or loading control proteins were simultaneously exposed to autoradiographic films. Relative band-density on scanned autoradiograms was analyzed using Image J program and expressed as a ratio or % of β-actin in the corresponding samples.

Transient-Transfection of Cells with Oligonucleotides

Cell lines, seeded in 96-well plates were transfected with 5 pmol of either target-specific or control-siRNA, as indicated, using Lipofectamine™ 2000 (Invitrogen). Transfected cells were propagated in normal growth medium containing 10% FCS, and processed for WB analysis after 48 hrs of transfection for confirming down-regulation of the target transcription factor (β-catenin or NF-κBp65). In order to examine the role of the indicated transcription factors in modulating the transcriptional activation of the promoter-reporter constructs, cells in culture were pre-transfected with the indicated promoter-reporter constructs, followed by transient transfection with the indicated siRNA molecules, followed by processing the cells after 48 hrs of treatment for relative levels of luciferase.

Statistical Analysis

Data are presented as mean±SEM of values obtained from indicated number of patient samples or experiments. To test for significant differences between means, nonparametric Mann Whitney test was employed using STAT view 4.1 (Abacus Concepts, Inc, Berkley, Calif.). Chi-square tests were used to analyze the relationship between DCLK1-S expression and clinicopathological factors. Overall survival curves were analyzed using Kaplan-Meier method, and comparisons were made using the log-rank test. The cut off threshold between high and low expression group for DCLK1-S transcript was defined by the median values of the gene's expression in cancerous tissue. The cox proportional hazards regression model, using Medcalc version 12.3.0 was utilized to estimate univariate and multivariate hazard rations for prognosis. In addition to target mRNA expression, a list of clinical variables was considered for univariate and multivariate analysis to determine its impact on prognosis of patients with colorectal cancer: sex, age at diagnosis (continuous), pathological differentiation (differentiated or undifferentiated), tumor size (>41 mm median or <41 mm), lymph node metastasis (present or absent), and distant metastasis (presence or absence). All p values were two-sided and differences were considered to be statistically significant if <0.05.

Results

5'-(α)Promoter is Methylated During Colon-Carcinogenesis in Humans

In preliminary studies it was discovered that 5'(α)-promoter of DCLK1-gene was hypermethylated in hCCCs. A total of 20 CpG sites were mapped within 200 bps of the 5'(α)-promoter (FIG. 1A). All 20 CpG sites were non-methylated in the human normal colon (hNC) cell line (CCD841), but were methylated by >80% in hCCC-lines. Mapping of the methylation status of individual CpG sites obtained from representative cell lines by bisulfite sequencing is diagrammatically presented in FIG. 1B. Samples obtained from either normal (Norm) colons, adenomas (Ad), adenocarcinomas (AdCA) or metastatic-lesions (Met), from 5-8 patients, were also analyzed for methylation status of the indicated CpG sites and data from representative samples are presented diagrammatically in FIG. 13. The percentage of 20 CpG sites, that were methylated in all the samples examined, was in the order of: AdCA/Met(85±15)>TA (67±30)>Norm (19±8%) (FIG. 1C).

Human Normal Colons (hNCs)/Cells Mainly Express Long-Isoform of DCLK1 while hCCCs/hCRCs Mainly Express Short-Isoform Hypermethylation of 5'-promoter of some genes during neoplastic-transformation is associated with expression of shorter transcripts from an alternate promoter (Archey et al., *Cancer Res.* 1999, 59(10):2292-6; Hoivik et al., *PLoS One.* 2013, 8(7):e67925). Since 5'(α)-promoter of the DCLK1-gene is hypermethylated in hCRCs, but DCLK1 protein is measured in hCRCs, usage of an alternate-promoter was suggested.

Figures 2A, 2B, 2C, 2D, 2E, 2F:
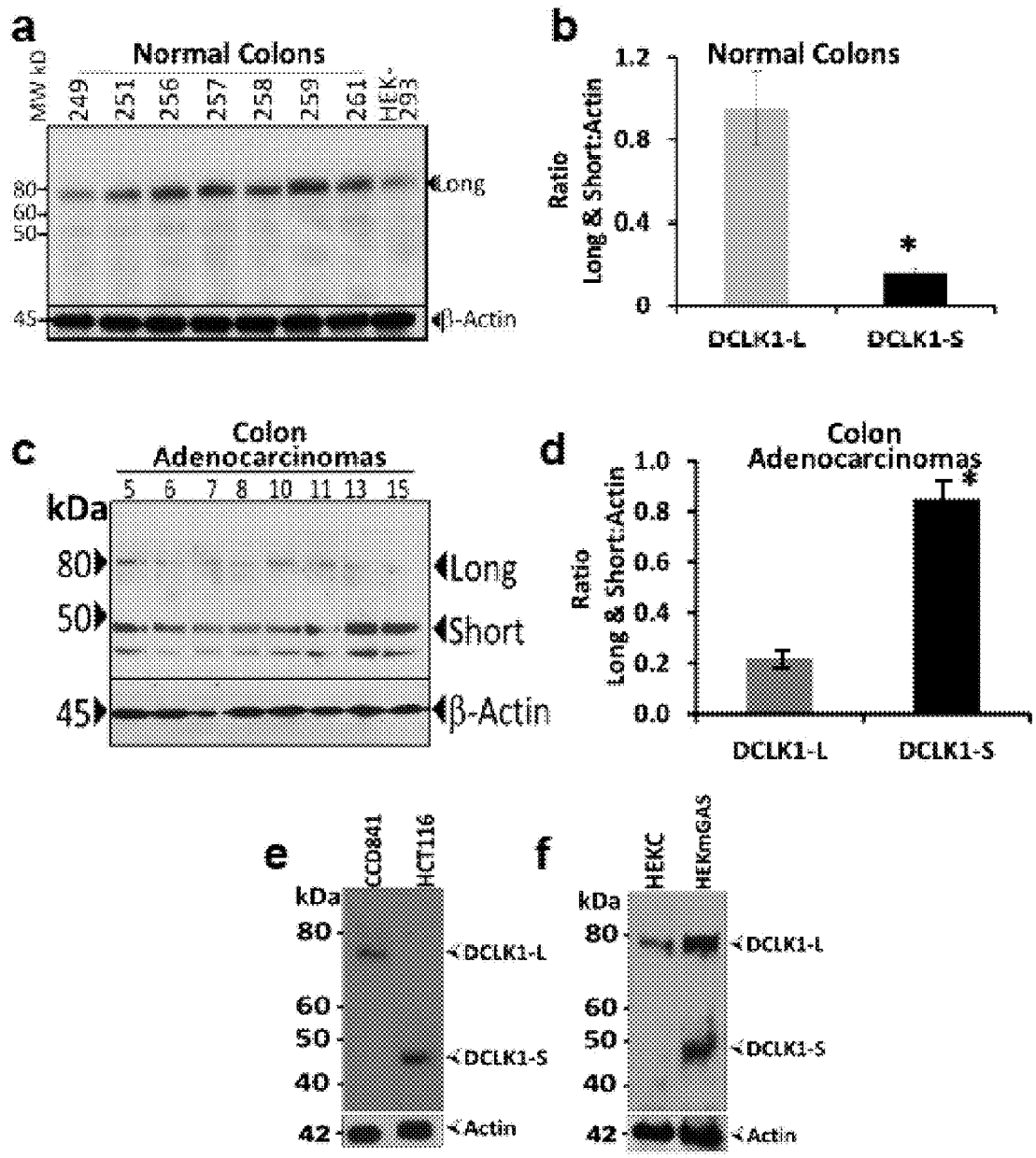

Molecular mass of DCLK1 was determined by Western Blot (WB) analysis using DCLK1-antibodies, which detect isoforms 1 and 2 in human brain. Almost all normal colonic mucosal samples (hNC) from patients were positive for the ~82 kDa DCLK1 protein, corresponding to long isoform of hDCLK1; Less than 10% samples (1/22) were also strongly positive for S-isoform (Table 5), which may be of prognostic value, since the patient was positive for large adenomas. Representative WB data from hNC patient samples are presented in FIG. 2A. A minor band of S-isoform was also seen in a few hNC samples, which may reflect expression of the short isoform by stromal and enteric neuronal cells, present within the colonic mucosa. The AdCA samples from patients with hCRCs were predominantly positive for ~45-48 kDa DCLK1 protein, corresponding to short (S) isoform of hDCLK1. Representative WB data from AdCA samples in presented in FIG. 2C. The ratios of S/L DCLK1 to β-actin in hNCs vs hCRC samples, demonstrated opposite profiles (FIGS. 2B and 2D). A hNC cell line (CCD841) only expressed DCLK1-L while HCT116 hCCC only expressed DCLK1-S (FIG. 2E). All 15 hCCC cell-lines, examined by RT-PCR, were negative for DCLK1-L; but the majority (13/15) expressed DCLK1-S (Table 6). Representative RT-PCR data from hCCC cell-lines, wild type or mutant for KRAS/BRAF, are presented in FIG. 14; the expression of DCLK1-S did not appear to be associated with any specific mutant phenotype of hCCC-cell line. HEK293 cells, transduced to over-express progastrin (HEKmGAS), develop tumorigenic/metastatic potential, and express elevated levels of both S/L DCLK1; control non-tumorogenic, HEKC cells, however, only express DCLK1-L (FIG. 2F). Thus, tumorigenic-transformation alone can apparently up-regulate the expression of the short-isoform, in the absence of epigenetic-silencing of 5'(α)-promoter.

Table 5 shows the relative expression of DCLK1-L/S in normal colonic mucosa samples from indicated patients by Western blot Analysis. Relative band density of normal colonic mucosa samples was analyzed using Image J. Samples which expressed similar concentrations as HEK293 cells, used as positive control, were arbitrarily labeled as ++; samples which expressed significantly higher (>1.5 fold higher) were labeled as +++; samples which expressed less than 50% of that in HEK293 cells were labeled +, and those that expressed<20% of that measured in HEK293 cells were labeled ±; samples with no detectable expression, similar to that in HCT116 cells were labeled −. Only one normal colon mucosal samples from patient 262, appeared to be negative for both S/L isoforms, which could be due to possible degradation of the sample, since samples after endoscopic collection, are usually flash frozen within 5 min, but due to logistics can remain at room temperature for longer than 10 min, before flash freezing, as described.

TABLE 5

Relative Expression Of DCLK1-L/S In Normal Colonic Mucosal Samples From indicated Patients By Western Blot Analysis.

| Patient# | Pathology | DCLK1-L | DCLK1-S |
|---|---|---|---|
| UTMB-224 | No Growths | +++ | − |
| UTMB-225 | No Growths | +++ | + |
| UTMB-235 | TA | +++ | ++ |

TABLE 5-continued

Relative Expression Of DCLK1-L/S In Normal Colonic Mucosal Samples From indicated Patients By Western Blot Analysis.

| Patient# | Pathology | DCLK1-L | DCLK1-S |
|---|---|---|---|
| UTMB-236 | No Growths | +++ | − |
| UTMB-237 | No Growths | +++ | − |
| UTMB-238 | No Growths | +++ | − |
| UTMB-239 | No Growths | +++ | − |
| UTMB-240 | No Growths | +++ | − |
| UTMB-249 | No Growths | ++ | − |
| UTMB-251 | No Growths | ++ | − |
| UTMB-256 | No Growths | +++ | − |
| UTMB-257 | No Growths | +++ | − |
| UTMB-258 | No Growths | ++ | − |
| UTMB-259 | No Growths | +++ | − |
| UTMB-261 | No Growths | +++ | − |
| UTMB-262 | No Growths | − | − |
| UTMB-263 | No Growths | +++ | ± |
| UTMB-264 | No Growths | +++ | + |
| UTMB-265 | No Growths | +++ | + |
| UTMB-266 | No Growths | +++ | + |
| UTMB-267 | No Growths | + | ± |
| UTMB-268 | No Growths | ++ | − |

Table 6 summarizes RT-PCR analysis of long and short transcript of DCLK1 in human colon cancer cell lines. DCLK1-L and S primers were used to identify the isoforms being expressed by 15 colon cancer cell lines. The cell line name, ATCC catalog number, and mutational status of each cell line is provided. Most of these cell lines were purchased from ATCC. Cells positive for either DCLK1-L or S are represented by + sign, while cells negative for DCLK1-L or S are represented by − sign.

TABLE 6

RT-PCR analysis of long and short transcript of DCLK1 in human colon cancer cell lines.

| Cell Line | ATCC # | DCLK1 LONG | DCLK1 SHORT | Mutant Gene(s) |
|---|---|---|---|---|
| LOVO | CCL-229 | − | + | APC KRAS[13], MSH2 |
| SW1116 | CCL-233 | − | + | APC, KRAS[12], TP53 |
| SW837 | CCL-235 | − | + | APC, KRAS[12], TP53 |
| SW948 | CCL-237 | − | + | APC, APC, KRAS[61], PIK3CA |
| HCT116 | CCL-247 | − | + | KRAS[13], PIK3CA |
| SW-480 | CCL-228 | − | + | APC, KRAS[12], SMAD4 |
| DLD1 | CCL-221 | − | + | APC, KRAS[13], PIK3CA, TP53 |
| COLO205 | CCL-222 | − |   | APC, BRAF, SMAD4, TP53 |
| RKO | CRL-2577 | − | + | BRAF, PIK3CA |
| LS411N | CRL2159 | − | + | APC, BRAF, TP53 |
| SW1417 | CCL-238 | − |   | APC, BRAF, PIK3R1, TP53 |
| HT29 | HTB-38 | − | + | APC, BRAF, PIK3CA, SMAD4, TP53 |
| NCIH508 | CCL-253 | − | + | BRAF, PIK3CA, TP53 |
| Caco2 | HTB-37 | − | + | APC, SMAD4, W533 |
| COLO320 | CCL-320 | − | + | APC, TP53 |

Genomic structure of hDCLK1-gene was mapped from contig NC_40000013.1 (FIG. 3A). Primer sets were designed for isoforms listed in NCBI database, to identify the isoforms being expressed by normal (CCD841/HEKC) and transformed (HCT116/HEKmGAS) cells. Long (NM_004734.4) and short (NM_001195415.1) transcripts, transcribed from the indicated exons (FIG. 3A), were detected (FIGS. 3B and 3C). Only the 5'UTR and 17 bps, downstream of ATG, are non-homologous in S vs L transcripts; the rest of the coding sequence for DCLK1-S is homologous with DCLK1-L (FIG. 3A and FIG. 10). Amino acid sequence of DCLK1-S was also >98% homologous with C-terminus of DCLK1-L (FIGS. 11A and 11B). The mouse Dclk1-gene and its associated transcripts are presented in FIG. 12, demonstrating complexity of this gene in different species. The slight differences in nucleotide sequences of L/S DCLK1 were exploited, and used to develop isoform specific primers for amplifying L/S transcripts from human/mouse samples (Table 4). HCT116 cells only expressed DCLK1-S, while normal CCD841 cells only expressed L-transcript (FIG. 3B). Non-tumorigenic HEKC cells only expressed L-transcript, while tumorigenic/metastatic HEKmGAS cells expressed both DCLK1-L/S (FIG. 3C), corresponding to protein data (FIG. 2F). Both L/S transcripts were expressed in mouse brain (FIG. 3D), as reported (Omori et al., *J Hum Genet.* 1998, 43(3):169-77), but mouse colonic epithelium only expressed Dclk1-L (FIG. 3D). Unlike hCRCs, 5'-promoter of mDclk1 gene does not appear to be epigenetically silenced in intestinal/pancreatic tumors. Norm/Ad samples from mouse colons (generated as described in methods), were subjected to RT-PCR, using mouse primers (Table 4), and only L-transcript was amplified in both (FIG. 3E). In a mouse cancer cell line (CT26), only L-transcript was amplified (FIG. 3F). Thus, even though 5'-promoter of many common genes are epigenetically silenced in both mouse/human colon tumors, 5'($\alpha$)-promoter of hDCLK1 gene is silenced in human colon tumors. The loss or gain of DCLK1-L/S transcripts during different stages of colon-carcinogenesis was examined in patient samples, and representative RT-PCR data are presented in FIG. 15A. Data from all samples (FIGS. 3G and 3H), show that hNCs from patients mainly express L-transcript, while adenomas/adenocarcinomas mainly express S-transcript, albeit at significantly different levels. Thus loss of DCLK1-L is an early event, resulting from epigenetic-silencing of 5'($\alpha$)-promoter in TA samples (as shown above in FIG. 1C), while DCLK1-S expression is incrementally increased during carcinogenesis (FIG. 15A). The fold-change in DCLK1-S expression by hCRC samples, at stages I-III, was examined by qRT-PCR, compared to that in hNCs, free of colonic growths (FIG. 15B); higher levels were measured at stages I/II than stage III in the four samples analyzed/stage, using a commercial cDNA plate.

Identification of Transcriptional Start Site of DCLK1-Transcripts in Normal Vs Cancer Cells A common reverse-primer (primer-2) from coding sequence of L/S transcripts was designed (Table 4), and either nascent-mRNA or total-RNA was reverse transcribed, as diagrammatically shown (FIG. 4A). A non-mammalian adapter-sequence was ligated to the products and PCR amplified using primers ½ (FIG. 4A); results are shown in FIGS. 4B and 4C. HCT116 cells only expressed a 498 bp-product, matching the expected size of short-isoform (NM_001195415.1)(FIG. 4B). HEK293 samples only expressed a 1,300 bp-product, matching the expected size of DCLK1-L transcript (NM_004734.4)(FIG. 4C). Sequencing confirmed the expected products. All other bands were fragments or non-specific. The results confirm that hCCCs express DCLK1-S from the β promoter in intron-V of hDCLK1-gene. HCT116 cells, treated with 5-Azacytidine, re-expressed DCLK1-L transcript (FIGS. 4D and 4E), confirming that 5'-promoter of hDCLK1 gene is epigenetically-silenced in HCT116 cells.

Figures 5A, 5B, 5C, 5D, 5E:
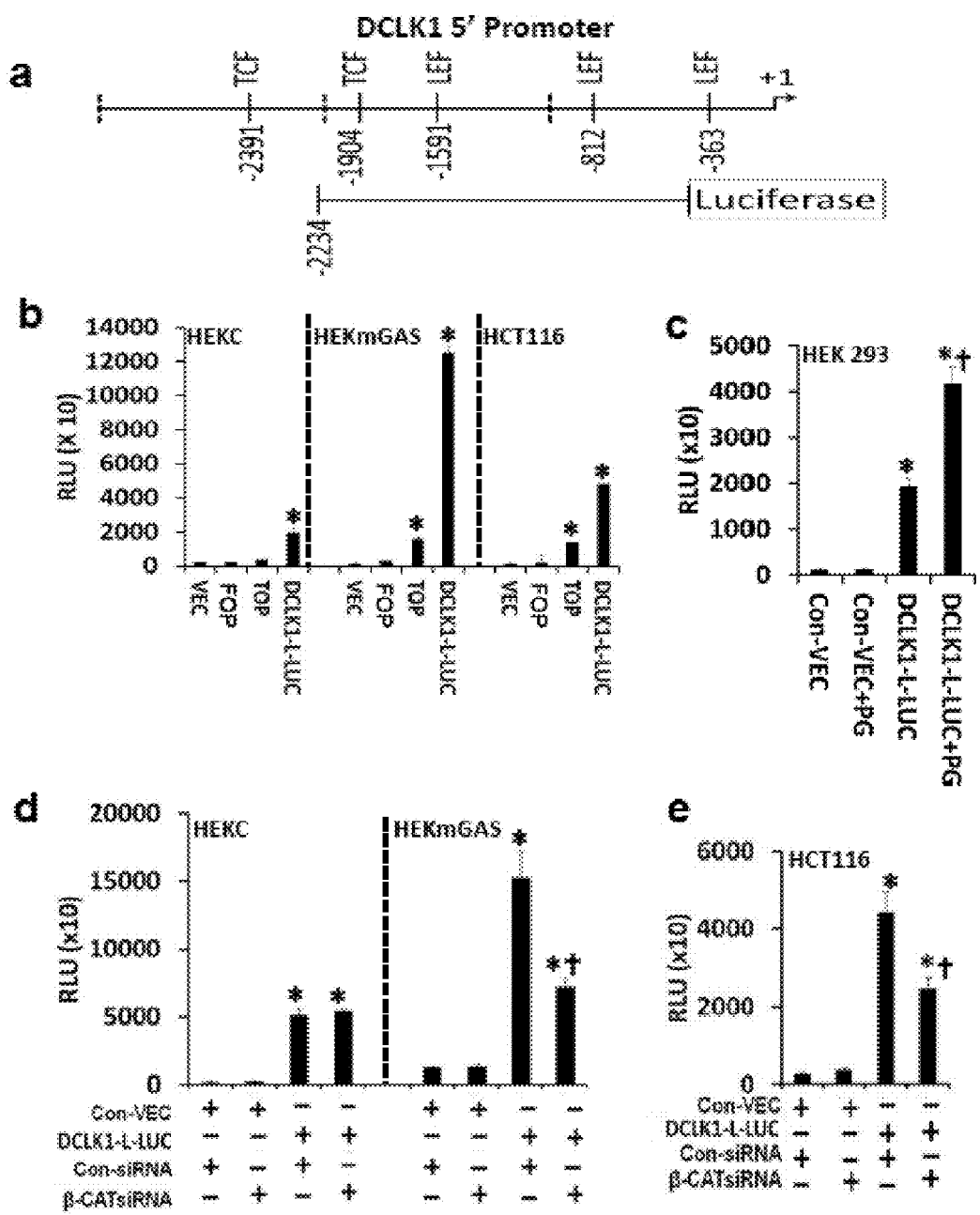
Figures 6A, 6B, 6C, 6D, 6E, 6F, 6G:
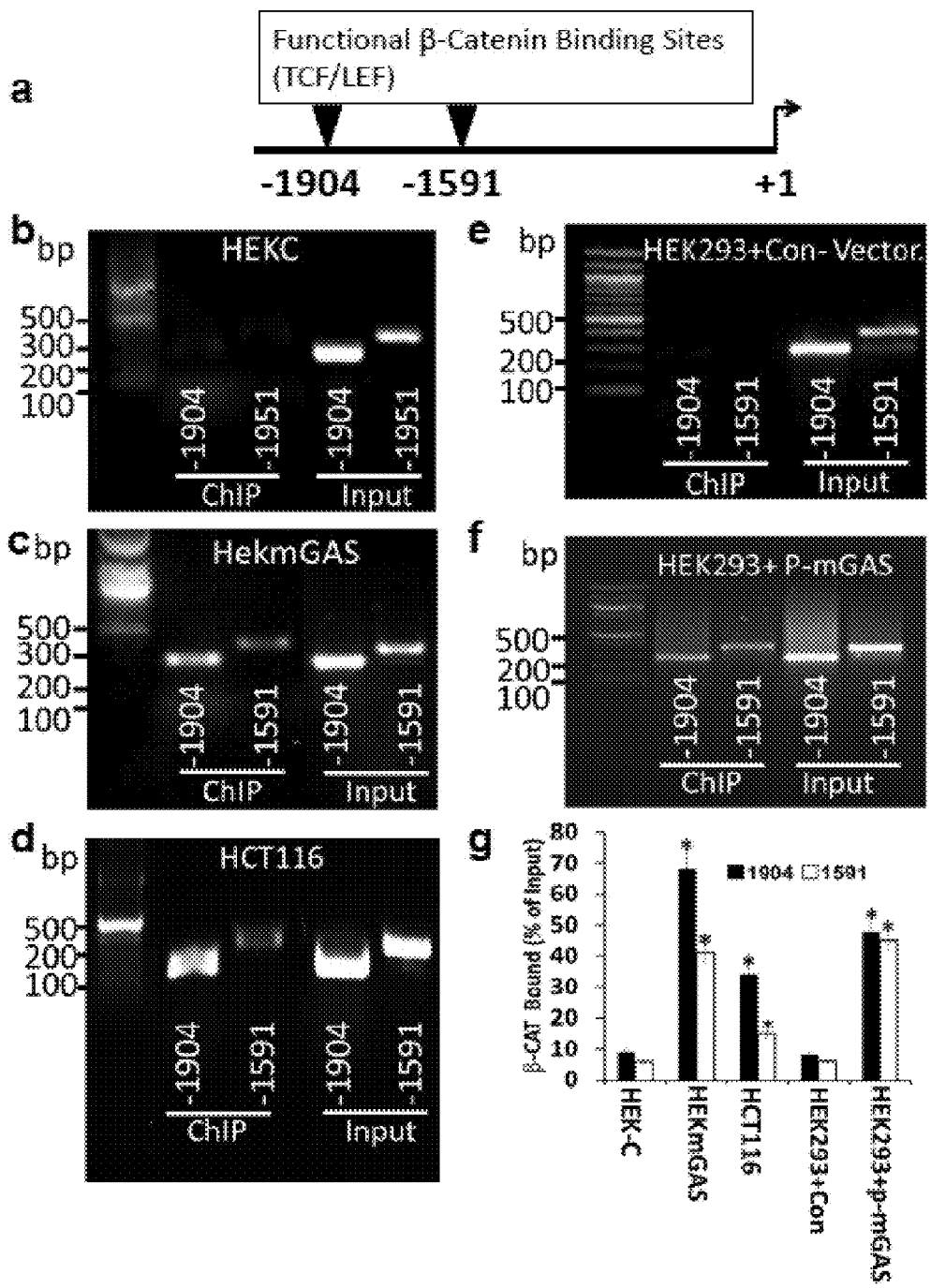
Figures 16A, 16B, 16C, 16D:
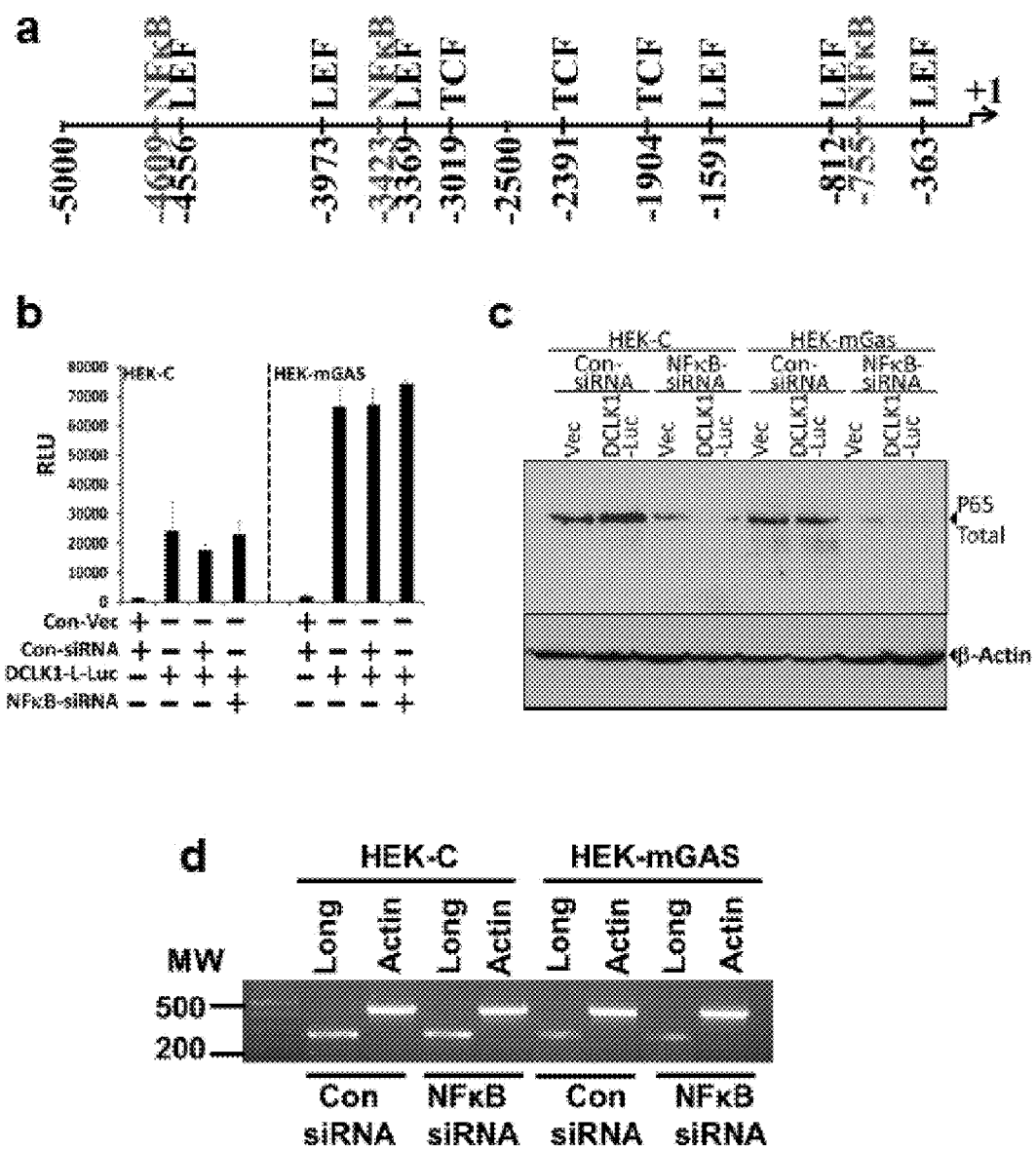

Role of TCF4/LEF Binding-Sites in Up-Regulating Transcriptional Activity of 5'($\alpha$)-Promoter of hDCLK1 Gene Progastrin (PG) was used as an activator of DCLK1 expression in target cells. PG is a potent co-carcinogen and increases colon-carcinogenesis in mice, in response to AOM±DSS. Two potent transcription-factors (TFs) (NF-κBp65/β-catenin) mediate hyperproliferative/co-carcinogenic effects of PG on mouse colonic crypts, associated with significant up-regulation of stem-cell-markers, including DCLK1. Since colon-carcinogenesis in mice is associated with increased expression of Dclk1-L (FIG. 3), and NF-κB/β-catenin mediate up-regulatory effects of PG, in silico analysis of 5'($\alpha$)-promoter was conducted. Several potential binding-sites for TCF4/LEF, and NF-κB, were found within 5 kb of start-site (FIG. 5A and FIG. 16A). A 5'-promoter-reporter construct, containing TCF4/LEF and NF-κB binding-sites, was generated. Relative transcriptional-activity of promoter-reporter construct was examined in transiently transfected HEKC/HEKmGAS/HCT116 cells (FIG. 5B). CCD841 cells were not used as they were difficult to transfect. Corresponding levels of activated β-catenin were indirectly examined by measuring relative activation of TOP vs FOP plasmids. Non-tumorigenic HEKC cells demonstrated relatively low levels of activated β-catenin (TOP-activity), while HEKmGAS/HCT116 cells were positive for significant levels of activated β-catenin/NF-κB (FIG. 5B and FIG. 16B), probably in response to autocrine PG. Transcriptional activity of 5'($\alpha$)-promoter-reporter construct (DCLK1-L-LUC) was several-fold higher in HEKmGAS/HCT116 cells compared to that in HEKC cells, suggesting that β-catenin binding to 5'($\alpha$)-promoter may contribute to increased activation of DCLK1-L-LUC vector (FIG. 5B). HEK293 cells were transiently co-transfected with either control-vector or mGAS-vector to express high levels of PG, along with DCLK1-L-LUC vector. Transcriptional activity of DCLK1-L-LUC in the presence of PG expression was significantly increased in HEK293 cells (FIG. 5C). Transcriptional activity of DCLK1-L-LUC-vector was significantly reduced in HEKmGAS/HCT116 cells to control HEKC levels, on co-transfection with β-catenin siRNA (FIGS. 5D and 5E); efficacy of β-catenin-siRNA was confirmed (FIG. 17). The results suggest that β-catenin, activated in response to PG, may have contributed to elevated levels of DCLK1 in mouse colons and HEK293 cells, previously measured in response to PG. Possible role of NF-κβ-binding-sites in regulating 5'($\alpha$)-promoter was examined by co-transfecting HEKC/HEKmGAS cells with NF-κBp65-siRNA and DCLK1-L-LUC vector. Relative activity of DCLK1-L-LUC vector was similar in control-siRNA vs NF-κBp65-siRNA treated cells, corresponding to relative levels of DCLK1-L transcript in control vs treated cells (FIG. 17B); the latter results strongly suggest that NF-κβ-binding-sites do not play a significant role in activating/regulating the 5'($\alpha$)-promoter in these cells.

β-catenin binding to the five potential TCF4/LEF binding-sites in 5' ($\alpha$)-promoter (FIG. 5A), was determined in ChIP assays. TCF4/LEF sites at −1904 and −1591 were the only functional β-catenin binding-sites in the indicated cells (FIG. 6A). Representative ChIP data from all three cell-lines confirmed that non-tumorigenic HEKC cells, lacking activated β-catenin (FIG. 5B), were negative for β-catenin binding to both sites, while tumorigenic cell lines (HEKmGAS, HCT116) were positive (FIG. 6B-6D). HEK293 cells were transiently transfected with either control or mGAS (PG expressing) vector, and analyzed by ChIP assays (FIG. 6E-6F). Relative binding of β-catenin to the two TCF4 binding-sites, in the presence or absence of mGAS expression, from several experiments, is presented as % of total β-catenin (input) in the cells (FIG. 6G). β-catenin binding to both sites increased significantly in HEK293 cells transfected with mGAS-vector. For reasons unknown, relative binding of β-catenin to −1904 site was significantly higher than that to −1591 site in HEKmGAS/HCT116 cells (FIG. 6G).

Figures 7A, 7B, 7C, 7D, 7E:
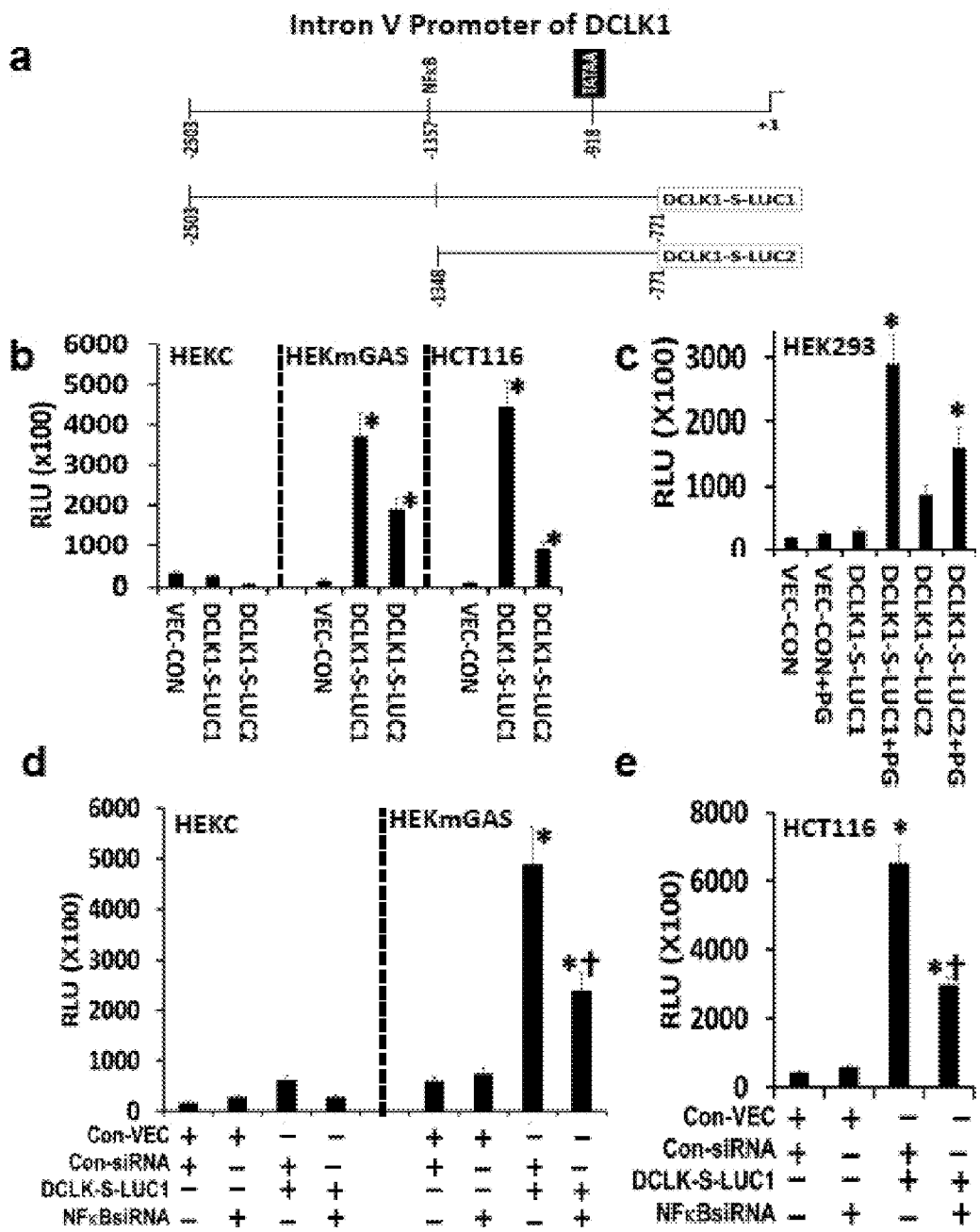

Role of NF-κB Binding-Site in Regulating Transcriptional Activity of IntronV(β)-Promoter of hDCLK1-Gene By in silico analysis, a single NF-κB binding site (~439 bps, 5' of a consensus TATA box), but no TCF4/LEF sites, were identified within 3 kb of IntronV(β)-promoter (FIG. 7A). Role of NF-κB in regulating transcriptional activity of IntronV(β)-promoter was examined by using two promoter-reporter constructs (FIG. 7A). NF-κB cis-element was present in DCLK1-S-LUC-1, but absent in DCLK1-S-LUC-2 (FIG. 7A). Transcriptional activity of both promoter-reporter constructs was negligible in HEKC cells (FIG. 7B), known to be negative for activated NF-κBp65. Relative transcriptional activity of LUC-1 was ~2-4 fold higher in HEKm-GAS/HCT116 cells, compared to that of LUC-2 construct (FIG. 7B), suggesting an important role of NF-κB binding-site in mediating increased activation of IntronV(β)-promoter. Transcriptional activity of LUC-2 was also elevated in HEKmGAS/HCT116 cells (FIG. 7B), suggesting endogenous factor(s), other than p65, may also activate IntronV (β)-promoter. PG is overexpressed in hCRCs, and maybe a prognostic marker for hCRC patients. In the presence of PG (mGAS-vector), transcriptional activity of LUC-1 increased by ~10-15-fold in HEK293 cells (FIG. 7C), confirming an important role of NF-κB binding site in transcriptional activation of IntronV(β)-promoter in response to PG. Surprisingly transcriptional activity of LUC-2 (negative for NF-κB binding-site) was also increased by ~3-5-fold, suggesting that cis-elements other than NF-κB, might also respond to PG. Cells transfected with LUC1-vector were also co-transfected with either control- or NF-κBp65-siRNA (FIG. 7D-7E). Loss of NF-κBp65 expression in NF-κBp65-siRNA transfected cells (FIG. 17B), resulted in reduction of transcriptional activity of LUC-1 in HEKmGAS/HCT116 cells by >50% (FIG. 7D-7E), to levels measured with LUC-2 (FIG. 7B). The results suggest that the single NF-κB cis-element plays an important role in transcriptional activation of IntronV(β)-promoter, and hence the expression of S-isoform, in transformed/cancer cells.

Figures 8A, 8B, 8C, 8D, 8E, 8F:
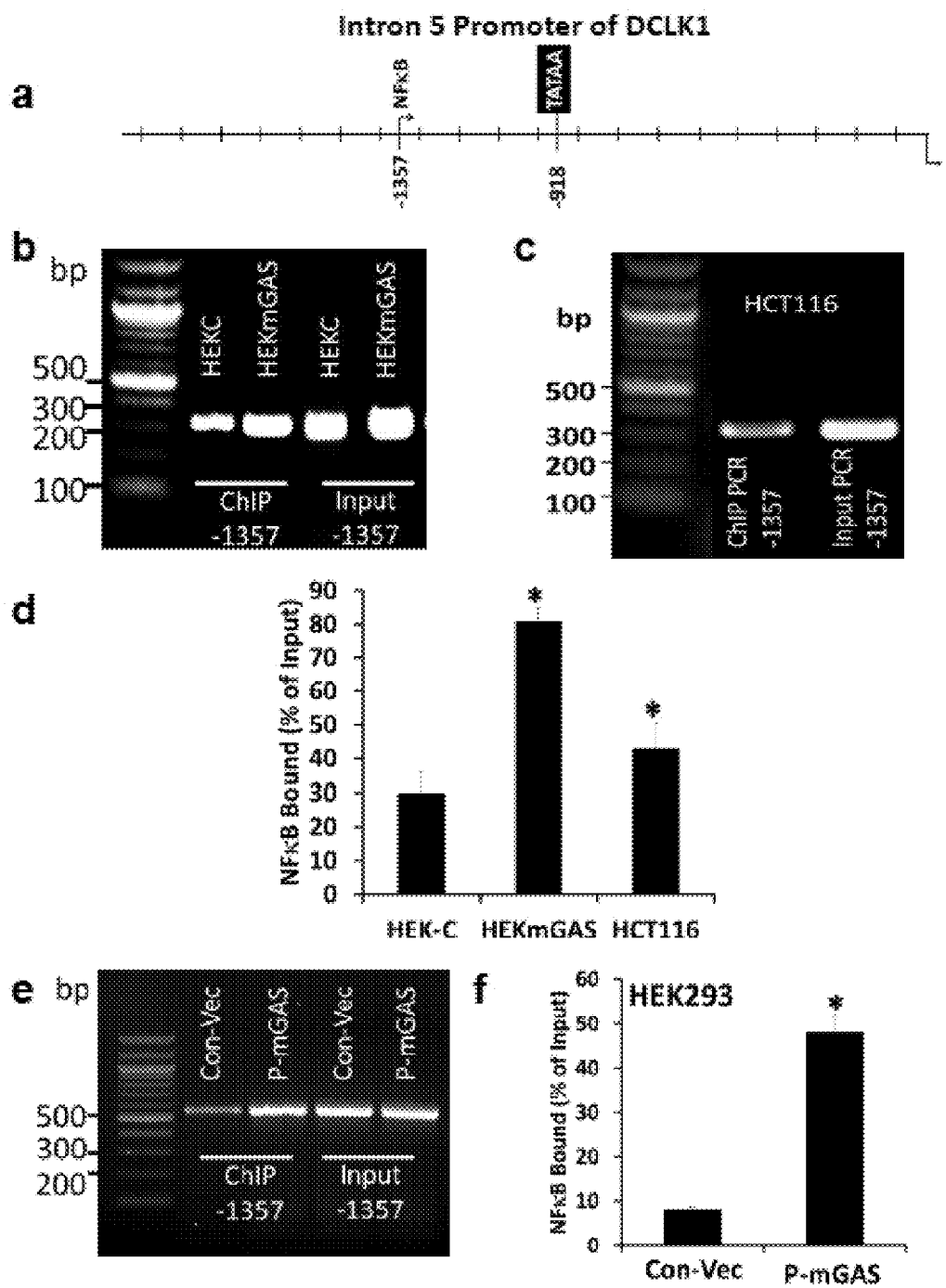

Representative ChIP data confirms binding of NF-κBp65 to NF-κB binding-site in IntronV-promoter (FIG. 8A), in situ (FIG. 8B-8C). Almost 80-90% of total NF-κBp65 was bound to NF-κB binding-site in HEKmGAS/HCT116 cells. Surprisingly, ~30-40% of total NF-κBp65 was also bound in HEKC cells (FIG. 8D), even though transcriptional activity of the promoter-reporter construct was negligible in these cells (FIGS. 7B and 7D), suggesting that either a threshold of NF-κB binding is required, or other factors activate IntronV(β)-promoter, in the presence of NF-κBp65. The % bound NF-κBp65 increased by ~5-fold in HEK293 cells overexpressing PG (mGAS vector) (FIG. 8E-8F).

High Expression of DCLK1-S in AdCA Samples from CRC Patients is Associated with Poor Patient Survival The expression pattern of DCLK1-S transcript in relation to clinicopathological parameters was analyzed using an independent cohort of patient specimens, as described herein. High-expression of DCLK1-S significantly correlated with overall poor patient survival in patients with Stages I-IV disease (FIG. 9A), or patients with only curatively resected Stages I-III disease (FIG. 9B), with significantly worse disease free survival (FIG. 9C), which significantly correlated with pathological T-category and lymphatic vessel involvement (Table 4). Moreover, by multivariate analysis, overexpression of DCLK1-S emerged as an independent prognostic factor in CRC patients (Table 5).

TABLE 7

| Variable | | n | High (n = 46) | Low (n = 46) | P Value |
|---|---|---|---|---|---|
| Gender | Male | 57 | 29 | 28 | 1.000 |
| | Female | 35 | 17 | 18 | |
| Age (years) | <68 (median) | 47 | 20 | 27 | 0.211 |
| | ≥68 | 45 | 26 | 19 | |
| Tumor Size | ≥4.1 cm (median) | 47 | 22 | 25 | 0.617 |
| | <4.1 cm | 45 | 24 | 21 | |
| Histological Type | Differentiated | 82 | 40 | 42 | 0.738 |
| | Undifferentiated | 10 | 6 | 4 | |
| Pathological T Category | pT1 | 11 | 3 | 8 | 0.019* |
| | pT2 | 12 | 4 | 8 | |
| | pT3 | 59 | 32 | 27 | |
| | pT4 | 10 | 7 | 3 | |
| Vessel Involvement | Positive | 42 | 25 | 17 | 0.143 |
| | Negative | 50 | 21 | 29 | |
| Lymphatic Vessel Involvement | Positive | 70 | 41 | 29 | 0.007* |
| | Negative | 22 | 5 | 17 | |
| Lymph Node Metastasis | N0 | 51 | 21 | 30 | 0.093 |
| | N1 | 41 | 25 | 16 | |
| Distant Metastasis | M0 | 71 | 35 | 36 | 1.000 |
| | M1 | 21 | 11 | 10 | |
| TNM Stage | Stage I | 19 | 5 | 14 | 0.061 |
| | Stage II | 30 | 15 | 15 | |
| | Stage III | 22 | 15 | 7 | |
| | Stage IV | 21 | 11 | 10 | |

Pearson's chi-square-test;
*p < 0.05

Clinicopathological variables and DCLK1-S expression in 92 colorectal cancer patients. Samples were obtained from patients with colonic adenocarcinomas at CRC stages of I-IV, from 92 patients in Japan. The relative expression levels of DCLK1-S were analyzed by qRT-PCR, and high/low expression groups were classified by the median expression values in cancer tissues.

TABLE 8

| | Univariate | | | Multivariate | | |
|---|---|---|---|---|---|---|
| Variables | HR | 95% CI | p valve | HR | 95% CI | p value |
| Gender (Male vs. Female) | 1.2 | 0.52-2.77 | 0.66 | 1.53 | 0.57-4.13 | 0.41 |
| Age (≥68 (median) vs. <68) | 1.26 | 0.58-2.75 | 0.56 | 0.77 | 0.29-2.05 | 0.6 |
| Histological type (Undifferentiated/differentiated) | 3.49 | 1.39-8.77 | 0.008* | 4.46 | 1.54-12.9 | 0.006* |
| Tumor Size (≥4.1 cm (median) vs. <4.1 cm) | 1.33 | 0.62-2.87 | 0.47 | 1.22 | 0.48-3.11 | 0.68 |
| Lymph Node metastasis(present/absent) | 13 | 3.90-43.1 | <0.001* | 4.70 | 1.17-18.8 | 0.03* |

TABLE 8-continued

| | Univariate | | | Multivariate | | |
|---|---|---|---|---|---|---|
| Variables | HR | 95% Cl | p valve | HR | 95% Cl | p value |
| Distant metastasis(present/absent) | 9.67 | 4.35-21.5 | <0.001* | 11.2 | 3.65-34.6 | <0.001* |
| DCLK1-S expresion(high/low) | 3.55 | 1.41-8.99 | 0.008* | 7.93 | 2.25-27.9 | 0.0014* |

HR = hazard ratio
Cl = confidence level
*p < 0.05

Table 8 Multivariate Analysis for Predictors of Overall Survival. Cox's proportional hazards models were used to estimate hazard ratios (HRs) for overall survival. In multivariate analysis, undifferentiated histological type, lymph node metastasis, distant metastasis, and high DCLK1-S expression were independent prognostic factors in the cohort of 92 CRC patients. Cl=confidence level; *p<0.05 for the indicated variables.

Example 2

It was recently reported, and described above, that hCRCs express short-transcripts of DCLK1 (DCLK1-S) from an alternate promoter located within IntronV of DCLK1-gene, while normal human colons express the canonical long transcript (DCLK1-L) from 5'($\alpha$)-promoter. Also demonstrated is that 5'($\alpha$)-promoter is hypermethylated in hCRCs, resulting in epigenetic silencing and loss of expression of DCLK1-L in hCRCs. Although 5'($\alpha$)-promoter is differentially methylated in normal human colons vs hCRCs, methylation status of IntronV($\beta$)-promoter does not change. The inventors contemplated that differential expression of DCLK1-S in normal colons vs hCRCs is perhaps due to differences in transcriptional activity of the promoter in normal vs cancer cells. To test this, the inventors used several in silico and molecular biology approaches, and report that FOXD3 is a potent transcriptional inhibitor of the IntronV($\beta$)-promoter, resulting in the absence of DCLK1-S expression in normal human colons. The results suggest that FOXD3 gene becomes methylated during colon carcinogenesis, causing loss of FOXD3 expression, and results in the expression of DCLK1-S in hCRCs. In order to examine pathophysiological relevance of the loss of FOXD3 and gain of DCLK1-S expression in hCRCs, the relative levels of FOXD3/DCLK1-S were measured by qRT-PCR in a cohort of 92 CRC patients, in relation to overall survival and clinicopathological parameters. Patients expressing high-DCLK1-S/low-FOXD3 had significantly worse overall-survival compared to patients expressing low-DCLK1-S/high-FOXD3. High expression of DCLK1-S, in conjunction with low expression of FOXD3, was a stronger independent prognostic factor than expression of high levels of DCLK1-S alone. Based on these studies, FOXD3 is identified as a potent repressor of IntronV($\beta$)-promoter of hDCLK1-gene in normal cells, and that loss of FOXD3 expression due to hypermethylation and silencing of FOXD3 gene during colon carcinogenesis, results in the expression of DCLK1-S in hCRCs, representing an important biomarker of hCRCs. The findings also suggest a prognostic/diagnostic value of measuring relative expression levels of DCLK1-S/FOXD3 in tumors of CRC patients. It is speculated that loss of DCLK1-L and FOXD3 expression, associated with increased expression of DCLK1-S can be used as an early diagnostic marker of epigenetic changes, associated with colon carcinogenesis in humans.

In summary, DCLK1 reportedly marks quiescent stem cells at the position 4 of intestinal-crypts and plays a role in maintaining intestinal lineages remains (Kantara et al., *Cancer Res.* 2014, 74(9):2487-98). Downregulation of DCLK1, results in loss of cancer stem cell markers and tumorigenic potential of hCCCs (Kantara et al., *Cancer Res.* 2014, 74(9):2487-98; Sureban et al., *J Nanobiotechnology.* 2011, 9:40).

FOXD3 is a potent repressor of the IntronV($\beta$)-promoter of the human DCLK1 gene in normal cells. Loss of FOXD3 expression due to hypermethylation and silencing of FOXD3 gene during colon carcinogenesis, results in the expression of DCLK1-S in hCRCs, representing an important biomarker of hCRCs. There is prognostic/diagnostic value in measuring relative expression levels of DCLK1-S/FOXD3 in tumors of CRC patients. The loss of DCLK1-L and FOXD3 expression, associated with increased expression of DCLK1-S can be used as an early diagnostic marker of epigenetic changes, associated with colon carcinogenesis in humans.

The invention claimed is:

1. A doublecortin like kinase 1 short form (DCLK1-S) specific antibody composition that specifically binds a DCLK1-S peptide consisting of the sequence MLELIE (SEQ ID NO:1).

2. The composition of claim 1, wherein the DCLK1-S specific antibody is a monospecific polyclonal antibody.

3. The composition of claim 1, wherein the DCLK1-S specific antibody is a monoclonal antibody.

4. The composition of claim 1, wherein the DCLK1-S specific antibody is bound to a solid support.

5. An immunogenic composition comprising an immunogen comprising eight copies of a peptide consisting of the amino acid sequence of SEQ ID NO:1 coupled to a multiple antigen peptide-octavalent (MAP-8).

6. The immunogenic composition of claim 5, wherein the MAP-8 peptide is fused to a lysine-branched scaffold.

7. The immunogenic composition of claim 5, wherein the immunogen is coupled to Keyhole limpet hemocyanin (KLH).

8. The immunogenic composition of claim 5, further comprising an adjuvant.

9. The immunogenic composition of claim 8, wherein the adjuvant is complete Freund's adjuvant (CFA) or incomplete Freund's adjuvant (IFA).

10. An antibody that specifically binds an immunogen comprising eight copies of a peptide consisting of the amino acid sequence of SEQ ID NO:1 coupled to a multiple antigen peptide-octavalent (MAP-8).

11. The antibody of claim 10, wherein the DCLK1-S specific antibody is a monospecific polyclonal antibody.

12. The antibody of claim 10, wherein the DCLK1-S specific antibody is a monoclonal antibody.

13. A method of detecting DCLK1-S in a sample comprising contacting a sample with an antibody of claim 1 and detecting binding of the antibody with DCLK1-S from the sample.

14. The method of claim 13, wherein the method is an enzyme linked immunosorbent assay (ELISA).

15. The method of claim 13, wherein the sample is suspected of comprising colon cancer cells.

16. The method of claim 13, wherein the sample is a colonic mucosal sample.

17. The method of claim 13, wherein the sample is a tissue section.

18. The method of claim 13, wherein the sample is from a patient that has undergone treatment for colon cancer.

19. The method of claim 13, further comprising detecting FOXD3 in the sample.

20. The method of claim 13, further comprising detecting COL3A1 or SPARC in the sample.

* * * * *

SEQUENCE LISTING

<160> NUMBER OF SEQ ID NOS: 26

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 1

Met Leu Glu Leu Ile Glu
1               5

```
<210> SEQ ID NO 2
<211> LENGTH: 35
<212> TYPE: DNA
<213> ORGANISM: Artificial Sequence
<220> FEATURE:
<223> OTHER INFORMATION: Synthetic Primer

<400> SEQUENCE: 2
atgctgaaac gcgagagaaa ccgcgtatca acccc                           35

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
ggagtggtga aacgcctgta c                                          21

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
ggttccatta actgagctgg                                            20

<210> SEQ ID NO 5
<211> LENGTH: 29
<212> TYPE: DNA
<213> ORGANISM: Artificial Sequence
<220> FEATURE:
<223> OTHER INFORMATION: Synthetic Primer

<400> SEQUENCE: 5
acactaagac tgtgtccatg ttagaactc                                  29

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
aagccttcct ccgacacttc t                                          21

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
tcaatgagga ccagctccag                                            20

<210> SEQ ID NO 8
<211> LENGTH: 19
<212> TYPE: DNA
<213> ORGANISM: Artificial Sequence
<220> FEATURE:
<223> OTHER INFORMATION: Synthetic Primer
```

```
<400> SEQUENCE: 8
tccgagagag ttcgggtca                                              19

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
aagacgtcag ccttacgcag                                             20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
gagagatcct ctgcttccgc                                             20

<210> SEQ ID NO 11
<211> LENGTH: 18
<212> TYPE: DNA
<213> ORGANISM: Artificial Sequence
<220> FEATURE:
<223> OTHER INFORMATION: Synthetic Primer

<400> SEQUENCE: 11
agagctgtgt ctgcttgg                                               18

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
gttcattcca gggcagctta                                             20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
taagctgccc tggaatgaac                                             20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
cccaagctat gcactctggt                                             20

<210> SEQ ID NO 15
<211> LENGTH: 20
```

```
<212> TYPE: DNA
<213> ORGANISM: Artificial Sequence
<220> FEATURE:
<223> OTHER INFORMATION: Synthetic Primer

<400> SEQUENCE: 15
ctgtatccac tgccctctgt                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
gcaaagctat cttcaggagg                                              20

<210> SEQ ID NO 17
<211> LENGTH: 25
<212> TYPE: DNA
<213> ORGANISM: Artificial Sequence
<220> FEATURE:
<223> OTHER INFORMATION: Synthetic Primer

<400> SEQUENCE: 17
tttaggggtg tagttaagtt agatg                                        25

<210> SEQ ID NO 18
<211> LENGTH: 22
<212> TYPE: DNA
<213> ORGANISM: Artificial Sequence
<220> FEATURE:
<223> OTHER INFORMATION: Synthetic Primer

<400> SEQUENCE: 18
aacctctctc tccaaaaaaa aa                                           22

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
acatgactgt gggcaaatga                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
cccaagctat gcactctggt                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
```

```
ggtgcttccg ttcaaagtgt                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
cagtctcagg aataccttgc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
cctcctgaag atagctttgc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
cagtctcagg aataccttgc                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
gagaaccgcg tatcaacccc                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
gtgacgtaga ggagccgcca                                              20
```